United States Patent [19]

Chakraborty et al.

[11] Patent Number: 5,266,689

[45] Date of Patent: Nov. 30, 1993

[54] EIMERIA MAXIMA 16S RDNA PROBES

[75] Inventors: Prasanta R. Chakraborty, Scotch Plains; Michael Dashkevicz, Jamesburg; Alex Elbrecht, Watchung; Scott D. Feighner, Scotch Plains; Paul A. Liberator, Holmdel, all of N.J.; Helen Profous-Juchelka, Staten Island, N.Y.

[73] Assignee: Merck and Co., Inc., Rahway, N.J.

[21] Appl. No.: 879,647

[22] Filed: May 12, 1992

Related U.S. Application Data

[63] Continuation-in-part of Ser. No. 706,628, May 29, 1991, abandoned.

[51] Int. Cl.$^5$ .................... C07H 21/04; C12Q 01/68; C12P 19/34
[52] U.S. Cl. ..................... 536/24.32; 435/6; 435/91
[58] Field of Search ............... 536/27, 24.30, 24.31, 536/24.32, 24.33; 435/6

[56] References Cited

U.S. PATENT DOCUMENTS

| | | | |
|---|---|---|---|
| 4,522,759 | 11/1985 | Davis et al. | 424/93 |
| 4,544,548 | 10/1985 | Davis et al. | 424/93 |
| 4,752,475 | 6/1988 | Davis et al. | 424/93 |
| 4,863,731 | 9/1989 | Davis et al. | 424/93 |

FOREIGN PATENT DOCUMENTS

WO85/00752  8/1984  World Int. Prop. O.

OTHER PUBLICATIONS

Hans et al. (1987) Biochemistry, vol. 26, pp. 1617–1625.
Joyner and Long, Avian Path. 3:145–157, 1974.
Shirley, Research In Avian Coccidiosis, pp. 13–35, 1985.
Hasegawa et al., J. Mol. Evol. 22: 32–38, 1985.
Johnson et al., Exp. Parasitol. 63: 272–278, 1987.
Dame and McCutchan, J. Biol. Chem. 258: 6984–6990, 1983.
Langsley et al., Nucleic Acids Res. 11:8703–8717, 1983.
Ellis and Blumstead, Parasitol. 101: 1–6, 1990.
Johnson et al., System Parasitol. 18: 1–8, 1991.
McCutchan et al., Mol. Biochem. Parasitol. 28: 63–68, 1988.
Forsman et al., Appld. Environ. Microbiol. 56: 949–955, 1990.
Dans et al., Nucleic Acid Res. 165: r87–r173, 1988.
Ferriera et al., Mol. Biochem. Parasitol. 19:103–109, 1986.
Arreaza et al., Exp. Parasitol. 72: 103–105, 1991.
Saiki et al., Science 239: 487–491, 1988.
Labarca and Paigen, Anal. Biochem. 102: 344–352, 1980.
Johnston et al., Electrophoresis 11: 355–360, 1990.
Jackson, parasitol 54: 87–93, 1964.
Edgar, Trans. Am. Micro. Soc. 62:237–242, 1954.
Neefs et al., Nucleic Acids Res. 18S: 2237–2317, 1990.
Clark, Nucleic Acids Res. 16: 9677–9686, 1988.
Vogelstein & Gillespie, Proc. Natl. Acad Sci. U.S.A. 76: 615–619, 1979.
Sanger et al., J. Mol. Biol. 143: 161–178, 1980.
Chen and Seeburg, DNA, 4: 165–170, 1985.
Tabor and Richardson, Proc. Natl. Acad. Sci. U.S.A. 84: 4767–4771, 1987.
Freier et al., Proc. Natl. Acad. Sci. U.S.A. 83: 9373–9377, 1986.
Suggs et al., ICN-UCLA Symp. Dev. Biol. Using Purified Genes, 23: 683–693, 1981.
Chirgwin et al., Biochemistry 18: 5294–5299, 1979.

*Primary Examiner*—Margaret Moskowitz
*Assistant Examiner*—Lisa Bennett
*Attorney, Agent, or Firm*—Christine E. Carty; Jack L. Tribble; Hesna J. Pfeiffer

[57] ABSTRACT

Unique species-specific *Eimeria maxima* DNA probes comprising divergent DNA sequences are disclosed. The probes are complementary to a small subunit ribosomal RNA gene of *Eimeria maxima*.

2 Claims, 40 Drawing Sheets

```
  1  TAGTCATATG CTTGTCTCAA AGATTAAGCC ATGCATGTCT   40
 41  AAGTATAAGC TTTTATACGG TGAAACTGCG AATGGCTCAT   80
 81  TAAAACAGTT ATAGTTTATT TGATGGTCTC TTTTACATGG  120
121  ATAACCATGG TAATTCTATG GCTAATACAT GCGCAAGGGC  160
161  CTCCTCCTCT GGAGGGGCTG TGTTTATTAG ATACAAAACC  200
201  AACCCACCTT GTGTGGAGTC TTGGTGATTC ATAGTAACCG  240
241  AACGGATCGC AGTTGGCTTT CGGGCCCGCG ATGGATCATT  280
281  CAAGTTTCTG ACCTATCAGC TTTCGACGGT AGGGTATTGG  320
321  CCTACCGTGG CAGTGACGGG TAACGGGGAA TTAGGGTTCG  360
361  ATTCCGGAGA GGGAGCCTGA GAAACGGCTA CCACATCTAA  400
401  GGAAGGCAGC AGGCGCGCAA ATTACCCAAT GAAACAGTT   440
441  TCGAGGTAGT GACGAGAAAT AACAATACAG GCATCTTAT   480
481  GCTTTGTAAT TGGAATGATG GAATGTAAA ACCCTTCCAG   520
521  AGTAACAATT GGAGGGCAAG TCTGGTGCCA GCAGCCGCGG  560
561  TAATTCCAGC TCCAATAGTG TATATTAGAG TTGTTGCAGT   600
601  TAAAAAGCTC GTAGTTGGAT TTCTGTCGTG GTCAGCCTGC   640
641  GCTGCCCGTA TGGGTGTGCG CGTGGTTTGC CCTCGGCTTT   680
681  TTTCTGGTAG CCTCCTGCGC TTAATTGCGT GGGCTGGTGT   720
721  TCCGGAACTT TTACTTTGAG AAAAATAGAG TGTTTCAAGC   760
761  AGGCTTGTCG CCCTGAATAC TGCAGCATGG AATAATAAGA   800
801  TAGGACCTCG GTTCTATTTT GTTGGTTTCT AGGACCAAGG   840
841  TAATGATTAA TAGGGACAGT TGGGGGCATT CGTATTTAAC   880
881  TGTCAGAGGT GAAATTCTTA GATTTGTTAA AGACGAACTA   920
 ?1  CTGCGAAAGC ATTTGCCAAG GATGTTTTCA TTAATCAAGA   960
```

FIG.1A

```
 961 ACGACAGTAG GGGGTTTGAA GACGATTAGA TACCGTCGTA 1000
1001 ATCTCTACCA TAAACTATGC CGACTAGAGA TAGGGAAATG 1040
1041 CCTACCTTGG CTTCTCCTGC ACCTCATGAG AAATCAAAGT 1080
1081 CTCTGGGTTC TGGGGGAGT ATGGTCGCAA GGCTGAAACT 1120
1121 TAAAGGAATT GACGGAGGGG CACCACCAGG CGTGGAGCCT 1160
1161 GCGGCTTAAT TTGACTCAAC ACGGGAAAC TCACCAGGTC 1200
1201 CAGACATGGG AAGGATTGAC AGATTGATAG CTCTTTCTTG 1240
1241 ATTCTATGGG TGGTGGTGCA TGGCCGTTCT TAGTTGGTGG 1280
1281 AGTGATCTGT CTGGTTAATT TCGATAACGA ACGAGACCTT 1320
1321 GGCCTGCTAA ATAGGGTCGG TAACTTCGGT TATCGTATCA 1360
1361 CTTCTTAGAG GGACTTTGCG TGTCTAACGC AAGGAAGTTT 1400
1401 GAGGCAATAA CAGGTCTGTG ATGCCCTTAG ATGTTCTGGG 1440
1441 CTGCACGCGC GCTACACTGA TGCATGCAAC GAGTTTTTAC 1480
1481 CTTGACCGAC GGGGCTGGGT AATCTTCTGA GGGTGCATCG 1520
1521 TGATGGGGAT AGATTATTGC AATTATTAGT CTTCAACGAG 1560
1561 GAATGCCTAG TAGGCGCAAG TCAGCAGCTT GCGCCGATTA 1600
1601 CGTCCCTGCC TCTTGTACAC ACCGCCCGTC GCTGCAACCG 1640
1641 ATCGGAGGGT CCTGTGAATT CATCGGACTG GCCATTCTCA 1680
1681 CTTTGGGGCT GGCCGGGAAG TTGCGTAAAT AGAGCCCTCT 1720
1721 AAAGGATGCA AAGTCGTAA CACGGTTT 1748
```

FIG.1B

```
TAGTCATATG CTTGTCTCAA AGATTAAGCC ATGCATGTCT    40

AAGTATAAAC TTTTATACGG TGAAACTGCG AATGGCTCAT    80

TAAAACAGTT ATAGTTTATT TGATGGTCAT TTTTACATGG   120

ATAACCATGG TAATTCTATG CTAATACAT GCGCATAGGC    160

TTCCTTCTTT GAAGGGGCTG TGTTTATTAG ATACAAAACC   200

AACCCACCTT GTGGAGCCTT GGTGATTCAT AGTAACCGAA   240

CGGATCGCAG TTGGCTTTCG GGCCCGCGAT GGATCATTCA   280

AGTTTCTGAC CTATCAGCTT TCGACGGTAG GGTATTGGCC   320

TACCGTGGCA GTGACGGGTA ACGGGGAATT AGGGTTCGAT   360

TCCGGAGAGG GAGCCTGAGA AACGGCTACC ACATCTAAGG   400

AAGGCAGCAG GCGCGCAAAT TACCCAATGA AACAGTTTC    440

GAGGTAGTGA CGAGAAATAA CAATACAGGG CATTTAATGC   480

TTTGTAATTG GAATGATGGG AATGTAAAAC CCTTCCAGAG   520

TAACAATTGG AGGGCAAGTC TGGTGCCAGC AGCCGCGGTA   560

ATTCCAGCTC CAATAGTGTA TATTAGAGTT GTTGCAGTTA   600

AAAAGCTCGT AGTTGGATTT CTGTCGTGGT CAGCCTGCGC   640

TGCCCGTATG GGTGTGCGCG TGGTTTGCCC GCGGCTTTCT   680

TCCGGTAGCC TCCGGCTCTT AATTGCGTCG GTGGGTGTTC   720

TGGAACTTTT ACTTTGAGAA AAATAGAGTG TTTCAAGCAG   760

GCTTGTCGCC CTGAATACTG CAGCATGGAA TAATAAGATA   800

GGACCTCGGT TCTATTTTGT TGGTTCTAG GACCAAGGTA    840

ATGATTAATA GGGACAGTTG GGGCATTCG TATTTAACTG    880

TCAGAGGTGA AATTCTTAGA TTTGTTAAAG ACGAACTACT   920

GCGAAAGCAT TTGCCAAGGA TGTTTTCATT AATCAAGAAC   960
```

FIG.2A

```
GACAGTAGGG GGTTTGAAGA CGATTAGATA CCGTCGTAAT    1000
CTCTACCATA AACTATGCCG ACTAGAGATA GGGAAATGCC    1040
TACCTTGGCT TCTCCTGCAC CTCATGAGAA ATCAAAGTCT    1080
CTGGGTTCTG GGGGAGTAT GGTCGCAAGG CTGAAACTTA     1120
AAGGAATTGA CGGAGGGGCA CCACCAGGCG TGGAGCCTGC    1160
GGCTTAATTT GACTCAACAC GGGGAAACTC ACCAGGTCCA    1200
GACATGGGAA GGATTGACAG ATTGATAGCT CTTTCTTGAT    1240
TCTATGGGTG GTGGTGCATG GCCGTTCTTA GTTGGTGGAG    1280
TGATCTGTCT GGTTAATTTC GATAACGAAC GAGACCTTGG    1320
CCTGCTAAAT AGGGTCGGTG ACCTCGGTCA CGCATCGCTT    1360
CTTAGAGGGA CTTTGCGTGT CTAACGCAGG GAAGTTCGAG    1400
GCAATAACAG GTCTGTGATG CCCTTAGATG TTCTGGGCTG    1440
CACGCGCGCT ACACTGATGC ATGCAACGAG TTCTTACCTT    1480
GGCCGACGGG GCTGGGTAAT CTTGTGGGGG TGCATCGTGA    1520
TGGGATAGA TTATTGCAAT TATTAGTCTT CAACGAGGAA     1560
TGCCTAGTAG GCGCAAGTCA GCAGCTTGCG CCGATTACGT    1600
CCCTGCCTCT TGTACACACC GCCCGTCGCT GCAACCGATG    1640
GAGGGTCCTG TAAATTCATC GGACTGGCCA ACCCCATTTT    1680
GGGGCTGGCT GGAAAGTTGC GTAAATAGAG CCCTCTAAAG    1720
GATGCAAAAG TCGTAACACG GTTT                     1744
```

FIG. 2B

```
  1  TAGTCATATG CTTGTCTCAA AGATTAAGCC ATGCATGTCT   40
 41  AAGTATAAAC TTTTATACGG TGAAACTGCG AATGGCTCAT   80
 81  TAAAACAGTT ATAGTTTATT TGATGGTCTT TTTTACATGG  120
121  ATAACCATGG TAATTCTATG GCTAATACAT GCGCAAAAGC  160
161  TACCTTCTTT GGAGGAGCTG TGTTTATTAG ATACAAAACC  200
201  AGCCCACAAT TCTTGTGGAG TCTTGGTGAT TCATAGTAAC  240
241  CGAACGGATC GCAGTTGGCT TTCGGGCCCG CGATGGATCA  280
281  TTCAAGTTTC TGACCTATCA GCTTCGACG  GTAGGGTATT  320
321  GGCCTACCGT GGCAGTGACG GGTAACGGGG AATTAGGGTT  360
361  CGATTCCGGA GAGGGAGCCT GAGAAACGGC TACCACATCT  400
401  AAGGAAGGCA GCAGGCGCGC AAATTACCCA ATGAAAACAG  440
441  TTTCGAGGTA GTGACGAGAA ATAACAATAC AGGGCATTTT  480
481  ATGCTTTGTA ATTGGAATGA TGGGAATGTA AAACCCTTCC  520
521  AGAGTAACAA TTGGAGGGCA AGTCTGGTGC CAGCAGCCGC  560
561  GGTAATTCCA GCTCCAATAG TGTATATTAG AGTTGTTGCA  600
601  GTTAAAAAGC TCGTAGTTGG ATTTCTGTCG TGGTCAGCTT  640
641  GCGCTGCCCG TATGGGTGTG CGCGTGGTTT GCCCTCGGCA  680
681  TTCTTCCGGT AGCTTGTGGC GCTTAATTGC GTCTGCAAGT  720
721  GCCCTGGAAC TTTTACTTTG AGAAAAATAG AGTGTTTCAA  760
761  GCAGGCTTGT CGCCCTGAAT ACTGCAGCAT GGAATAATAG  800
801  GATAGGACCT CGGTTCTATT TTGTTGGTTT CTAGGACCAA  840
841  GGTAATGATT AATAGGGACA GTTGGGGGCA TTCGTATTTA  880
881  ACTGTCAGAG GTGAAATTCT TAGATTTGTT AAAGACGAAC  920
921  TACTGCGAAA GCATTTGCCA AGGATGTTTT CATTAATCAA  960
```

FIG.3A

```
 961  GAACGACAGT AGGGGGTTTG AAGACGATTA GATACCGTCG 1000
1001  TAATCTCTAC CATAAACTAT GCCGACTAGA GATAGGAAAA 1040
1041  CGCCTCCCTT GGCTTCTCCT GGACCTCATG AGAAATCAAA 1080
1081  GTCTCTGGGT TCTGGGGGA GTATGGTCGC AAGGCTGAAA 1120
1121  CTTAAAGGAA TTGACGGAGG GGCACCACCA GGCGTGGAGC 1160
1161  CTGCGGCTTA ATTTGACTCA ACACGGGGAA ACTCACCAGG 1200
1201  TCCAGACATG GAAGGATTG ACAGATTGAT AGCTCTTTCC 1240
1241  TGATTCTATG GGTGGTGGTG CATGGCCGTT CTTAGTTGGT 1280
1281  GGAGTGATTT GTCTGGTTAA TTTCGATAAC GAACGAGACC 1320
1321  TTGGCCTGCT AAATAGGGTC GGTGACCTCG GTTACCGTAT 1360
1361  CACTTCTTAG AGGGACATTG CGTGTCTAAC GCAAGGAAGT 1400
1401  TTGAGGCAAT AACAGGTCTG TGATGCCCTT AGATGTTCTG 1440
1441  GGCTGCACGC GCGCTACACT GATGCATGCA ACGAGTTTTC 1480
1481  ACCTTGTCCG ATGGGCTGG GTAATCTTGT GAGGGTGCAT 1520
1521  CGTGATGGGG ATAGATTATT GCAATTATTA GTCTTCAACG 1560
1561  AGGAATGCCT AGTAGGCGCA AGTCAGCAGC TTGTGCCGAT 1600
1601  TACGTCCCTG CCTCTTGTAC ACACCGCCCG TCGCTGCAAC 1640
1641  CGATCGGAGG GTCCTGTAAA TTCATCGGAC TGACCAGCCC 1680
1681  CAACTTGGGG CTGGTCGGAA AGTTGCGTAA ATAGAGCCCT 1720
1721  CTAAAGGATG CAAAAGTCGT AACACGGTTT      1750
```

FIG.3B

```
  1  TAGTCATATG CTTGTCTCAA AGATTAAGCC ATGCATGTCT   40
 41  AAGTATAAGC TTTTATACGG TGAAACTGCG AATGGCTCAT   80
 81  TAAAACAGTT ATAGTTTATT TGATGGTCTT TTTTACATGG  120
121  ATAACCATGG TAATTCTATG CTAATACAT GCGCATAGGC  160
161  CTCCTCCTCT GGAGGGGCTG TGTTTATTAG CTACAAAACC  200
201  AACCCACTTT TGTGGAGCCT TGGTGATTCA TAGTAACCGA  240
241  ACGGATCGCA GTTGGCTTTC GGGCCCGCGA TGGATCATTC  280
281  AAGTTTCTGA CCTATCAGCT TTCGACGGTA GGGTATTGGC  320
321  CTACCGTGGC AGTGACGGGT AACGGGGAAT TAGGGTTCGA  360
361  TTCCGGAGAG GGAGCCTGAG AAACGGCTAC CACATCTAAG  400
401  GAAGGCAGCA GGCGCGCAAA TTACCCAATG AAAACAGTTT  440
441  CGAGGTAGTG ACGAGAAATA ACAATACAGG GCATTTATG  480
481  CTTTGTAATT GGAATGATGG GAATGTAAAA CCCTTCCAGA  520
521  GTAACAATTG GAGGGCAAGT CTGGTGCCAG CAGCCGCGGT  560
561  AATTCCAGCT CCAATAGTGT ATATTAGAGT TGTTGCAGTT  600
601  AAAAAGCTCG TAGTTGGATT TCTGTCGTGG TCTTCCTGTG  640
641  CTGCCCGTAT CGGTGCACGT GGCTTGCCCT CGACTTTCTT  680
681  CCGGTAGCCT CCTGCGCTTC ACTGCGTGGG CTGGTGTTCT  720
721  GGAACTTTTA CTTTGAGAAA AATAGAGTGT TCAAGCAGC  760
761  TTGTCGCCCT GAATACTGCA GCATGGAATA ATAAGATAGG  800
801  ACCTCGGTTC TATTTGTTG GTTTCTAGGA CCAAGGTAAT   840
841  GATTAATAGG GACAGTTGGG GGCATTCGTA TTTAACTGTC  880
881  AGAGGTGAAA TTCTTAGATT TGTTAAAGAC GAACTACTGC  920
921  GAAAGTTTGC CAAGGATGTT TTCATTAATC AAGAACGACA  960
```

FIG. 4A

```
 961  GTAGGGGGTT TGAAGACGAT TAGATACCGT CGTAATCTCT  1000
1001  ACCATAAACT ATGCCGACTA GAGATAGGGA AACGCCTACC  1040
1041  TTGGCTTCTC CTGCACCTCA TGAGAAATCA AGTCTCTGG   1080
1081  GTTCTGGGGG GAGTATGGTC GCAAGGCTGA AACTTAAAGG  1120
1121  AATTGACGGA GGGGCACCAC CAGGCGTGGA GCCGGGCCTT  1160
1161  AATTTGACTC AACACGGGGA AACTCACCAG GTCCAGACAT  1200
1201  GGGAAGGATT GACAGATTGA TAGCTCTTTC TTGATTCTAT  1240
1241  GGGTGGTGGT GCATGGCCGT TCTTAGTTGG TGGAGTGATC  1280
1281  TGTCTGGTTA ATTTCGATAA CGAACGAGAC CTTGGCCTGC  1320
1321  TAAATAGGGT CGGTGACCCT GGGTCACCAG GTCACCGCAT  1360
1361  CGCTTCTTAG AGGAACTTTG CGTGTCTAAC GCAAGGAAGT  1400
1401  TTGAGGCAAT AACAGGTCTG TGATGCCCTT AGATGTTCTG  1440
1441  GGCTGCACGC GCGCTACACT GATGCATGCA ACGAGTTTTT  1480
1481  ACCTTGCCCG ATGGGCGTGG GTAATCTTGT GAGGGTGCAT  1520
1521  CGTGATGGGG ATAGATTATT GCAATTATTA GTCTTCAACG  1560
1561  AGGAATGCCT AGTAGGCGCA AGTCAGCAGC TTGCGCCGAC  1600
1601  TAAGTCCCTG CCTCTTGTAC ACACCGCCCG TCGCTGCAAC  1640
1641  CGATCGGAGG GTCCTGTGAA TTCATCGGAT GGCCATCCCC  1680
1681  TTCTTGGGGC TGGCCGGGAA GTTGCGTAAA TAGAGCCCTC  1720
1721  TAAAGGATGC AAAAGTCGTA ACACGGTTT 1749
```

FIG.4B

```
  1  TAGTCATATG CTTGTCTCAA AGATTAAGCC ATGCATGTCT    40
 41  AAGTATAAGC TTTTATACGG TGAAACTGCG AATGGCTCAT    80
 81  TAAAACAGTT ATAGTTTATT TGATGGTCTC ATTTTACATG   120
121  GATAACCATG GTAATTCTAT GGCTAATACA TGCGCAAAGG   160
161  TCACCTCCTT TGGAGGGGCT GTGTTTATTA GATACAAAAC   200
201  CAACCCACTT AACGGTGGAG CCTTGGTGAT TCATAGTAAC   240
241  CGAACGGATC GCAGTTGGTT CTTTTGGACC CGCGATGGAT   280
281  CATTCAAGTT TCTGACCTAT CAGCTTTCGA CGGTAGGGTA   320
321  TTGGCCTACC GTGGCAGTGA CGGGTAACGG GGAATTAGGG   360
361  TTCGATTCCG GAGAGGGAGC CTGAGAAACG GCTACCACAT   400
401  CTAAGGAAGG CAGCAGGCGC GCAAATTACC CAATGAAAAC   440
441  AGCTTCGAGG TAGTGACGAG AAATAACAAT ACAGGGCATT   480
481  TTATGCTTTG TAATTGGAAT GATGGAAATG TAAAACCCTT   520
521  CCAGAGTAAC AATTGGAGGG CAAGTCTGGT GCCAGCAGCC   560
561  GCGGTAATTC CGGCTCCAAT AGTGTATATT AGAGTTGTTG   600
601  CAGTTAAAAA GCTCGTAGTT GGATTCTGT CGTGGTCATC    640
641  CGGCGCCGCC CGTATGGGTG TGGGCCTGGC ATGCCCTCGG   680
681  CTTATTTCCG GTAGCCTTCC GCGCTTAATT GCGTGTGTTG   720
721  GTGTTCTGGA ACTTTTACTT TGAGAAAAAT AGAGTGTTTC   760
761  AAGCAGGCTT GTCGCCCTGA ATACTGCAGC ATGGAATAAT   800
801  AAGATAGGAC CTCGGTTCTA TTTTGTTGGT TTCTAGGACC   840
841  AAGGTAATGA TTAATAGGGA CAGTTGGGGG CATTTGTATT   880
881  TAACTGTCAG AGGTGAAATT CTTAGATTTG TTAAAGACGA   920
921  ACTACTGCGA AAGCATTTGC CAAGGATGTT TCATTAATC    960
```

FIG. 5A

```
 961  AAGAACGACA GTAGGGGGTT TGAAGACGAT TAGATACCGT  1000
1001  CGTAATCTCT ACCATAAACT ATGCCGACTA GAGATAGGGA  1040
1041  AACGCCTACC TTGGCTTCTC CTGCACCTCA TGAGAAATCA  1080
1081  AAGTCTCTGG GTTCTGGGGG GAGTATGGTC GCAAGGCTGA  1120
1121  AACTTAAAGG AATTGACGGA GGGGCACCAC CAGGCGTGGA  1160
1161  GCCTGCGGCT TAATTTGACT CAACACGGGG AAACTCACCA  1200
1201  GGTCCAGACA TGGGAAGGAT TGACAGATTG ATAGCTCTTT  1240
1241  CTTGATTCTA TGGGTGGTGG TGCATGGCCG TTCTTAGTTG  1280
1281  GTGGAGTGAT CTGTCTGGTT AATTTCGATA ACGAACGAGA  1320
1321  CCTTAGCCTG CTAAATAGGG TCAGTAACTT CACGATTACT  1360
1361  GTATCACTTC TTAGAGGGAC TTTGCGTGTC TAACGCAAGG  1400
1401  AAGTTTGAGG CAATAACAGG TCTGTGATGC CCTTAGATGT  1440
1441  TCTGGGCTGC ACGCGCGCTA CACTGATGCA TGCAACGAGT  1480
1481  TTTTACCTTG GCCGGCAGGT CTGGGTAATC TTTTGAGTGT  1520
1521  GCGTCGTGAT GGGGATAAAT TATTGCAATT ATTAATCTTC  1560
1561  AACGAGGAAT GCCTAGTAGG CGCAAGTCAG CAGCTTGCGC  1600
1601  CGATTAAGTC CCTGCCTCTT GTACACACCG CCCGTCGCTG  1640
1641  CAACCGATCG GAGGGTCCTG TGAATTCATC GGACGGACAA  1680
1681  GCCTTACTTT GTGGGCTGG  TCGGGAAGTT GCGTAAATAG  1720
1721  AGCCCTCTAA AGGATGCAAA AGTCGTAACA CGGTTT       1756
```

FIG.5B

```
  1  TAGTCATATG CTTGTCTCAA AGATTAAGCC ATGCATGTCT   40
 41  AAGTATAAGC TTTTATACGG TGAAACTGCG AATGGCTCAT   80
 81  TAAAACAGTT ATAGTTTATT TGATGGTCTT TTTTACATGG  120
121  ATAACCATGG TAATTCTATG CTAATACAT ACGCAAAGGC    160
161  TACCTTCTCT GGAGGGGCTG TGTTTATTAG ATACAAAACC  200
201  AACCCACTTT TGTGGAGTCA TGGTGATTCA TAGTAACCGA  240
241  ACGGATCGCA GTTGGCTTTC GGGCCCGCGA TGGATCATTC  280
281  AAGTTTCTGA CCTATCAGCT TTCGACGGTA GGGTATTGGC  320
321  CTACCGTGGC AGTGACGGGT AACGGGGAAT TAGGGTTCGA  360
361  TTCCGGAGAG GGAGCCTGAG AAACGGCTAC CACATCTAAG  400
401  GAAGGCAGCA GGCGCGCAAA TTACCCAATG AAAACAGTTT  440
441  CGAGGTAGTG ACGAGAAATA ACAATACAGG GCATTTATG   480
481  CTTTGTAATT GGAATGATGG GAATGTAAAA CCCTTCCAGA  520
521  GTAACAATTG GAGGGCAAGT CTGGTGCCAG CAGCCGCGGT  560
561  AATTCCAGCT CCAATAGTGT ATATTAGAGT TGTTGCAGTT  600
601  AAAAAGCTCG TAGTTGGATT TCTGTCGTGG TCAGCCTGCG  640
641  CTGCCCGTAT GGGTGTGCGC GTGGTTTGCC CTCGGCATAT  680
681  TTCTGGTAGC CTCTGGCGCT TTATTGCGTT GGTAGGTGTT  720
721  CTGGAACTTT TACTTTGAGA AAATAGAGT GTTTCAAGCA   760
761  GGCTTGTCGC CCTGAATACT GCAGCATGGA ATAATAAGAT  800
801  AGGACCTCGG TTCTATTTTG TTGGTTTCTA GGACCAAGGT  840
841  AATGATTAAT AGGGACAGTT GGGGGCATTC GTATTAACT   880
881  GTCAGAGGTG AAATTCTTAG ATTTGTTAAA GACGAACTAC  920
921  TGCGAAAGCA TTTGCCAAGG ATGTTTTCAT TAATCAAGAA  960
961  CGACAGTAGG GGGTTTGAAG ACGATTAGAT ACCGTCGTAA 1000
```

FIG.6A

```
1001  TCTCTACCAT  AAACTATGCC  GACTAGAGAT  AGGGAAATGC  1040
1041  CTACCTTGGC  TTCTCCTGCA  CCTCATGAGA  AATCAAAGTC  1080
1081  TCTGGGTTCT  GGGGGAGTA   TGGTCGCAAG  GCTGAAACTT  1120
1121  AAAGGAATTG  ACGAGGGGC   ACCACCAGGC  GTGGAGCCTG  1160
1161  CGGCTTAATT  TGACTCAACA  CGGGAAACT   CACCAGGTCC  1200
1201  AGACATGGGA  AGGATTGACA  GATTGATAGC  TCTTTCTTGA  1240
1241  TTCTATGGGT  GGTGGTGCAT  GGCCGTTCTT  AGTTGGTGGA  1280
1281  GTGATCTGTC  TGGTTAATTT  CGATAACGAA  CGAGACCTTG  1320
1321  GCCTGCTAAA  TAGGGTCAGT  AACTTCGGTT  ACTGTATCAC  1360
1361  TTCTTAGAGG  GACTTTACGT  GTCTAACGCA  AGGAAGTTTG  1400
1401  AGGCAATAAC  AGGTCTGTGA  TGCCCTTAGA  TGTTCTGGGC  1440
1441  CGCACGCGCG  CTACACTGAT  GCATGCAACG  AGTTTTTACC  1480
1481  TTGCCCGATG  GGGCTGGGTA  ATCTTGTGAG  GGTGCATCGT  1520
1521  GATGGGGATA  GATTATTGCA  ATTATTAGTC  TTCAACGAGG  1560
1561  AATGCCTAGT  AGGCGCAAGT  CAGCAGCTTG  CGCCGACTAC  1600
1601  GTCCCTGCCC  CTTGTACACA  CCGCCCGTCG  CTGCAACCGA  1640
1641  TCGGAGGGTC  CTGTGAATTC  ATCGGACTGG  CCAACCCCAC  1680
1681  TTTGGGGCTG  GCCGGGAAGT  GCGTAAATA   GAGCCCTCTA  1720
1721  AAGGATGCAA  AAGTCGTAAC  ACGGTTT  1747
```

FIG.6B

| | | | | |
|---|---|---|---|---|
| 1 | TAGTCATATG | CTTGTCTCAA | AGATTAAGCC | ATGCATGTCT | 40 |
| 41 | AAGTATAAGC | TTTTATACGG | TGAAACTGCG | AATGGCTCAT | 80 |
| 81 | TAAAACAGTT | ATAGTTTATT | TGATGGTCTC | ATTTTACATG | 120 |
| 121 | GATAACCATG | GTAATTCTAT | GGCTAATACA | TGCGCAAAGG | 160 |
| 161 | TCACCTCCTT | TGGAGGGGCT | GTGTTTATTA | GATACAAAAC | 200 |
| 201 | CAACCCACTT | TGTAGTGGAG | TCTTGGTGAT | TCATAGTAAC | 240 |
| 241 | CGAACGGATC | GCAGTTGGTT | CTTTGGGCC | CGCGATGGAT | 280 |
| 281 | CATTCAAGTT | TCTGACCTAT | CAGCTTTCGA | CGGTAGGGTA | 320 |
| 321 | TTGGCCTACC | GTGGCAGTGA | CGGGTAACGG | GGAATTAGGG | 360 |
| 361 | TTCGATTCCG | GAGAGGGAGC | CTGAGAAACG | GCTACCACAT | 400 |
| 401 | CTAAGGAAGG | CAGCAGGCGC | GCAAATTACC | CAATGAAAAC | 440 |
| 441 | AGCTTCGAGG | TAGTGACGAG | AAATAACAAT | ACAGGGCATT | 480 |
| 481 | TTATGCTTTG | TAATTGGAAT | GATGGGAATG | TAAAACCCTT | 520 |
| 521 | CCAGAGTAAC | AATTGGAGGG | CAAGTCTGGT | GCCAGCAGCC | 560 |
| 561 | GCGGTAATTC | CAGCTCCAAT | AGTGTATATT | AGAGTTGTTG | 600 |
| 601 | CAGTTAAAAA | GCTCGTAGTT | GGATTTCTGT | CGTGGTCATC | 640 |
| 641 | CGGCGTCGCC | CGTATGGGTG | TGTGCCTGGC | ATGCCCTCGG | 680 |
| 681 | CTTATTTCCG | GTAGCCTTCC | GCGCTTAATT | GCGTGTGTTG | 720 |
| 721 | GTGTTCTGGA | ACTTTTACTT | TGAGAAAAAT | AGAGTGTTTC | 760 |
| 761 | AAGCAGGCTT | GTCGCCCTGA | ATACTGCAGC | ATGGAATAAT | 800 |
| 801 | AAGATAGGAC | CTCGGTTCTA | TTTTGTTGGT | TCTAGGACC | 840 |
| 841 | AAGGTAATGA | TTAATAGGGA | CAGTTGGGGG | CATTCGTATT | 880 |
| 881 | TAACTGTCAG | AGGTGAAATT | CTTAGATTTG | TTAAAGACGA | 920 |
| 921 | ACTACTGCGA | AAGCATTTGC | CAAGGATGTT | TTCATTAATC | 960 |

FIG. 7A

```
 961  AAGAACGACA GTAGGGGGTT TGAAGACGAT TAGATACCGT  1000
1001  CGTAATCTCT ACCATAAACT ATGCCGACTA GAGATAGGGA  1040
1041  AACGCCTACC TTGGCTTCTC CTGCACCTCA TGAGAAATCA  1080
1081  AAGTCTCTGG GTTCTGGGGG GAGTATGGTC GCAAGGCTGA  1120
1121  AACTTAAAGG AATTGACGGA GGGGCACCAC CAGGCGTGGA  1160
1161  GCCTGCGGCT TAATTTGACT CAACACGGGG AAACTCACCA  1200
1201  GGTCCAGACA TGGGAAGGAT TGACAGATTG ATAGCTCTTT  1240
1241  CTTGATTCTA TGGGTGGTGG TGCATGGCCG TTCTTAGTTG  1280
1281  GTGGAGTGAT CTGTCTGGTT AATTTCGATA ACGAACGAGA  1320
1321  CCTTAGCCTG CTAAATAGGG TCAGTAACTT TGCGGTTACT  1360
1361  GTATCACTTC TTAGAGGGAC TTTGCGTGTC TAACGCAAGG  1400
1401  AAGTTTGAGG CAATAACAGG TCTGTGATGC CCTTAGATGT  1440
1441  TCTGGGCTGC ACGCGCGCTA CACTGATGCA TGCAACGAGT  1480
1481  TTTTACCTTG CCGACAGGT CTGGGTAATC TTTTGAGTGT  1520
1521  GCATCGTGAT GGGGATAGAT TATTGCAATT ATTAATCTTC  1560
1561  AACGAGGAAT GCCTAGTAGG CGCAAGTCAG CAGCTTGCGC  1600
1601  CGATTAAGTC CCTGCCTCTT GTACACACCG CCCGTCGCTG  1640
1641  CAACCGATCG GAGGGTCCTG TGAATTCATC GGACGGACAA  1680
1681  GCCTTACTTT GTGGGCTGG TCGGGAAGTT GCGTAAATAG  1720
1721  AGCCCTCTAA AGGATGCAAA AGTCGTAACA CAGTTT       1756
```

FIG. 7B

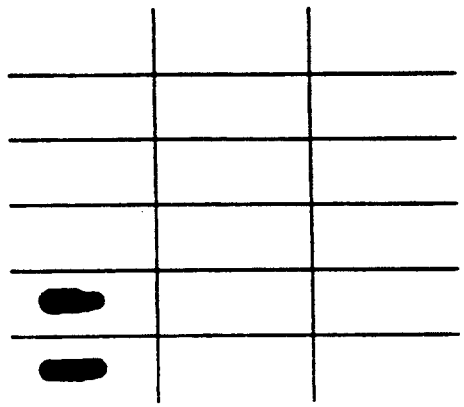
WEp1RC (57°C)
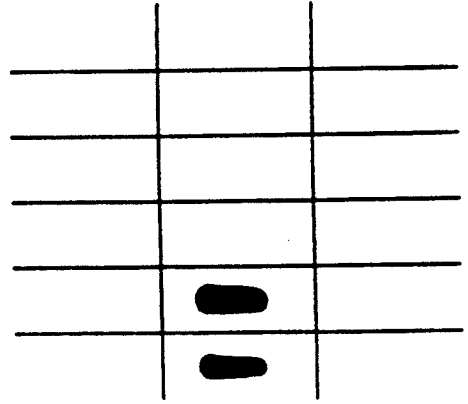
WEmx1RC (55°C)
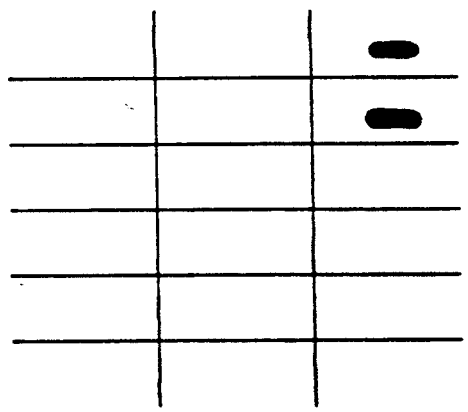
WEn1M (53°C)
| E. TENELLA | E. ACERVULINA | E. NECATRIX |
|---|---|---|
| E. TENELLA | E. ACERVULINA | E. NECATRIX |
| E. TENELLA | E. ACERVULINA | E. BRUNETTI |
| E. TENELLA | E. MITIS | E. BRUNETTI |
| E. PRAECOX | E. MAXIMA | CHICKEN |
| E. PRAECOX | E. MAXIMA | |
FIG.9

|           | 1                |            |            |            |            |
|-----------|------------------|------------|------------|------------|------------|
| Necatrix  | TAGTCATATG       | CTTGTCTCAA | AGATTAAGCC | ATGCATGTCT | AAGTATAAGC |
| Tenella   | TAGTCATATG       | CTTGTCTCAA | AGATTAAGCC | ATGCATGTCT | AAGTATAAGC |
| Acervulina| TAGTCATATG       | CTTGTCTCAA | AGATTAAGCC | ATGCATGTCT | AAGTATAAGC |
| Praecox   | TAGTCATATG       | CTTGTCTCAA | AGATTAAGCC | ATGCATGTCT | AAGTATAAGC |
| Brunetti  | TAGTCATATG       | CTTGTCTCAA | AGATTAAGCC | ATGCATGTCT | AAGTATAAGC |
| Maxima    | TAGTCATATG       | CTTGTCTCAA | AGATTAAGCC | ATGCATGTCT | AAGTATAAAC |
| Mitis     | TAGTCATATG       | CTTGTCTCAA | AGATTAAGCC | ATGCATGTCT | AAGTATAAGC |
| Consensus | TAGTCATATG       | CTTGTCTCAA | AGATTAAGCC | ATGCATGTCT | AAGTATAAGC |

|           |            |            |            |            | 100        |
|-----------|------------|------------|------------|------------|------------|
| Necatrix  | TTTTATACGG | TGAAACTGCG | AATGGCTCAT | TAAAACAGTT | ATAGTTTATT |
| Tenella   | TTTTATACGG | TGAAACTGCG | AATGGCTCAT | TAAAACAGTT | ATAGTTTATT |
| Acervulina| TTTTATACGG | TGAAACTGCG | AATGGCTCAT | TAAAACAGTT | ATAGTTTATT |
| Praecox   | TTTTATACGG | TGAAACTGCG | AATGGCTCAT | TAAAACAGTT | ATAGTTTATT |
| Brunetti  | TTTTATACGG | TGAAACTGCG | AATGGCTCAT | TAAAACAGTT | ATAGTTTATT |
| Maxima    | TTTTATACGG | TGAAACTGCG | AATGGCTCAT | TAAAACAGTT | ATAGTTTATT |
| Mitis     | TTTTATACGG | TGAAACTGCG | AATGGCTCAT | TAAAACAGTT | ATAGTTTATT |
| Consensus | TTTTATACGG | TGAAACTGCG | AATGGCTCAT | TAAAACAGTT | ATAGTTTATT |

FIG.12A

```
          101
Necatrix  TGATGGTCTC ATTTACATG  GATAACCATG GTAATTCTAT GGCTAATACA
Tenella   TGATGGTCTC ATTTACATG  GATAACCATG GTAATTCTAT GGCTAATACA
Acervulina TGATGGTCTC .TTTTACATG GATAACCATG GTAATTCTAT GGCTAATACA
Praecox   TGATGSTCTT .TTTTACATG GATAACCATG GTAATTCTAT GGCTAATACA
Brunetti  TGATGGTCAT .TTTTACATG GATAACCATG GTAATTCTAT GGCTAATACA
Maxima    TGATGGTCTT .TTTTACATG GATAACCATG GTAATTCTAT GGCTAATACA
Mitis     TGATGGTCTT .TTTTACATG GATAACCATG GTAATTCTAT GGCTAATACA
Consensus TGATGGTCTT -TTTTACATG GATAACCATG GTAATTCTAT GGCTAATACA 200
TGCGCAAAGG TCACCTCCTT TGGAGGGGCT TCACCTCCTT GTGTTTATTA GATACAAAAC
TGCGCAAAGG TCACCTCCTT TGGAGGGGCT GTGTTTATTA GATACAAAAC
TGCGCAAGG  CCTCCTCCTC TGGAGGGGCT GTGTTTATTA GATACAAAAC
TRCGCAAARG CYACCTTCTC TGGAGGGGCT GTGTTTATTA GATACAAAAC
TGCGCAAAGG CTTCCTTCTT TGGAAGGGCT GTGTTTATTA GATACAAAAC
TGCGCATAGG CTACCTTCTT TGGAGGAGCT GTGTTTATTA GATACAAAAC
TGCGCAAAAG CCTCCTCCTC TGGAGGGGCT GTGTTTATTA GATACAAAAC
TGCGCAAAGG CCACCTTCTT TGGAGGGGCT GTGTTTATTA GCTACAAAAC
TGCGCAAAGG CCACCTCCTT TGGAGGGGCT GTGTTTATTA GATACAAAAC
```

FIG. 12B

```
           201
Necatrix   CAACCCAC.T TAACGGTGGA GCCTTGGTGA TTCATAGTAA CCGAACGGAT
Tenella    CAACCCAC.T TTGTAGTGGA GTCTTGGTGA TTCATAGTAA CCGAACGGAT
Acervulina CAACCCAC.. CTTGTGTGGA GTCTTGGTGA TTCATAGTAA CCGAACGGAT
Praecox    CAACCCA... CTTTTGTGGA GTCATGGTGA TTCATAGTAA CCGAACGGAT
Brunetti   CAACCCAC.. CT..TGTGGA GCCTTGGTGA TTCATAGTAA CCGAACGGAT
Maxima     CAGCCCACAA TTCTTGTGGA GTCTTGGTGA TTCATAGTAA CCGAACGGAT
Mitis      CAACCCAC.. .TTTTGTGGA GCCTTGGTGA TTCATAGTAA CCGAACGGAT
Consensus  CAACCCAC-- -T-TTGTGGA GTCTTGGTGA TTCATAGTAA CCGAACGGAT 300
           CGAGTTGGT TCTTTTGGAC CCGCGATGGA TCATTCAAGT TTCTGACCTA
           CGAGTTGGT TCTTTTGGGT CCGCGATGGA TCATTCAAGT TTCTGACCTA
           CGAGTTGG. .CTTTCGGGC CCGCGATGGA TCATTCAAGT TTCTGACCTA
           CGAGTTGG. .CTTTCGGGC CCGCGATGGA TCATTCAAGT TTCTGACCTA
           CGAGTTGG. .CTTTCGGGC CCGCGATGGA TCATTCAAGT TTCTGACCTA
           CGAGTTGG. .CTTTCGGGC CCGCGATGGA TCATTCAAGT TTCTGACCTA
           CGAGTTGG. .CTTTCGGGC CCGCGATGGA TCATTCAAGT TTCTGACCTA
           CGAGTTGG- -CTTTCGGGC CCGCGATGGA TCATTCAAGT TTCTGACCTA
```

FIG. 12C

|           | 301        |            |            |            |
|-----------|------------|------------|------------|------------|
| Necatrix  | TCAGCTTTCG | ACGGTAGGGT | ATTGGCCTAC | CGTGGCAGTG | ACGGGTAACG |
| Tenella   | TCAGCTTTCG | ACGGTAGGGT | ATTGGCCTAC | CGTGGCAGTG | ACGGGTAACG |
| Acervulina| TCAGCTTTCG | ACGGTAGGGT | ATTGGCCTAC | CGTGGCAGTG | ACGGGTAACG |
| Praecox   | TCAGCTTTCG | ACGGTAGGGT | ATTGGCCTAC | CGTGGCAGTG | ACGGGTAACG |
| Brunetti  | TCAGCTTTCG | ACGGTAGGGT | ATTGGCCTAC | CGTGGCAGTG | ACGGGTAACG |
| Maxima    | TCAGCTTTCG | ACGGTAGGGT | ATTGGCCTAC | CGTGGCAGTG | ACGGGTAACG |
| Mitis     | TCAGCTTTCG | ACGGTAGGGT | ATTGGCCTAC | CGTGGCAGTG | ACGGGTAACG |
| Consensus | TCAGCTTTCG | ACGGTAGGGT | ATTGGCCTAC | CGTGGCAGTG | ACGGGTAACG |

|           |            |            |            |            | 400        |
|-----------|------------|------------|------------|------------|------------|
| Necatrix  | GGGAATTAGG | GTTCGATTCC | GGAGAGGGAG | CCTGAGAAAC | GGCTACCACA |
| Tenella   | GGGAATTAGG | GTTCGATTCC | GGAGAGGGAG | CCTGAGAAAC | GGCTACCACA |
| Acervulina| GGGAATTAGG | GTTCGATTCC | GGAGAGGGAG | CCTGAGAAAC | GGCTACCACA |
| Praecox   | GGGAATTAGG | GTTCGATTCC | GGAGAGGGAG | CCTGAGAAAC | GGCTACCACA |
| Brunetti  | GGGAATTAGG | GTTCGATTCC | GGAGAGGGAG | CCTGAGAAAC | GGCTACCACA |
| Maxima    | GGGAATTAGG | GTTCGATTCC | GGAGAGGGAG | CCTGAGAAAC | GGCTACCACA |
| Mitis     | GGGAATTAGG | GTTCGATTCC | GGAGAGGGAG | CCTGAGAAAC | GGCTACCACA |
| Consensus | GGGAATTAGG | GTTCGATTCC | GGAGAGGGAG | CCTGAGAAAC | GGCTACCACA |

FIG.12D

|           | 401                                                           |                                                                      |
|-----------|---------------------------------------------------------------|----------------------------------------------------------------------|
| Necatrix  | TCTAAGGAAG GCAGCAGGCG CGCAAATTAC CCAATGAAAA CAGCTTCGAG |
| Tenella   | TCTAAGGAAG GCAGCAGGCG CGCAAATTAC CCAATGAAAA CAGCTTCGAG |
| Acervulina| TCTAAGGAAG GCAGCAGGCG CGCAAATTAC CCAATGAAAA CAGTTTCGAG |
| Praecox   | TCTAAGGAAG GCAGCAGGCG CGCAAATTAC CCAATGAAAA CAGTTTCGAG |
| Brunetti  | TCTAAGGAAG GCAGCAGGCG CGCAAATTAC CCAATGAAAA CAGTTTCGAG |
| Maxima    | TCTAAGGAAG GCAGCAGGCG CGCAAATTAC CCAATGAAAA CAGTTTCGAG |
| Mitis     | TCTAAGGAAG GCAGCAGGCG CGCAAATTAC CCAATGAAAA CAGTTTCGAG |
| Consensus | TCTAAGGAAG GCAGCAGGCG CGCAAATTAC CCAATGAAAA CAGTTTCGAG |

|           |                                                                     500 |
|-----------|-------------------------------------------------------------------------|
| Necatrix  | GTAGTGACGA GAAATAACAA TACAGGGCAT TTTATGCTTT GTAATTGGAA |
| Tenella   | GTAGTGACGA GAAATAACAA TACAGGGCAT TTTATGCTTT GTAATTGGAA |
| Acervulina| GTAGTGACGA GAAATAACAA TAYAGGGCAT TTTATGCTTT GTAATTGGAA |
| Praecox   | GTAGTGACGA GAAATAACAA TACAGGGCAT TTTATGCTTT GTAATTGGAA |
| Brunetti  | GTAGTGACGA GAAATAACAA TACAGGGCAT TTAATGCTTT GTAATTGGAA |
| Maxima    | GTAGTGACGA GAAATAACAA TACAGGGCAT TTTATGCTTT GTAATTGGAA |
| Mitis     | GTAGTGACGA GAAATAACAA TACAGGGCAT TTTATGCTTT GTAATTGGAA |
| Consensus | GTAGTGACGA GAAATAACAA TACAGGGCAT TTTATGCTTT GTAATTGGAA |

FIG.12E

|  | 501 | | | | | |
|---|---|---|---|---|---|---|
| Necatrix | TGATGGRAAT | GTAAAACCCT | TCCAGAGTAA | CAATTGGAGG | GCAAGTCTGG |
| Tenella | TGATGGGAAT | GTAAAACCCT | TCCAGAGTAA | CAATTGGAGG | GCAAGTCTGG |
| Acervulina | TGATGGGAAT | GTAAAACCCT | TCCAGAGTAA | CAATTGGAGG | GCAAGTCTGG |
| Praecox | TGATGGGAAT | GTAAAACCCT | TCCAGAGTAA | CAATTGGAGG | GCAAGTCTGG |
| Brunetti | TGATGGGAAT | GTAAAACCCT | TCCAGAGTAA | CAATTGGAGG | GCAAGTCTGG |
| Maxima | TGATGGGAAT | GTAAAACCCT | TCCAGAGTAA | CAATTGGAGG | GCAAGTCTGG |
| Mitis | TGATGGGAAT | GTAAAACCCT | TCCAGAGTAA | CAATTGGAGG | GCAAGTCTGG |
| Consensus | TGATGGGAAT | GTAAAACCCT | TCCAGAGTAA | CAATTGGAGG | GCAAGTCTGG |

|  |  |  |  |  | 600 |
|---|---|---|---|---|---|
| TGCCAGCAGC | CGCGGTAATT | CCRGCTCCAA | TAGTGTATAT | TAGAGTTGTT |
| TGCCAGCAGC | CGCGGTAATT | CCAGCTCCAA | TAGTGTATAT | TAGAGTTGTT |
| TGCCAGCAGC | CGCGGTAATT | CCAGCTCCAA | TAGTGTATAT | TAGAGTTGTT |
| TGCCAGCAGC | CGCGGTAATT | CCAGCTCCAA | TAGTGTATAT | TAGAGTTGTT |
| TGCCAGCAGC | CGCGGTAATT | CCAGCTCCAA | TAGTGTATAT | TAGAGTTGTT |
| TGCCAGCAGC | CGCGGTAATT | CCAGCTCCAA | TAGTGTATAT | TAGAGTTGTT |
| TGCCAGCAGC | CGCGGTAATT | CCAGCTCCAA | TAGTGTATAT | TAGAGTTGTT |
| TGCCAGCAGC | CGCGGTAATT | CCAGCTCCAA | TAGTGTATAT | TAGAGTTGTT |
| TGCCAGCAGC | CGCGGTAATT | CCAGCTCCAA | TAGTGTATAT | TAGAGTTGTT |

FIG. 12F

```
            601                                                                         700
Necatrix    GCAGTTAAAA AGCTCGTAGT TGGATTTCTG TCGTGGTCAT CCGGCGCCGC   CCGTATGGGT GTGGGCCTGG CATGCCCTCG GCTTATTTCC GGTAGCCTTC
Tenella     GCAGTTAAAA AGCTCGTAGT TGGATTTCTG TCGTGGTCAT CCGGCGTCGC   CCGTATGGGT GTGTGCCTGG CATGCCCTCG GCTTATTTCC GGTAGCCTTC
Acervulina  GCAGTTAAAA AGCTCGTAGT YGGATTTCTG TCGTGGTCAG CCTGCGCTGC   CCGTATGGGT GTGCGCGTGG TTTGCCCTCG GCTTTTTTCT GGTAGCCTCT
Praecox     GCAGTTAAAA AGCTCGTAGT TGGATTTCTG TCGTGGTCAG CCTGCGCTGC   CCGTATGGGT GTGCGCGTGG TTTGCCCTCG GCATATTTCT GGTAGCCTCT
Brunetti    GCAGTTAAAA AGCTCGTAGT TGGATTTCTG TCGTGGTCAG CCTGCGCTGC   CCGTATGGGT GTGCGCGTGG TTTGCCCTCG GCTTTCTTCC GGTAGCCTCC
Maxima      GCAGTTAAAA AGCTCGTAGT TGGATTTCTG TCGTGGTCAG CTTGCGCTGC   CCGTATGGGT GTGCGCGTGG TTTGCCCTCG GCATTCTTCC GGTAGCCTTGT
Mitis       GCAGTTAAAA AGCTCGTAGT TGGATTTCTT CCTGTGCTGC   CCGTATCG.. GTGCACGTGG CTTGCCCTCG ACTTTCTTCC GGTAGCCTCC
Consensus   GCAGTTAAAA AGCTCGTAGT TGGATTTCTG TCGTGGTCAG CCTGCGCTGC   CCGTATGGGT GTGCGCGTGG TTTGCCCTCG GCTTTTTTCC GGTAGCCTCC
```

FIG.12G

```
           701
Necatrix   CGCGCTTAAT TGCGTGTGTT GGTGTTCTGG AACTTTTACT TTGAGAAAAA
Tenella    CGCGCTTAAT TGCGTGTGTT GGTGTTCTGG AACTTTTACT TTGAGAAAAA
Acervulina TGCGCTTAAT TGCGTGGGCT GGTGTTCTGG AACTTTTACT TTGAGAAAAA
Praecox    GGCGCTTAT  TGCGTTGGTA GGTGTTCTGG AACTTTTACT TTGAGAAAAA
Brunetti   GGCTCTTAAT TGCGTCGGTG GGTGTTCTGG AACTTTTACT TTGAGAAAAA
Maxima     GGCGCTTAAT TGCGTCTGCA AGTGCCCTGG AACTTTTACT TTGAGAAAAA
Mitis      TGCGCTTAAT TGCGTGGGCT GGTGTTCTGG AACTTTTACT TTGAGAAAAA
Consensus  -GCGCTTAAT TGCGTGGGTT GGTGTTCTGG AACTTTTACT TTGAGAAAAA 800
TAGAGTGTTT CAAGCAGGCT TGTCGCCCTG AATACTGCAG CATGGAATAA
TAGAGTGTTT CAAGCAGGCT TGTCGCCCTG AATACTGCAG CATGGAATAA
TAGAGTGTTT CAAGCAGGCT TGTCGCCCTG AATACTGCAG CATGGAATAA
TAGAGTGTTT CAAGCAGGCT TGTCGCCCTG AATACTGCAG CATGGAATAA
TAGAGTGTTT CAAGCAGGCT TGTCGCCCTG AATACTGCAG CATGGAATAA
TAGAGTGTTT CAAGCA.GCT TGTCGCCCTG AATACTGCAG CATGGAATAA
TAGAGTGTTT CAAGCAGGCT TGTCGCCCTG AATACTGCAG CATGGAATAA
TAGAGTGTTT CAAGCAGGCT TGTCGCCCTG AATACTGCAG CATGGAATAA
```

FIG. 12H

```
              901
Necatrix    TCTTAGATTT GTTAAAGACG AACTACTGCG AAAGCATTTG CCAAGGATGT
Tenella     TCTTAGATTT GTTAAAGACG AACTACTGCG AAAGCATTTG CCAAGGATGT
Acervulina  TCTTAGATTT GTTAAAGACG AACTACTGCG AAAGCATTTG CCAAGGATGT
Praecox     TCTTAGATTT GTTAAAGACG AACTACTGCG AAAGCATTTG CCAAGGATGT
Brunetti    TCTTAGATTT GTTAAAGACG AACTACTGCG AAAGCATTTG CCAAGGATGT
Maxima      TCTTAGATTT GTTAAAGACG AACTACTGCG AAAGCATTTG CCAAGGATGT
Mitis       TCTTAGATTT GTTAAAGACG AACTACTGCG AAAG..TTTG CCAAGGATGT
Consensus   TCTTAGATTT GTTAAAGACG AACTACTGCG AAAGCATTTG CCAAGGATGT 1000
            TTTCATTAAT CAAGAACGAC AGTAGGGGGT TTGAAGACGA TTAGATACCG
            TTTCATTAAT CAAGAACGAC AGTAGGGGGT TTGAAGACGA TTAGATACCG
            TTTCATTAAT CAAGAACGAC AGTAGGGGGT TTGAAGACGA TTAGATACCG
            TTTCATTAAT CAAGAACGAC AGTAGGGGGT TTGAAGACGA TTAGATACCG
            TTTCATTAAT CAAGAACGAC AGTAGGGGGT TTGAAGACGA TTAGATACCG
            TTTCATTAAT CAAGAACGAC AGTAGGGGGT TTGAAGACGA TTAGATACCG
            TTTCATTAAT CAAGAACGAC AGTAGGGGGT TTGAAGACGA TTAGATACCG
            TTTCATTAAT CAAGAACGAC AGTAGGGGGT TTGAAGACGA TTAGATACCG
```

FIG.12J

|  | 1001 | | | | 1100 | | | |
|---|---|---|---|---|---|---|---|---|
| Necatrix | TCGTAATCTC | TACCATAAAC | TATGCCGACT | AGAGATAGGG | AAACGCCTAC | CTTGGCTTCT | CCTGCACCTC | ATGAGAAATC | AAAGTCTCTG | GGTTCTGGGG |
| Tenella | TCGTAATCTC | TACCATAAAC | TATGCCGACT | AGAGATAGGG | AAACGCCTAC | CTTGGCTTCT | CCTGCACCTC | ATGAGAAATC | AAAGTCTCTG | GGTTCTGGGG |
| Acervulina | TCGTAATCTC | TACCATAAAC | TATGCCGACT | AGAGATAGGG | AAATGCCTAC | CTTGGCTTCT | CCTGCACCTC | ATGAGAAATC | AAAGTCTCTG | GGTTCTGGGG |
| Praecox | TCGTAATCTC | TACCATAAAC | TATGCCGACT | AGAGATAGGG | AAATGCCTAC | CTTGGCTTCT | CCTGCACCTC | ATGAGAAATC | AAAGTCTCTG | GGTTCTGGGG |
| Brunetti | TCGTAATCTC | TACCATAAAC | TATGCCGACT | AGAGATAGGG | AAATGCCTAC | CTTGGCTTCT | CCTGCACCTC | ATGAGAAATC | AAAGTCTCTG | GGTTCTGGGG |
| Maxima | TCGTAATCTC | TACCATAAAC | TATGCCGACT | AGAGATAGGA | AAACGCCTCC | CTTGGCTTCT | CCTGACCCTC | ATGAGAAATC | AAAGTCTCTG | GGTTCTGGGG |
| Mitis | TCGTAATCTC | TACCATAAAC | TATGCCGACT | AGAGATAGGG | AAACGCCTAC | CTTGGCTTCT | CCTGCACCTC | ATGAGAAATC | AAAGTCTCTG | GGTTCTGGGG |
| Consensus | TCGTAATCTC | TACCATAAAC | TATGCCGACT | AGAGATAGGG | AAACGCCTAC | CTTGGCTTCT | CCTGCACCTC | ATGAGAAATC | AAAGTCTCTG | GGTTCTGGGG |

FIG. 12K

|          | 1101       |            |            |            |            |
|----------|------------|------------|------------|------------|------------|
| Necatrix | GGAGTATGGT | CGCAAGGCTG | AAACTTAAAG | GAATTGACGG | AGGGGCACCA |
| Tenella  | GGAGTATGGT | CGCAAGGCTG | AAACTTAAAG | GAATTGACGG | AGGGGCACCA |
| Acervulina | GGAGTATGGT | CGCAAGGCTG | AAACTTAAAG | GAATTGACGG | AGGGGCACCA |
| Praecox  | GGAGTATGGT | CGCAAGGCTG | AAACTTAAAG | GAATTGACGG | AGGGGCACCA |
| Brunetti | GGAGTATGGT | CGCAAGGCTG | AAACTTAAAG | GAATTGACGG | AGGGGCACCA |
| Maxima   | GGAGTATGGT | CGCAAGGCTG | AAACTTAAAG | GAATTGACGG | AGGGGCACCA |
| Mitis    | GGAGTATGGT | CGCAAGGCTG | AAACTTAAAG | GAATTGACGG | AGGGGCACCA |
| Consensus | GGAGTATGGT | CGCAAGGCTG | AAACTTAAAG | GAATTGACGG | AGGGGCACCA |

|          |            |            |            |            | 1200       |
|----------|------------|------------|------------|------------|------------|
| Necatrix | CCAGGCGTGG | AGCCTGCGGC | TTAATTTGAC | TCAACACGGG | GAAACTCACC |
| Tenella  | CCAGGCGTGG | AGCCTGCGGC | TTAATTTGAC | TCAACACGGG | GAAACTCACC |
| Acervulina | CCAGGCGTGG | AGCCTGCGGC | TTAATTTGAC | TCAACACGGG | GAAACTCACC |
| Praecox  | CCAGGCGTGG | AGCCTGCGGC | TTAATTTGAC | TCAACACGGG | GAAACTCACC |
| Brunetti | CCAGGCGTGG | AGCCTGCGGC | TTAATTTGAC | TCAACACGGG | GAAACTCACC |
| Maxima   | CCAGGCGTGG | AG..CTGCGGC | TTAATTTGAC | TCAACACGGG | GAAACTCACC |
| Mitis    | CCAGGCGTGG | AGCCTGCGGC | TTAATTTGAC | TCAACACGGG | GAAACTCACC |
|          | CCAGGCGTGG | AGCC..GGGCC | TTAATTTGAC | TCAACACGGG | GAAACTCACC |
| Consensus | CCAGGCGTGG | AGCCTGCGGC | TTAATTTGAC | TCAACACGGG | GAAACTCACC |

FIG.12L

|           | 1201                                                                                    |
|-----------|-----------------------------------------------------------------------------------------|
| Necatrix  | AGGTCCAGAC ATGGGAAGGA TTGACAGATT GATAGCTCTT TCTTGATTCT |
| Tenella   | AGGTCCAGAC ATGGGAAGGA TTGACAGATT GATAGCTCTT TCTTGATTCT |
| Acervulina| AGGTCCAGAC ATGGGAAGGA TTGACAGATT GATAGCTCTT TCTTGATTCT |
| Praecox   | AGGTCCAGAC ATGGGAAGGA TTGACAGATT GATAGCTCTT TCTTGATTCT |
| Brunetti  | AGGTCCAGAC ATGGGAAGGA TTGACAGATT GATAGCTCTT TCTTGATTCT |
| Maxima    | AGGTCCAGAC ATGGGAAGGA TTGACAGATT GATAGCTCTT TCCTGATTCT |
| Mitis     | AGGTCCAGAC ATGGGAAGGA TTGACAGATT GATAGCTCTT TCTTGATTCT |
| Consensus | AGGTCCAGAC ATGGGAAGGA TTGACAGATT GATAGCTCTT TCTTGATTCT |

|           |                                                                                    1300 |
|-----------|-----------------------------------------------------------------------------------------|
| Necatrix  | ATGGGTGGTG GTGCATGGCC GTTCTTAGTT GGTGGAGTGA TCTGTCTGGT |
| Tenella   | ATGGGTGGTG GTGCATGGCC GTTCTTAGTT GGTGGAGTGA TCTGTCTGGT |
| Acervulina| ATGGGTGGTG GTGCATGGCC GTTCTTAGTT GGTGGAGTGA TCTGTCTGGT |
| Praecox   | ATGGGTGGTG GTGCATGGCC GTTCTTAGTT GGTGGAGTGA TCTGTCTGGT |
| Brunetti  | ATGGGTGGTG GTGCATGGCC GTTCTTAGTT GGTGGAGTGA TCTGTCTGGT |
| Maxima    | ATGGGTGGTG GTGCATGGCC GTTCTTAGTT GGTGGAGTGA TCTGTCTGGT |
| Mitis     | ATGGGTGGTG GTGCATGGCC GTTCTTAGTT GGTGGAGTGA TTTGTCTGGT |
| Consensus | ATGGGTGGTG GTGCATGGCC GTTCTTAGTT GGTGGAGTGA TCTGTCTGGT |

FIG.12M

```
           1301
Necatrix   TAATTTCGAT AACGAACGAG ACCTTAGCCT GCTAAATAGG GTCAGTAACT
Tenella    TAATTTCGAT AACGAACGAG ACCTTAGCCT GCTAAATAGG GTCAGTAACT
Acervulina TAATTTCGAT AACGAACGAG ACCTTGGCCT GCTAAATAGG GTCGGTAACT
Praecox    TAATTTCGAT AACGAACGAG ACCTTGGCCT GCTAAATAGG GTCAGTAACT
Brunetti   TAATTTCGAT AACGAACGAG ACCTTGGCCT GCTAAATAGG GTCGGTGACT
Maxima     TAATTTCGAT AACGAACGAG ACCTTGGCCT GCTAAATAGG GTCGGTGACC
Mitis      TAATTTCGAT AACGAACGAG ACCTTGGCCT GCTAAATAGG GTCGGTGACC
Consensus  TAATTTCGAT AACGAACGAG ACCTTGGCCT GCTAAATAGG GTCGGTAACT 1400
TCA........ CGATTACTGT ATCACTTCTT AGAGGGACTT TGCGTGTCTA
TTG........ CGGTTACTGT ATCACTTCTT AGAGGGACTT TGCGTGTCTA
T.......... CGGTTATCGT ATCACTTCTT AGAGGGACTT TGCGTGTCTA
T.......... CGGTTACTGT ATCACTTCTT AGAGGGACTT TGCGTGTCTA
T.......... TGGTTACCGT ATCGCTTCTT AGAGGGACTT TRCGTGTCTA
T.......... CGGTTACCGT ATCACTTCTT AGAGGGACAT TGCGTGTCTA
CTGGGTCACC AGGTCACCGC ATCGCTTCTT AGAGAACTT TGCGTGTCTA
T--------- CGGTTACCGT ATCACTTCTT AGAGGGACTT TGCGTGTCTA
```

FIG.12N

|           | 1401 |  |  |  |  |
|-----------|------|--|--|--|--|
| Necatrix  | ACGCAAGGAA | GTTTGAGGCA | ATAACAGGTC | TGTGATGCCC | TTAGATGTTC |
| Tenella   | ACGCAAGGAA | GTTTGAGGCA | ATAACAGGTC | TGTGATGCCC | TTAGATGTTC |
| Acervulina| ACGCAAGGAA | GTTTGAGGCA | ATAACAGGTC | TGTGATGCCC | TTAGATGTTC |
| Praecox   | ACGCAAGGAA | GTTYGAGGCA | ATAACAGGTC | TGTGATGCCC | TTAGATGTTC |
| Brunetti  | ACGCAAGGAA | GTTCGAGGCA | ATAACAGGTC | TGTGATGCCC | TTAGATGTTC |
| Maxima    | ACGCAAGGAA | GTTTGAGGCA | ATAACAGGTC | TGTGATGCCC | TTAGATGTTC |
| Mitis     | ACGCAAGGAA | GTTTGAGGCA | ATAACAGGTC | TGTGATGCCC | TTAGATGTTC |
| Consensus | ACGCAAGGAA | GTTTGAGGCA | ATAACAGGTC | TGTGATGCCC | TTAGATGTTC |

|  |  |  |  | 1500 |
|--|--|--|--|------|
| TGGGCTGCAC | GCGCGCTACA | CTGATGCATG | CAACGAGTTT | TTACCTTGGC |
| TGGGCTGCAC | GCGCGCTACA | CTGATGCATG | CAACGAGTTT | TTACCTTGGC |
| TGGGCTGCAC | GCGCGCTACA | CTGATGCATG | CAACGAGTTT | TTACCTTGAC |
| TGGGCCGCAC | GCGCGCTACA | CTGATGCATG | CAACGAGTYT | TTACCTTGCC |
| TGGGCTGCAC | GCGCGCTACA | CTGATGCATG | CAACGAGTTT | TTACCTTGCC |
| TGGGCTGCAC | GCGCGCTACA | CTGATGCATG | CAACGAGTTC | TTACCTTGGC |
| TGGGCTGCAC | GCGCGCTACA | CTGATGCATG | CAACGAGTTT | TCACCTTGTC |
| TGGGCTGCAC | GCGCGCTACA | CTGATGCATG | CAACGAGTTT | TTACCTTGCC |
| TGGGCTGCAC | GCGCGCTACA | CTGATGCATG | CAACGAGTTT | TTACCTTG-C |

FIG.12 O

```
            1501
Necatrix    CGGCAGGTCT GGGTAATCTT TTGAGTGTGC RTCGTGATGG GGATARATTA
Tenella     CGACAGGTCT GGGTAATCTT TTGAGTGTGC ATCGTGATGG GGATAGATTA
Acervulina  CGACGGGGCT GGGTAATCTT CTGAGGGTGC ATCGTGATGG GGATAGATTA
Praecox     CGATGGGGCT GGGTAATCTT GTGAGGGTGC ATCGTGATGG GGATAGATTA
Brunetti    CGACGGGGCT GGGTAATCTT GTGGGGGTGC ATCGTGATGG GGATAGATTA
Maxima      CGATGGGGCT GGGTAATCTT GTGAGGGTGC ATCGTGATGG GGATAGATTA
Mitis       CGATGGGGCT GGGTAATCTT GTGAGGGTGC ATCGTGATGG GGATAGATTA
Consensus   CGACGGGGCT GGGTAATCTT GTGAGGGTGC ATCGTGATGG GGATAGATTA 1600
            TTGCAATTAT TAATCTTCAA CGAGGAATGC CTAGTAGGCG CAAGTCAGCA
            TTGCAATTAT TAATCTTCAA CGAGGAATGC CTAGTAGGCG CAAGTCAGCA
            TTGCAATTAT TAGTCTTCAA CGAGGAATGC CTAGTAGGCG CAAGTCAGCA
            TTGCAATTAT TAGTCTTCAA CGAGGAATGC CTAGTAGGCG CAAGTCAGCA
            TTGCAATTAT TAGTCTTCAA CGAGGAATGC CTAGTAGGCG CAAGTCAGCA
            TTGCAATTAT TAGTCTTCAA CGAGGAATGC CTAGTAGGCG CAAGTCAGCA
            TTGCAATTAT TAGTCTTCAA CGAGGAATGC CTAGTAGGCG CAAGTCAGCA
            TTGCAATTAT TAGTCTTCAA CGAGGAATGC CTAGTAGGCG CAAGTCAGCA
```

FIG. 12P

```
            1601
Necatrix    GCTTGCGCCG ATTAAGTCCC TGCCTCTTGT ACACACCGCC CGTCGCTGCA
Tenella     GCTTGCGCCG ATTAAGTCCC TGCCTCTTGT ACACACCGCC CGTCGCTGCA
Acervulina  GCTTGCGCCG ATTACGTCCC TGCCTCTTGT ACACACCGCC CGTCGCTGCA
Praecox     GCTTGCGCCG ACTACGTCCC YGCCCCTTGT ACACACCGCC CGTCGCTGCA
Brunetti    GCTTGCGCCG ATTACGTCCC TGCCTCTTGT ACACACCGCC CGTCGCTGCA
Maxima      GCTTGTGCCG ATTACGTCCC TGCCTCTTGT ACACACCGCC CGTCGCTGCA
Mitis       GCTTGCGCCG ACTAAGTCCC TGCCTCTTGT ACACACCGCC CGTCGCTGCA
Consensus   GCTTGCGCCG ATTACGTCCC TGCCTCTTGT ACACACCGCC CGTCGCTGCA 1700
Necatrix    ACCGATCGGA GGGTCCTGTG AATTCATCGG ACGGACAAGC CTTACTTTGT
Tenella     ACCGATCGGA GGGTCCTGTG AATTCATCGG ACGGACAAGC CTTACTTTGT
Acervulina  ACCGATCGGA GGGTCCTGTG AATTCATCGG ACTGGCCATT CTCACTT..T
Praecox     ACCGATCGGA GGGTCCTGTG AATTCATCGG ACTGGCCARC CCCACTT..T
Brunetti    ACCGAT.GGA GGGTCCTGTA AATTCATCGG ACTGGCCAAC CCCATTT..T
Maxima      ACCGATCGGA GGGTCCTGTA AATTCATCGG ACTGGCCAAC CCCAACT..T
Mitis       ACCGATCGGA GGGTCCTGTG AATTCATCGG ATGGCCATCC C...CTTCTT
Consensus   ACCGATCGGA GGGTCCTGTG AATTCATCGG ACTG-CCAGC C-CACTT---T
```

FIG.12Q

```
            1701                                                                        1764
Necatrix    GGGGCTGGTC GGGAAGTTGC GTAAATAGAG CCCTCTAAAG GATGCAAAAG TCGTAACACG GTTT
Tenella     GGGGCTGGTC GGGAAGTTGC GTAAATAGAG CCCTCTAAAG GATGCAAAAG TCGTAACACA GTTT
Acervulina  GGGGCTGGCC GGGAAGTTGC GTAAATAGAG CCCTCTAAAG GATGCAAAAG TCGTAACACG GTTT
Praecox     GGGGCTGGCC GGGAAGTTGC GTAAATAGAG CCCTCTAAAG GATGCAAAAG TCGTAACACG GTTT
Brunetti    GGGGCTGGCT GGAAAGTTGC GTAAATAGAG CCCTCTAAAG GATGCAAAAG TCGTAACACG GTTT
Maxima      GGGGCTGGTC GGAAAGTTGC GTAAATAGAG CCCTCTAAAG GATGCAAAAG TCGTAACACG GTTT
Mitis       GGGGCTGGCC GGGAAGTTGC GTAAATAGAG CCCTCTAAAG GATGCAAAAG TCGTAACACG GTTT
Consensus   GGGGCTGGCC GGGAAGTTGC GTAAATAGAG CCCTCTAAAG GATGCAAAAG TCGTAACACG GTTT
```

FIG.12R

|       | I |   |   |   |               |   | II |   |   |       |
|-------|---|---|---|---|---------------|---|----|---|---|-------|
| SLOT #| A | B | C |   |               | A | B  | C |   | SLOT #|
| 1     |   |   |   | — | E. ACERVULINA | —  |   |   |   | 1     |
| 3     |   |   |   | — | E. BRUNETTI   | —  |   |   |   | 3     |
| 5     |   |   |   | — | E. MITIS      | —  |   |   |   | 5     |
|       | 1.24x* | 0.62x | 0.3x |   |          |   |    |   |   |       |
| 7     | ▬ | ▬ | ▬ | — | E. MAXIMA    | —  |   |   |   | 7     |
| 9     |   |   |   | — | E. NECATRIX  | —  |   |   |   | 9     |
|       |   |   |   |   |               | 1.0x* | 0.5x | 0.25x |   |    |
| 11    |   |   |   | — | E. TENELLA   | ▬  | ▬ | — |   | 11    |
| 13    |   |   |   | — | E. PRAECOX   | —  |   |   |   | 13    |
| 15    |   |   |   | — | CHICKEN      | —  |   |   |   | 15    |
| 17    |   |   |   | — | HEPTAVALENT  | —  |   |   |   | 17    |
| 19    | — |   |   | — | HEPTAVALENT  | ▬  |   |   |   | 19    |

\* x10⁶ SPOROCYSTS EQUIVALENT GENOMIC DNA

FIG.16

SEQUENCE LISTING ( 1 ) GENERAL INFORMATION:

( i i i ) NUMBER OF SEQUENCES: 50

( 2 ) INFORMATION FOR SEQ ID NO:1:

( i ) SEQUENCE CHARACTERISTICS:
        ( A ) LENGTH: 19 bases
        ( B ) TYPE: nucleic acid
        ( C ) STRANDEDNESS: single
        ( D ) TOPOLOGY: linear ( x i ) SEQUENCE DESCRIPTION: SEQ ID NO:1:

ACCTGGTTGA TCCTGCCAG    19

( 2 ) INFORMATION FOR SEQ ID NO:2:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( x i ) SEQUENCE DESCRIPTION: SEQ ID NO:2:

CTTCCGCAGG TTCACCTACG G    21

( 2 ) INFORMATION FOR SEQ ID NO:3:

( i ) SEQUENCE CHARACTERISTICS:
        ( A ) LENGTH: 19 bases
        ( B ) TYPE: nucleic acid
        ( C ) STRANDEDNESS: single
        ( D ) TOPOLOGY: linear ( x i ) SEQUENCE DESCRIPTION: SEQ ID NO:3:

TCCCTCTCCG GAATCGGAC    19

( 2 ) INFORMATION FOR SEQ ID NO:4:

( i ) SEQUENCE CHARACTERISTICS:
        ( A ) LENGTH: 16 bases
        ( B ) TYPE: nucleic acid
        ( C ) STRANDEDNESS: single
        ( D ) TOPOLOGY: linear ( x i ) SEQUENCE DESCRIPTION: SEQ ID NO:4:

CCAGGTCCAG ACATGG    16

( 2 ) INFORMATION FOR SEQ ID NO:5:

( i ) SEQUENCE CHARACTERISTICS:
        ( A ) LENGTH: 16 bases
        ( B ) TYPE: nucleic acid
        ( C ) STRANDEDNESS: single
        ( D ) TOPOLOGY: linear ( x i ) SEQUENCE DESCRIPTION: SEQ ID NO:5:

CTTGCGCCTA CTAGGC    16

( 2 ) INFORMATION FOR SEQ ID NO:6:

( i ) SEQUENCE CHARACTERISTICS:
  ( A ) LENGTH: 25 bases
  ( B ) TYPE: nucleic acid
  ( C ) STRANDEDNESS: single
  ( D ) TOPOLOGY: linear ( x i ) SEQUENCE DESCRIPTION: SEQ ID NO:6:

CAGCCCACGC AATTAAGCGC AGGAG 25

( 2 ) INFORMATION FOR SEQ ID NO:7:

( i ) SEQUENCE CHARACTERISTICS:
  ( A ) LENGTH: 23 bases
  ( B ) TYPE: nucleic acid
  ( C ) STRANDEDNESS: single
  ( D ) TOPOLOGY: linear ( x i ) SEQUENCE DESCRIPTION: SEQ ID NO:7:

GAAGTGATAC GATAACCGAA GTT 23

( 2 ) INFORMATION FOR SEQ ID NO:8:

( i ) SEQUENCE CHARACTERISTICS:
  ( A ) LENGTH: 21 bases
  ( B ) TYPE: nucleic acid
  ( C ) STRANDEDNESS: single
  ( D ) TOPOLOGY: linear ( x i ) SEQUENCE DESCRIPTION: SEQ ID NO:8:

CCCCTTCATA GAAAGGAAGC C 21

( 2 ) INFORMATION FOR SEQ ID NO:9:

( i ) SEQUENCE CHARACTERISTICS:
  ( A ) LENGTH: 20 bases
  ( B ) TYPE: nucleic acid
  ( C ) STRANDEDNESS: single
  ( D ) TOPOLOGY: linear ( x i ) SEQUENCE DESCRIPTION: SEQ ID NO:9:

CCCCTTCAAA GAAGGAAGCC 20

( 2 ) INFORMATION FOR SEQ ID NO:10:

( i ) SEQUENCE CHARACTERISTICS:
  ( A ) LENGTH: 16 bases
  ( B ) TYPE: nucleic acid
  ( C ) STRANDEDNESS: single
  ( D ) TOPOLOGY: linear ( x i ) SEQUENCE DESCRIPTION: SEQ ID NO:10:

TGCGTGACCG AGGTCA 16

( 2 ) INFORMATION FOR SEQ ID NO:11:

( i ) SEQUENCE CHARACTERISTICS:
  ( A ) LENGTH: 21 bases
  ( B ) TYPE: nucleic acid
  ( C ) STRANDEDNESS: single
  ( D ) TOPOLOGY: linear ( x i ) SEQUENCE DESCRIPTION: SEQ ID NO:11:

CAAGACTCCA CAAGAATTGT G 21

( 2 ) INFORMATION FOR SEQ ID NO:12:

( i ) SEQUENCE CHARACTERISTICS:
    ( A ) LENGTH: 20 bases
    ( B ) TYPE: nucleic acid
    ( C ) STRANDEDNESS: single
    ( D ) TOPOLOGY: linear ( x i ) SEQUENCE DESCRIPTION: SEQ ID NO:12:

GATACGGTAA CCGAGGTCAC    20

( 2 ) INFORMATION FOR SEQ ID NO:13:

( i ) SEQUENCE CHARACTERISTICS:
        ( A ) LENGTH: 19 bases
        ( B ) TYPE: nucleic acid
        ( C ) STRANDEDNESS: single
        ( D ) TOPOLOGY: linear ( x i ) SEQUENCE DESCRIPTION: SEQ ID NO:13:

CCAGAGGAGG GCCTATGCG    19

( 2 ) INFORMATION FOR SEQ ID NO:14:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( x i ) SEQUENCE DESCRIPTION: SEQ ID NO:14:

CCAGAGGAGG AGGCCTATGC G    21

( 2 ) INFORMATION FOR SEQ ID NO:15:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: linear ( x i ) SEQUENCE DESCRIPTION: SEQ ID NO:15:

TGACCTGGTG ACCCAGG    17

( 2 ) INFORMATION FOR SEQ ID NO:16:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( x i ) SEQUENCE DESCRIPTION: SEQ ID NO:16:

CGTTAAGTGG GTTGGTTTTG    20

( 2 ) INFORMATION FOR SEQ ID NO:17:

( i ) SEQUENCE CHARACTERISTICS:
        ( A ) LENGTH: 24 bases
        ( B ) TYPE: nucleic acid
        ( C ) STRANDEDNESS: single
        ( D ) TOPOLOGY: linear ( x i ) SEQUENCE DESCRIPTION: SEQ ID NO:17:

AAGTGATACA GTAATCGTGA AGTT    24

( 2 ) INFORMATION FOR SEQ ID NO:18:

( i ) SEQUENCE CHARACTERISTICS:
        ( A ) LENGTH: 21 bases
        ( B ) TYPE: nucleic acid
        ( C ) STRANDEDNESS: single (D) TOPOLOGY: linear (xi) SEQUENCE DESCRIPTION: SEQ ID NO:18:

CACCATGACT CCACAAAAGT G　　21

(2) INFORMATION FOR SEQ ID NO:19:

(i) SEQUENCE CHARACTERISTICS:
        (A) LENGTH: 24 bases
        (B) TYPE: nucleic acid
        (C) STRANDEDNESS: single
        (D) TOPOLOGY: linear (xi) SEQUENCE DESCRIPTION: SEQ ID NO:19:

AGAAGTGATA CAGTAACCGA AGTT　　24

(2) INFORMATION FOR SEQ ID NO:20:

(i) SEQUENCE CHARACTERISTICS:
        (A) LENGTH: 21 bases
        (B) TYPE: nucleic acid
        (C) STRANDEDNESS: single
        (D) TOPOLOGY: linear (xi) SEQUENCE DESCRIPTION: SEQ ID NO:20:

CCAAGACTCC ACTACAAAGT G　　21

(2) INFORMATION FOR SEQ ID NO:21:

(i) SEQUENCE CHARACTERISTICS:
        (A) LENGTH: 22 bases
        (B) TYPE: nucleic acid
        (C) STRANDEDNESS: single
        (D) TOPOLOGY: linear (xi) SEQUENCE DESCRIPTION: SEQ ID NO:21:

GTGATACAGT AACCGCAAAG TT　　22

(2) INFORMATION FOR SEQ ID NO:22:

(i) SEQUENCE CHARACTERISTICS:
        (A) LENGTH: 20 bases
        (B) TYPE: nucleic acid
        (C) STRANDEDNESS: single
        (D) TOPOLOGY: linear (xi) SEQUENCE DESCRIPTION: SEQ ID NO:22:

AGCCATTCGC AGTTTCACCG　　20

(2) INFORMATION FOR SEQ ID NO:23:

(i) SEQUENCE CHARACTERISTICS:
        (A) LENGTH: 20 bases
        (B) TYPE: nucleic acid
        (C) STRANDEDNESS: single
        (D) TOPOLOGY: linear (xi) SEQUENCE DESCRIPTION: SEQ ID NO:23:

AAGGTCTCGT TCGTTATCGA　　20

(2) INFORMATION FOR SEQ ID NO:24:

(i) SEQUENCE CHARACTERISTICS:
        (A) LENGTH: 1748 bases
        (B) TYPE: nucleic acid
        (C) STRANDEDNESS: single
        (D) TOPOLOGY: linear (xi) SEQUENCE DESCRIPTION: SEQ ID NO:24:

-continued

| | | | | |
|---|---|---|---|---|
| TAGTCATATG | CTTGTCTCAA | AGATTAAGCC | ATGCATGTCT | 40 |
| AAGTATAAGC | TTTTATACGG | TGAAACTGCG | AATGGCTCAT | 80 |
| TAAAACAGTT | ATAGTTTATT | TGATGGTCTC | TTTTACATGG | 120 |
| ATAACCATGG | TAATTCTATG | GCTAATACAT | GCGCAAGGGC | 160 |
| CTCCTCCTCT | GGAGGGGCTG | TGTTTATTAG | ATACAAAACC | 200 |
| AACCCACCTT | GTGTGGAGTC | TTGGTGATTC | ATAGTAACCG | 240 |
| AACGGATCGC | AGTTGGCTTT | CGGGCCCGCG | ATGGATCATT | 280 |
| CAAGTTTCTG | ACCTATCAGC | TTTCGACGGT | AGGGTATTGG | 320 |
| CCTACCGTGG | CAGTGACGGG | TAACGGGGAA | TTAGGGTTCG | 360 |
| ATTCCGGAGA | GGGAGCCTGA | GAAACGGCTA | CCACATCTAA | 400 |
| GGAAGGCAGC | AGGCGCGCAA | ATTACCCAAT | GAAACAGTT | 440 |
| TCGAGGTAGT | GACGAGAAAT | AACAATACAG | GGCATCTTAT | 480 |
| GCTTTGTAAT | TGGAATGATG | GGAATGTAAA | ACCCTTCCAG | 520 |
| AGTAACAATT | GGAGGGCAAG | TCTGGTGCCA | GCAGCCGCGG | 560 |
| TAATTCCAGC | TCCAATAGTG | TATATTAGAG | TTGTTGCAGT | 600 |
| TAAAAGCTC | GTAGTTGGAT | TTCTGTCGTG | GTCAGCCTGC | 640 |
| GCTGCCCGTA | TGGGTGTGCG | CGTGGTTTGC | CCTCGGCTTT | 680 |
| TTTCTGGTAG | CCTCCTGCGC | TTAATTGCGT | GGGCTGGTGT | 720 |
| TCCGGAACTT | TTACTTTGAG | AAAAATAGAG | TGTTTCAAGC | 760 |
| AGGCTTGTCG | CCCTGAATAC | TGCAGCATGG | AATAATAAGA | 800 |
| TAGGACCTCG | GTTCTATTTT | GTTGGTTTCT | AGGACCAAGG | 840 |
| TAATGATTAA | TAGGACAGT | TGGGGGCATT | CGTATTTAAC | 880 |
| TGTCAGAGGT | GAAATTCTTA | GATTTGTTAA | AGACGAACTA | 920 |
| CTGCGAAAGC | ATTTGCCAAG | GATGTTTTCA | TTAATCAAGA | 960 |
| ACGACAGTAG | GGGGTTTGAA | GACGATTAGA | TACCGTCGTA | 1000 |
| ATCTCTACCA | TAAACTATGC | CGACTAGAGA | TAGGGAAATG | 1040 |
| CCTACCTTGG | CTTCTCCTGC | ACCTCATGAG | AAATCAAAGT | 1080 |
| CTCTGGGTTC | TGGGGGAGT | ATGGTCGCAA | GGCTGAAACT | 1120 |
| TAAAGGAATT | GACGGAGGGG | CACCACCAGG | CGTGGAGCCT | 1160 |
| GCGGCTTAAT | TTGACTCAAC | ACGGGGAAAC | TCACCAGGTC | 1200 |
| CAGACATGGG | AAGGATTGAC | AGATTGATAG | CTCTTTCTTG | 1240 |
| ATTCTATGGG | TGGTGGTGCA | TGGCCGTTCT | TAGTTGGTGG | 1280 |
| AGTGATCTGT | CTGGTTAATT | TCGATAACGA | ACGAGACCTT | 1320 |
| GGCCTGCTAA | ATAGGGTCGG | TAACTTCGGT | TATCGTATCA | 1360 |
| CTTCTTAGAG | GGACTTTGCG | TGTCTAACGC | AAGGAAGTTT | 1400 |
| GAGGCAATAA | CAGGTCTGTG | ATGCCCTTAG | ATGTTCTGGG | 1440 |
| CTGCACGCGC | GCTACACTGA | TGCATGCAAC | GAGTTTTTAC | 1480 |
| CTTGACCGAC | GGGGCTGGGT | AATCTTCTGA | GGGTGCATCG | 1520 |
| TGATGGGGAT | AGATTATTGC | AATTATTAGT | CTTCAACGAG | 1560 |
| GAATGCCTAG | TAGGCGCAAG | TCAGCAGCTT | GCGCCGATTA | 1600 |
| CGTCCCTGCC | TCTTGTACAC | ACCGCCCGTC | GCTGCAACCG | 1640 |

```
ATCGGAGGGT CCTGTGAATT CATCGGACTG GCCATTCTCA    1680

CTTTGGGGCT GGCCGGGAAG TTGCGTAAAT AGAGCCCTCT    1720

AAAGGATGCA AAAGTCGTAA CACGGTTT                 1748
```

( 2 ) INFORMATION FOR SEQ ID NO:25:

( i ) SEQUENCE CHARACTERISTICS:
        ( A ) LENGTH: 1744 bases
        ( B ) TYPE: nucleic acid
        ( C ) STRANDEDNESS: single
        ( D ) TOPOLOGY: linear ( x i ) SEQUENCE DESCRIPTION: SEQ ID NO:25:

```
TAGTCATATG CTTGTCTCAA AGATTAAGCC ATGCATGTCT    40

AAGTATAAAC TTTTATACGG TGAAACTGCG AATGGCTCAT    80

TAAAACAGTT ATAGTTTATT TGATGGTCAT TTTTACATGG    120

ATAACCATGG TAATTCTATG CTAATACAT GCGCATAGGC     160

TTCCTTCTTT GAAGGGGCTG TGTTTATTAG ATACAAAACC    200

AACCCACCTT GTGGAGCCTT GGTGATTCAT AGTAACCGAA    240

CGGATCGCAG TTGGCTTTCG GGCCGCGAT GGATCATTCA     280

AGTTTCTGAC CTATCAGCTT TCGACGGTAG GGTATTGGCC    320

TACCGTGGCA GTGACGGGTA ACGGGGAATT AGGGTTCGAT    360

TCCGGAGAGG GAGCCTGAGA AACGGCTACC ACATCTAAGG    400

AAGGCAGCAG GCGCGCAAAT TACCCAATGA AACAGTTTC     440

GAGGTAGTGA CGAGAAATAA CAATACAGGG CATTTAATGC    480

TTTGTAATTG GAATGATGGG AATGTAAAAC CCTTCCAGAG    520

TAACAATTGG AGGGCAAGTC TGGTGCCAGC AGCCGCGGTA    560

ATTCCAGCTC CAATAGTGTA TATTAGAGTT GTTGCAGTTA    600

AAAAGCTCGT AGTTGGATTT CTGTCGTGGT CAGCCTGCGC    640

TGCCCGTATG GGTGTGCGCG TGGTTTGCCC GCGGCTTTCT    680

TCCGGTAGCC TCCGGCTCTT AATTGCGTCG GTGGGTGTTC    720

TGGAACTTTT ACTTTGAGAA AAATAGAGTG TTTCAAGCAG    760

GCTTGTCGCC CTGAATACTG CAGCATGGAA TAATAAGATA    800

GGACCTCGGT TCTATTTTGT TGGTTTCTAG GACCAAGGTA    840

ATGATTAATA GGGACAGTTG GGGGCATTCG TATTTAACTG    880

TCAGAGGTGA AATTCTTAGA TTTGTTAAAG ACGAACTACT    920

GCGAAAGCAT TTGCCAAGGA TGTTTTCATT AATCAAGAAC    960

GACAGTAGGG GGTTTGAAGA CGATTAGATA CCGTCGTAAT    1000

CTCTACCATA AACTATGCCG ACTAGAGATA GGGAAATGCC    1040

TACCTTGGCT TCTCCTGCAC CTCATGAGAA ATCAAAGTCT    1080

CTGGGTTCTG GGGGAGTAT GGTCGCAAGG CTGAAACTTA     1120

AAGGAATTGA CGGAGGGGCA CCACCAGGCG TGGAGCCTGC    1160

GGCTTAATTT GACTCAACAC GGGGAAACTC ACCAGGTCCA    1200

GACATGGGAA GGATTGACAG ATTGATAGCT CTTTCTTGAT    1240

TCTATGGGTG GTGGTGCATG GCCGTTCTTA GTTGGTGGAG    1280

TGATCTGTCT GGTTAATTTC GATAACGAAC GAGACCTTGG    1320
```

-continued

| | | | | |
|---|---|---|---|---|
| CCTGCTAAAT | AGGGTCGGTG | ACCTCGGTCA | CGCATCGCTT | 1360 |
| CTTAGAGGGA | CTTTGCGTGT | CTAACGCAGG | GAAGTTCGAG | 1400 |
| GCAATAACAG | GTCTGTGATG | CCCTTAGATG | TTCTGGGCTG | 1440 |
| CACGCGCGCT | ACACTGATGC | ATGCAACGAG | TTCTTACCTT | 1480 |
| GGCCGACGGG | GCTGGGTAAT | CTTGTGGGGG | TGCATCGTGA | 1520 |
| TGGGGATAGA | TTATTGCAAT | TATTAGTCTT | CAACGAGGAA | 1560 |
| TGCCTAGTAG | GCGCAAGTCA | GCAGCTTGCG | CCGATTACGT | 1600 |
| CCCTGCCTCT | TGTACACACC | GCCCGTCGCT | GCAACCGATG | 1640 |
| GAGGGTCCTG | TAAATTCATC | GGACTGGCCA | ACCCCATTTT | 1680 |
| GGGGCTGGCT | GGAAAGTTGC | GTAAATAGAG | CCCTCTAAAG | 1720 |
| GATGCAAAAG | TCGTAACACG | GTTT | | 1744 |

( 2 ) INFORMATION FOR SEQ ID NO:26:

( i ) SEQUENCE CHARACTERISTICS:
        ( A ) LENGTH: 1750 bases
        ( B ) TYPE: nucleic acid
        ( C ) STRANDEDNESS: single
        ( D ) TOPOLOGY: linear ( x i ) SEQUENCE DESCRIPTION: SEQ ID NO:26.

| | | | | |
|---|---|---|---|---|
| TAGTCATATG | CTTGTCTCAA | AGATTAAGCC | ATGCATGTCT | 40 |
| AAGTATAAAC | TTTTATACGG | TGAAACTGCG | AATGGCTCAT | 80 |
| TAAAACAGTT | ATAGTTTATT | TGATGGTCTT | TTTTACATGG | 120 |
| ATAACCATGG | TAATTCTATG | GCTAATACAT | GCGCAAAAGC | 160 |
| TACCTTCTTT | GGAGGAGCTG | TGTTTATTAG | ATACAAAACC | 200 |
| AGCCCACAAT | TCTTGTGGAG | TCTTGGTGAT | TCATAGTAAC | 240 |
| CGAACGGATC | GCAGTTGGCT | TTCGGGCCCG | CGATGGATCA | 280 |
| TTCAAGTTTC | TGACCTATCA | GCTTTCGACG | GTAGGGTATT | 320 |
| GGCCTACCGT | GGCAGTGACG | GGTAACGGGG | AATTAGGGTT | 360 |
| CGATTCCGGA | GAGGGAGCCT | GAGAAACGGC | TACCACATCT | 400 |
| AAGGAAGGCA | GCAGGCGCGC | AAATTACCCA | ATGAAAACAG | 440 |
| TTTCGAGGTA | GTGACGAGAA | ATAACAATAC | AGGGCATTTT | 480 |
| ATGCTTTGTA | ATTGGAATGA | TGGGAATGTA | AAACCCTTCC | 520 |
| AGAGTAACAA | TTGGAGGGCA | AGTCTGGTGC | CAGCAGCCGC | 560 |
| GGTAATTCCA | GCTCCAATAG | TGTATATTAG | AGTTGTTGCA | 600 |
| GTTAAAAAGC | TCGTAGTTGG | ATTTCTGTCG | TGGTCAGCTT | 640 |
| GCGCTGCCCG | TATGGGTGTG | CGCGTGGTTT | GCCCTCGGCA | 680 |
| TTCTTCCGGT | AGCTTGTGGC | GCTTAATTGC | GTCTGCAAGT | 720 |
| GCCCTGGAAC | TTTTACTTTG | AGAAAAATAG | AGTGTTTCAA | 760 |
| GCAGGCTTGT | CGCCCTGAAT | ACTGCAGCAT | GGAATAATAG | 800 |
| GATAGGACCT | CGGTTCTATT | TTGTTGGTTT | CTAGGACCAA | 840 |
| GGTAATGATT | AATAGGGACA | GTTGGGGCA | TTCGTATTTA | 880 |
| ACTGTCAGAG | GTGAAATTCT | TAGATTTGTT | AAAGACGAAC | 920 |
| TACTGCGAAA | GCATTTGCCA | AGGATGTTTT | CATTAATCAA | 960 |

| | | | | |
|---|---|---|---|---|
| GAACGACAGT | AGGGGGTTTG | AAGACGATTA | GATACCGTCG | 1000 |
| TAATCTCTAC | CATAAACTAT | GCCGACTAGA | GATAGGAAAA | 1040 |
| CGCCTCCCTT | GGCTTCTCCT | GGACCTCATG | AGAAATCAAA | 1080 |
| GTCTCTGGGT | TCTGGGGGGA | GTATGGTCGC | AAGGCTGAAA | 1120 |
| CTTAAAGGAA | TTGACGGAGG | GGCACCACCA | GGCGTGGAGC | 1160 |
| CTGCGGCTTA | ATTTGACTCA | ACACGGGGAA | ACTCACCAGG | 1200 |
| TCCAGACATG | GGAAGGATTG | ACAGATTGAT | AGCTCTTTCC | 1240 |
| TGATTCTATG | GGTGGTGGTG | CATGGCCGTT | CTTAGTTGGT | 1280 |
| GGAGTGATTT | GTCTGGTTAA | TTTCGATAAC | GAACGAGACC | 1320 |
| TTGGCCTGCT | AAATAGGGTC | GGTGACCTCG | GTTACCGTAT | 1360 |
| CACTTCTTAG | AGGGACATTG | CGTGTCTAAC | GCAAGGAAGT | 1400 |
| TTGAGGCAAT | AACAGGTCTG | TGATGCCCTT | AGATGTTCTG | 1440 |
| GGCTGCACGC | GCGCTACACT | GATGCATGCA | ACGAGTTTTC | 1480 |
| ACCTTGTCCG | ATGGGGCTGG | GTAATCTTGT | GAGGGTGCAT | 1520 |
| CGTGATGGGG | ATAGATTATT | GCAATTATTA | GTCTTCAACG | 1560 |
| AGGAATGCCT | AGTAGGCGCA | AGTCAGCAGC | TTGTGCCGAT | 1600 |
| TACGTCCCTG | CCTCTTGTAC | ACACCGCCCG | TCGCTGCAAC | 1640 |
| CGATCGGAGG | GTCCTGTAAA | TTCATCGGAC | TGACCAGCCC | 1680 |
| CAACTTGGGG | CTGGTCGGAA | AGTTGCGTAA | ATAGAGCCCT | 1720 |
| CTAAAGGATG | CAAAAGTCGT | AACACGGTTT | | 1750 |

( 2 ) INFORMATION FOR SEQ ID NO:27:

( i ) SEQUENCE CHARACTERISTICS:
        ( A ) LENGTH: 1749 bases
        ( B ) TYPE: nucleic acid
        ( C ) STRANDEDNESS: single
        ( D ) TOPOLOGY: linear ( x i ) SEQUENCE DESCRIPTION: SEQ ID NO:27:

| | | | | |
|---|---|---|---|---|
| TAGTCATATG | CTTGTCTCAA | AGATTAAGCC | ATGCATGTCT | 40 |
| AAGTATAAGC | TTTTATACGG | TGAAACTGCG | AATGGCTCAT | 80 |
| TAAAACAGTT | ATAGTTTATT | TGATGGTCTT | TTTTACATGG | 120 |
| ATAACCATGG | TAATTCTATG | GCTAATACAT | GCGCATAGGC | 160 |
| CTCCTCCTCT | GGAGGGGCTG | TGTTTATTAG | CTACAAAACC | 200 |
| AACCCACTTT | TGTGGAGCCT | TGGTGATTCA | TAGTAACCGA | 240 |
| ACGGATCGCA | GTTGGCTTTC | GGGCCCGCGA | TGGATCATTC | 280 |
| AAGTTTCTGA | CCTATCAGCT | TTCGACGGTA | GGGTATTGGC | 320 |
| CTACCGTGGC | AGTGACGGGT | AACGGGGAAT | TAGGGTTCGA | 360 |
| TTCCGGAGAG | GGAGCCTGAG | AAACGGCTAC | CACATCTAAG | 400 |
| GAAGGCAGCA | GGCGCGCAAA | TTACCCAATG | AAAACAGTTT | 440 |
| CGAGGTAGTG | ACGAGAAATA | ACAATACAGG | GCATTTTATG | 480 |
| CTTTGTAATT | GGAATGATGG | GAATGTAAAA | CCCTTCCAGA | 520 |
| GTAACAATTG | GAGGGCAAGT | CTGGTGCCAG | CAGCCGCGGT | 560 |
| AATTCCAGCT | CCAATAGTGT | ATATTAGAGT | TGTTGCAGTT | 600 |
| AAAAAGCTCG | TAGTTGGATT | TCTGTCGTGG | TCTTCCTGTG | 640 |

| | | | | |
|---|---|---|---|---|
| CTGCCCGTAT | CGGTGCACGT | GGCTTGCCCT | CGACTTTCTT | 680 |
| CCGGTAGCCT | CCTGCGCTTC | ACTGCGTGGG | CTGGTGTTCT | 720 |
| GGAACTTTTA | CTTTGAGAAA | AATAGAGTGT | TTCAAGCAGC | 760 |
| TTGTCGCCCT | GAATACTGCA | GCATGGAATA | ATAAGATAGG | 800 |
| ACCTCGGTTC | TATTTGTTG | GTTTCTAGGA | CCAAGGTAAT | 840 |
| GATTAATAGG | GACAGTTGGG | GGCATTCGTA | TTTAACTGTC | 880 |
| AGAGGTGAAA | TTCTTAGATT | TGTTAAAGAC | GAACTACTGC | 920 |
| GAAAGTTTGC | CAAGGATGTT | TTCATTAATC | AAGAACGACA | 960 |
| GTAGGGGGTT | TGAAGACGAT | TAGATACCGT | CGTAATCTCT | 1000 |
| ACCATAAACT | ATGCCGACTA | GAGATAGGGA | AACGCCTACC | 1040 |
| TTGGCTTCTC | CTGCACCTCA | TGAGAAATCA | AGTCTCTGG | 1080 |
| GTTCTGGGGG | GAGTATGGTC | GCAAGGCTGA | AACTTAAAGG | 1120 |
| AATTGACGGA | GGGGCACCAC | CAGGCGTGGA | GCCGGGCCTT | 1160 |
| AATTTGACTC | AACACGGGGA | AACTCACCAG | GTCCAGACAT | 1200 |
| GGGAAGGATT | GACAGATTGA | TAGCTCTTTC | TTGATTCTAT | 1240 |
| GGGTGGTGGT | GCATGGCCGT | TCTTAGTTGG | TGGAGTGATC | 1280 |
| TGTCTGGTTA | ATTTCGATAA | CGAACGAGAC | CTTGGCCTGC | 1320 |
| TAAATAGGGT | CGGTGACCCT | GGGTCACCAG | GTCACCGCAT | 1360 |
| CGCTTCTTAG | AGGAACTTTG | CGTGTCTAAC | GCAAGGAAGT | 1400 |
| TTGAGGCAAT | AACAGGTCTG | TGATGCCCTT | AGATGTTCTG | 1440 |
| GGCTGCACGC | GCGCTACACT | GATGCATGCA | ACGAGTTTTT | 1480 |
| ACCTTGCCCG | ATGGGCGTGG | GTAATCTTGT | GAGGGTGCAT | 1520 |
| CGTGATGGGG | ATAGATTATT | GCAATTATTA | GTCTTCAACG | 1560 |
| AGGAATGCCT | AGTAGGCGCA | AGTCAGCAGC | TTGCGCCGAC | 1600 |
| TAAGTCCCTG | CCTCTTGTAC | ACACCGCCCG | TCGCTGCAAC | 1640 |
| CGATCGGAGG | GTCCTGTGAA | TTCATCGGAT | GGCCATCCCC | 1680 |
| TTCTTGGGGC | TGGCCGGGAA | GTTGCGTAAA | TAGAGCCCTC | 1720 |
| TAAAGGATGC | AAAAGTCGTA | ACACGGTTT | | 1749 |

( 2 ) INFORMATION FOR SEQ ID NO:28:

( i ) SEQUENCE CHARACTERISTICS:
    ( A ) LENGTH: 1756 bases
    ( B ) TYPE: nucleic acid
    ( C ) STRANDEDNESS: single
    ( D ) TOPOLOGY: linear ( x i ) SEQUENCE DESCRIPTION: SEQ ID NO:28:

| | | | | |
|---|---|---|---|---|
| TAGTCATATG | CTTGTCTCAA | AGATTAAGCC | ATGCATGTCT | 40 |
| AAGTATAAGC | TTTTATACGG | TGAAACTGCG | AATGGCTCAT | 80 |
| TAAAACAGTT | ATAGTTTATT | TGATGGTCTC | ATTTTACATG | 120 |
| GATAACCATG | GTAATTCTAT | GGCTAATACA | TGCGCAAAGG | 160 |
| TCACCTCCTT | TGGAGGGGCT | GTGTTTATTA | GATACAAAAC | 200 |
| CAACCCACTT | AACGGTGGAG | CCTTGGTGAT | TCATAGTAAC | 240 |
| CGAACGGATC | GCAGTTGGTT | CTTTTGGACC | CGCGATGGAT | 280 |

```
CATTCAAGTT  TCTGACCTAT  CAGCTTTCGA  CGGTAGGGTA      320
TTGGCCTACC  GTGGCAGTGA  CGGGTAACGG  GGAATTAGGG      360
TTCGATTCCG  GAGAGGGAGC  CTGAGAAACG  GCTACCACAT      400
CTAAGGAAGG  CAGCAGGCGC  GCAAATTACC  CAATGAAAAC      440
AGCTTCGAGG  TAGTGACGAG  AAATAACAAT  ACAGGGCATT      480
TTATGCTTTG  TAATTGGAAT  GATGGAAATG  TAAAACCCTT      520
CCAGAGTAAC  AATTGGAGGG  CAAGTCTGGT  GCCAGCAGCC      560
GCGGTAATTC  CGGCTCCAAT  AGTGTATATT  AGAGTTGTTG      600
CAGTTAAAAA  GCTCGTAGTT  GGATTTCTGT  CGTGGTCATC      640
CGGCGCCGCC  CGTATGGGTG  TGGGCCTGGC  ATGCCCTCGG      680
CTTATTTCCG  GTAGCCTTCC  GCGCTTAATT  GCGTGTGTTG      720
GTGTTCTGGA  ACTTTTACTT  TGAGAAAAAT  AGAGTGTTTC      760
AAGCAGGCTT  GTCGCCCTGA  ATACTGCAGC  ATGGAATAAT      800
AAGATAGGAC  CTCGGTTCTA  TTTTGTTGGT  TTCTAGGACC      840
AAGGTAATGA  TTAATAGGGA  CAGTTGGGGG  CATTTGTATT      880
TAACTGTCAG  AGGTGAAATT  CTTAGATTTG  TTAAAGACGA      920
ACTACTGCGA  AAGCATTTGC  CAAGGATGTT  TTCATTAATC      960
AAGAACGACA  GTAGGGGGTT  TGAAGACGAT  TAGATACCGT     1000
CGTAATCTCT  ACCATAAACT  ATGCCGACTA  GAGATAGGGA     1040
AACGCCTACC  TTGGCTTCTC  CTGCACCTCA  TGAGAAATCA     1080
AAGTCTCTGG  GTTCTGGGGG  GAGTATGGTC  GCAAGGCTGA     1120
AACTTAAAGG  AATTGACGGA  GGGGCACCAC  CAGGCGTGGA     1160
GCCTGCGGCT  TAATTTGACT  CAACACGGGG  AAACTCACCA     1200
GGTCCAGACA  TGGGAAGGAT  TGACAGATTG  ATAGCTCTTT     1240
CTTGATTCTA  TGGGTGGTGG  TGCATGGCCG  TTCTTAGTTG     1280
GTGGAGTGAT  CTGTCTGGTT  AATTTCGATA  ACGAACGAGA     1320
CCTTAGCCTG  CTAAATAGGG  TCAGTAACTT  CACGATTACT     1360
GTATCACTTC  TTAGAGGGAC  TTTGCGTGTC  TAACGCAAGG     1400
AAGTTTGAGG  CAATAACAGG  TCTGTGATGC  CCTTAGATGT     1440
TCTGGGCTGC  ACGCGCGCTA  CACTGATGCA  TGCAACGAGT     1480
TTTTACCTTG  GCCGGCAGGT  CTGGGTAATC  TTTTGAGTGT     1520
GCGTCGTGAT  GGGGATAAAT  TATTGCAATT  ATTAATCTTC     1560
AACGAGGAAT  GCCTAGTAGG  CGCAAGTCAG  CAGCTTGCGC     1600
CGATTAAGTC  CCTGCCTCTT  GTACACACCG  CCCGTCGCTG     1640
CAACCGATCG  GAGGGTCCTG  TGAATTCATC  GGACGGACAA     1680
GCCTTACTTT  GTGGGGCTGG  TCGGGAAGTT  GCGTAAATAG     1720
AGCCCTCTAA  AGGATGCAAA  AGTCGTAACA  CGGTTT         1756
```

( 2 ) INFORMATION FOR SEQ ID NO:29:

( i ) SEQUENCE CHARACTERISTICS:
        ( A ) LENGTH: 1747 bases
        ( B ) TYPE: nucleic acid
        ( C ) STRANDEDNESS: single
        ( D ) TOPOLOGY: linear ( x i ) SEQUENCE DESCRIPTION: SEQ ID NO:29:

```
TAGTCATATG CTTGTCTCAA AGATTAAGCC ATGCATGTCT      40
AAGTATAAGC TTTTATACGG TGAAACTGCG AATGGCTCAT      80
TAAAACAGTT ATAGTTTATT TGATGGTCTT TTTTACATGG     120
ATAACCATGG TAATTCTATG GCTAATACAT ACGCAAAGGC     160
TACCTTCTCT GGAGGGGCTG TGTTTATTAG ATACAAAACC     200
AACCCACTTT TGTGGAGTCA TGGTGATTCA TAGTAACCGA     240
ACGGATCGCA GTTGGCTTTC GGGCCCGCGA TGGATCATTC     280
AAGTTTCTGA CCTATCAGCT TTCGACGGTA GGGTATTGGC     320
CTACCGTGGC AGTGACGGGT AACGGGGAAT TAGGGTTCGA     360
TTCCGGAGAG GGAGCCTGAG AAACGGCTAC CACATCTAAG     400
GAAGGCAGCA GGCGCGCAAA TTACCCAATG AAAACAGTTT     440
CGAGGTAGTG ACGAGAAATA ACAATACAGG GCATTTTATG     480
CTTTGTAATT GGAATGATGG GAATGTAAAA CCCTTCCAGA     520
GTAACAATTG GAGGGCAAGT CTGGTGCCAG CAGCCGCGGT     560
AATTCCAGCT CCAATAGTGT ATATTAGAGT TGTTGCAGTT     600
AAAAGCTCG  TAGTTGGATT TCTGTCGTGG TCAGCCTGCG     640
CTGCCCGTAT GGGTGTGCGC GTGGTTTGCC CTCGGCATAT     680
TTCTGGTAGC CTCTGGCGCT TTATTGCGTT GGTAGGTGTT     720
CTGGAACTTT TACTTTGAGA AAAATAGAGT GTTTCAAGCA     760
GGCTTGTCGC CCTGAATACT GCAGCATGGA ATAATAAGAT     800
AGGACCTCGG TTCTATTTTG TTGGTTTCTA GGACCAAGGT     840
AATGATTAAT AGGGACAGTT GGGGGCATTC GTATTTAACT     880
GTCAGAGGTG AAATTCTTAG ATTTGTTAAA GACGAACTAC     920
TGCGAAAGCA TTTGCCAAGG ATGTTTTCAT TAATCAAGAA     960
CGACAGTAGG GGGTTTGAAG ACGATTAGAT ACCGTCGTAA    1000
TCTCTACCAT AAACTATGCC GACTAGAGAT AGGGAAATGC    1040
CTACCTTGGC TTCTCCTGCA CCTCATGAGA AATCAAAGTC    1080
TCTGGGTTCT GGGGGGAGTA TGGTCGCAAG GCTGAAACTT    1120
AAAGGAATTG ACGGAGGGGC ACCACCAGGC GTGGAGCCTG    1160
CGGCTTAATT TGACTCAACA CGGGGAAACT CACCAGGTCC    1200
AGACATGGGA AGGATTGACA GATTGATAGC TCTTTCTTGA    1240
TTCTATGGGT GGTGGTGCAT GGCCGTTCTT AGTTGGTGGA    1280
GTGATCTGTC TGGTTAATTT CGATAACGAA CGAGACCTTG    1320
GCCTGCTAAA TAGGGTCAGT AACTTCGGTT ACTGTATCAC    1360
TTCTTAGAGG GACTTTACGT GTCTAACGCA AGGAAGTTTG    1400
AGGCAATAAC AGGTCTGTGA TGCCCTTAGA TGTTCTGGGC    1440
CGCACGCGCG CTACACTGAT GCATGCAACG AGTTTTTACC    1480
TTGCCCGATG GGCTGGGTA  ATCTTGTGAG GGTGCATCGT    1520
GATGGGGATA GATTATTGCA ATTATTAGTC TTCAACGAGG    1560
AATGCCTAGT AGGCGCAAGT CAGCAGCTTG CGCCGACTAC    1600
```

| | | | | |
|---|---|---|---|---|
| GTCCCTGCCC | CTTGTACACA | CCGCCCGTCG | CTGCAACCGA | 1640 |
| TCGGAGGGTC | CTGTGAATTC | ATCGGACTGG | CCAACCCCAC | 1680 |
| TTTGGGGCTG | GCCGGGAAGT | TGCGTAAATA | GAGCCCTCTA | 1720 |
| AAGGATGCAA | AAGTCGTAAC | ACGGTTT | | 1747 |

( 2 ) INFORMATION FOR SEQ ID NO:30:

( i ) SEQUENCE CHARACTERISTICS:
        ( A ) LENGTH: 1756 bases
        ( B ) TYPE: nucleic acid
        ( C ) STRANDEDNESS: single
        ( D ) TOPOLOGY: linear ( x i ) SEQUENCE DESCRIPTION: SEQ ID NO:30:

| | | | | |
|---|---|---|---|---|
| TAGTCATATG | CTTGTCTCAA | AGATTAAGCC | ATGCATGTCT | 40 |
| AAGTATAAGC | TTTTATACGG | TGAAACTGCG | AATGGCTCAT | 80 |
| TAAAACAGTT | ATAGTTTATT | TGATGGTCTC | ATTTTACATG | 120 |
| GATAACCATG | GTAATTCTAT | GGCTAATACA | TGCGCAAAGG | 160 |
| TCACCTCCTT | TGGAGGGGCT | GTGTTTATTA | GATACAAAAC | 200 |
| CAACCCACTT | TGTAGTGGAG | TCTTGGTGAT | TCATAGTAAC | 240 |
| CGAACGGATC | GCAGTTGGTT | CTTTTGGGCC | CGCGATGGAT | 280 |
| CATTCAAGTT | TCTGACCTAT | CAGCTTTCGA | CGGTAGGGTA | 320 |
| TTGGCCTACC | GTGGCAGTGA | CGGGTAACGG | GGAATTAGGG | 360 |
| TTCGATTCCG | GAGAGGGAGC | CTGAGAAACG | GCTACCACAT | 400 |
| CTAAGGAAGG | CAGCAGGCGC | GCAAATTACC | CAATGAAAAC | 440 |
| AGCTTCGAGG | TAGTGACGAG | AAATAACAAT | ACAGGGCATT | 480 |
| TTATGCTTTG | TAATTGGAAT | GATGGGAATG | TAAAACCCTT | 520 |
| CCAGAGTAAC | AATTGGAGGG | CAAGTCTGGT | GCCAGCAGCC | 560 |
| GCGGTAATTC | CAGCTCCAAT | AGTGTATATT | AGAGTTGTTG | 600 |
| CAGTTAAAAA | GCTCGTAGTT | GGATTTCTGT | CGTGGTCATC | 640 |
| CGGCGTCGCC | CGTATGGGTG | TGTGCCTGGC | ATGCCCTCGG | 680 |
| CTTATTTCCG | GTAGCCTTCC | GCGCTTAATT | GCGTGTGTTG | 720 |
| GTGTTCTGGA | ACTTTTACTT | TGAGAAAAAT | AGAGTGTTTC | 760 |
| AAGCAGGCTT | GTCGCCCTGA | ATACTGCAGC | ATGGAATAAT | 800 |
| AAGATAGGAC | CTCGGTTCTA | TTTTGTTGGT | TTCTAGGACC | 840 |
| AAGGTAATGA | TTAATAGGGA | CAGTTGGGGG | CATTCGTATT | 880 |
| TAACTGTCAG | AGGTGAAATT | CTTAGATTTG | TTAAAGACGA | 920 |
| ACTACTGCGA | AAGCATTTGC | CAAGGATGTT | TTCATTAATC | 960 |
| AAGAACGACA | GTAGGGGGTT | TGAAGACGAT | TAGATACCGT | 1000 |
| CGTAATCTCT | ACCATAAACT | ATGCCGACTA | GAGATAGGGA | 1040 |
| AACGCCTACC | TTGGCTTCTC | CTGCACCTCA | TGAGAAATCA | 1080 |
| AAGTCTCTGG | GTTCTGGGGG | GAGTATGGTC | GCAAGGCTGA | 1120 |
| AACTTAAAGG | AATTGACGGA | GGGGCACCAC | CAGGCGTGGA | 1160 |
| GCCTGCGGCT | TAATTTGACT | CAACACGGGG | AAACTCACCA | 1200 |
| GGTCCAGACA | TGGGAAGGAT | TGACAGATTG | ATAGCTCTTT | 1240 |

|      |      |      |      |      |
|---|---|---|---|---|
| CTTGATTCTA | TGGGTGGTGG | TGCATGGCCG | TTCTTAGTTG | 1280 |
| GTGGAGTGAT | CTGTCTGGTT | AATTTCGATA | ACGAACGAGA | 1320 |
| CCTTAGCCTG | CTAAATAGGG | TCAGTAACTT | TGCGGTTACT | 1360 |
| GTATCACTTC | TTAGAGGGAC | TTTGCGTGTC | TAACGCAAGG | 1400 |
| AAGTTTGAGG | CAATAACAGG | TCTGTGATGC | CCTTAGATGT | 1440 |
| TCTGGGCTGC | ACGCGCGCTA | CACTGATGCA | TGCAACGAGT | 1480 |
| TTTTACCTTG | GCCGACAGGT | CTGGGTAATC | TTTTGAGTGT | 1520 |
| GCATCGTGAT | GGGGATAGAT | TATTGCAATT | ATTAATCTTC | 1560 |
| AACGAGGAAT | GCCTAGTAGG | CGCAAGTCAG | CAGCTTGCGC | 1600 |
| CGATTAAGTC | CCTGCCTCTT | GTACACACCG | CCCGTCGCTG | 1640 |
| CAACCGATCG | GAGGGTCCTG | TGAATTCATC | GGACGGACAA | 1680 |
| GCCTTACTTT | GTGGGGCTGG | TCGGGAAGTT | GCGTAAATAG | 1720 |
| AGCCCTCTAA | AGGATGCAAA | AGTCGTAACA | CAGTTT | 1756 |

( 2 ) INFORMATION FOR SEQ ID NO:31:

( i ) SEQUENCE CHARACTERISTICS:
        ( A ) LENGTH: 16 bases
        ( B ) TYPE: nucleic acid
        ( C ) STRANDEDNESS: single
        ( D ) TOPOLOGY: linear ( x i ) SEQUENCE DESCRIPTION: SEQ ID NO:31:

GTCGCAAGGC TGAAAC    16

( 2 ) INFORMATION FOR SEQ ID NO:32:

( i ) SEQUENCE CHARACTERISTICS:
        ( A ) LENGTH: 16 bases
        ( B ) TYPE: nucleic acid
        ( C ) STRANDEDNESS: single
        ( D ) TOPOLOGY: linear ( x i ) SEQUENCE DESCRIPTION: SEQ ID NO:32:

CTTGCGCCTA CTAGGC    16

( 2 ) INFORMATION FOR SEQ ID NO:33:

( i ) SEQUENCE CHARACTERISTICS:
        ( A ) LENGTH: 23 bases
        ( B ) TYPE: nucleic acid
        ( C ) STRANDEDNESS: single
        ( D ) TOPOLOGY: linear ( x i ) SEQUENCE DESCRIPTION: SEQ ID NO:33:

GGGGGGAGTA TGGTCTGCAA GGC    23

( 2 ) INFORMATION FOR SEQ ID NO:34:

( i ) SEQUENCE CHARACTERISTICS:
        ( A ) LENGTH: 23 bases
        ( B ) TYPE: nucleic acid
        ( C ) STRANDEDNESS: single
        ( D ) TOPOLOGY: linear ( x i ) SEQUENCE DESCRIPTION: SEQ ID NO:34:

GCATGCATCA GTGTAGCTGC GCG    23

( 2 ) INFORMATION FOR SEQ ID NO:35:

( i ) SEQUENCE CHARACTERISTICS:

( A ) LENGTH: 20 bases
( B ) TYPE: nucleic acid
( C ) STRANDEDNESS: single
( D ) TOPOLOGY: linear ( x i ) SEQUENCE DESCRIPTION: SEQ ID NO:35:

TACGATAACC GAAGTTACCG    20

( 2 ) INFORMATION FOR SEQ ID NO:36:

( i ) SEQUENCE CHARACTERISTICS:
( A ) LENGTH: 21 bases
( B ) TYPE: nucleic acid
( C ) STRANDEDNESS: single
( D ) TOPOLOGY: linear ( x i ) SEQUENCE DESCRIPTION: SEQ ID NO:36:

GATACGGTAA CCAAAGTCAC C    21

( 2 ) INFORMATION FOR SEQ ID NO:37:

( i ) SEQUENCE CHARACTERISTICS:
( A ) LENGTH: 19 bases
( B ) TYPE: nucleic acid
( C ) STRANDEDNESS: single
( D ) TOPOLOGY: linear ( x i ) SEQUENCE DESCRIPTION: SEQ ID NO:37:

GATACGGTAA CCGAGGTCA    19

( 2 ) INFORMATION FOR SEQ ID NO:38:

( i ) SEQUENCE CHARACTERISTICS:
( A ) LENGTH: 20 bases
( B ) TYPE: nucleic acid
( C ) STRANDEDNESS: single
( D ) TOPOLOGY: linear ( x i ) SEQUENCE DESCRIPTION: SEQ ID NO:38:

CAAAACCAAC CCACTTAACG    20

( 2 ) INFORMATION FOR SEQ ID NO:39:

( i ) SEQUENCE CHARACTERISTICS:
( A ) LENGTH: 23 bases
( B ) TYPE: nucleic acid
( C ) STRANDEDNESS: single
( D ) TOPOLOGY: linear ( x i ) SEQUENCE DESCRIPTION: SEQ ID NO:39:

TGATACAGTA ACCGAAGTTA CTG    23

( 2 ) INFORMATION FOR SEQ ID NO:40:

( i ) SEQUENCE CHARACTERISTICS:
( A ) LENGTH: 22 bases
( B ) TYPE: nucleic acid
( C ) STRANDEDNESS: single
( D ) TOPOLOGY: linear ( x i ) SEQUENCE DESCRIPTION: SEQ ID NO:40:

TACAGTAACC GCAAAGTTAC TG    22

( 2 ) INFORMATION FOR SEQ ID NO:41:

( i ) SEQUENCE CHARACTERISTICS:
( A ) LENGTH: 20 bases
( B ) TYPE: nucleic acid
( C ) STRANDEDNESS: single
( D ) TOPOLOGY: linear ( x i ) SEQUENCE DESCRIPTION: SEQ ID NO:41:

GGTCTCGTTC GTTAATCGAA  20

( 2 ) INFORMATION FOR SEQ ID NO:42:

( i ) SEQUENCE CHARACTERISTICS:
    ( A ) LENGTH: 21 bases
    ( B ) TYPE: nucleic acid
    ( C ) STRANDEDNESS: single
    ( D ) TOPOLOGY: linear ( x i ) SEQUENCE DESCRIPTION: SEQ ID NO:42:

CATCACAGAC CTGTTATTGC C  21

( 2 ) INFORMATION FOR SEQ ID NO:43:

( i ) SEQUENCE CHARACTERISTICS:
    ( A ) LENGTH: 17 bases
    ( B ) TYPE: nucleic acid
    ( C ) STRANDEDNESS: single
    ( D ) TOPOLOGY: linear ( x i ) SEQUENCE DESCRIPTION: SEQ ID NO:43:

CATAGAACGG CCATGCA  17

( 2 ) INFORMATION FOR SEQ ID NO:44:

( i ) SEQUENCE CHARACTERISTICS:
    ( A ) LENGTH: 20 bases
    ( B ) TYPE: nucleic acid
    ( C ) STRANDEDNESS: single
    ( D ) TOPOLOGY: linear ( x i ) SEQUENCE DESCRIPTION: SEQ ID NO:44:

AAACTTAAAG GAATTGACGG  20

( 2 ) INFORMATION FOR SEQ ID NO:45:

( i ) SEQUENCE CHARACTERISTICS:
    ( A ) LENGTH: 20 bases
    ( B ) TYPE: nucleic acid
    ( C ) STRANDEDNESS: single
    ( D ) TOPOLOGY: linear ( x i ) SEQUENCE DESCRIPTION: SEQ ID NO:45:

CGGTGTGTAC AAAGGGCAGG  20

( 2 ) INFORMATION FOR SEQ ID NO:46:

( i ) SEQUENCE CHARACTERISTICS:
    ( A ) LENGTH: 23 bases
    ( B ) TYPE: nucleic acid
    ( C ) STRANDEDNESS: single
    ( D ) TOPOLOGY: linear ( x i ) SEQUENCE DESCRIPTION: SEQ ID NO:46:

AACTTCGGTT ATCGTATCAC TTC  23

( 2 ) INFORMATION FOR SEQ ID NO:47:

( i ) SEQUENCE CHARACTERISTICS:
    ( A ) LENGTH: 23 bases
    ( B ) TYPE: nucleic acid
    ( C ) STRANDEDNESS: single
    ( D ) TOPOLOGY: linear ( x i ) SEQUENCE DESCRIPTION: SEQ ID NO:47:

GTAACTTCGG TTATCGTATC ACT  23

(2) INFORMATION FOR SEQ ID NO:48:

(i) SEQUENCE CHARACTERISTICS:
    (A) LENGTH: 21 bases
    (B) TYPE: nucleic acid
    (C) STRANDEDNESS: single
    (D) TOPOLOGY: linear (xi) SEQUENCE DESCRIPTION: SEQ ID NO:48:

CTTCGGTTAT CGTATCACTT C    21

(2) INFORMATION FOR SEQ ID NO:49:

(i) SEQUENCE CHARACTERISTICS:
    (A) LENGTH: 21 bases
    (B) TYPE: nucleic acid
    (C) STRANDEDNESS: single
    (D) TOPOLOGY: linear (xi) SEQUENCE DESCRIPTION: SEQ ID NO:49:

ACTTCGGTTA TCGTATCACT T    21

(2) INFORMATION FOR SEQ ID NO:50:

(i) SEQUENCE CHARACTERISTICS:
    (A) LENGTH: 508 bases
    (B) TYPE: nucleic acid
    (C) STRANDEDNESS: single
    (D) TOPOLOGY: linear (xi) SEQUENCE DESCRIPTION: SEQ ID NO:50:

```
AAACTTAAAG GAATTGACGG AGGGGCACCA CCAGGCGTGG          40
AGCCTGCGGC TTAATTTGAC TCAACACGGG GAAACTCACC          80
AGGTCCAGAC ATGGGAAGGA TTGACAGATT GATAGCTCTT         120
TCTTGATTCT ATGGGTGGTG GTGCATGGCC GTTCTTAGTT         160
GGTGGAGTGA TCTGTCTGGT TAATTTCGAT AACGAACGAG         200
ACCTTGGCCT GCTAAATAGG GTCGGTGACT TTGGTTACCG         240
TATCGCTTCT TAGAGGGACT TTGCGTGTCT AACGCAAGGA         280
AGTTTGAGGC AATAACAGGT CTGTGATGCC CTTAGATGTT         320
CTGGGCTGCA CGCGCGCTAC ACTGATGCAT GCAACGAGTT         360
TTTACCTTGA CCGACGGGGC TGGGTAATCT TGTGAGGGTG         400
CATCGTGATG GGATAGATT ATTGCAATTA TTAGTCTTCA          440
ACGAGGAATG CCTAGTAGGC GCAAGTCAGC ACTTGCGCCG         480
ATTACGTCCC TGCCCTTTGT ACACACCG                      508
```

EIMERIA MAXIMA 16S RDNA PROBES

RELATED U.S. APPLICATION DATA

This application is a continuation-in-part of application Ser. No. 07/706,628, filed May 29, 1991, abandoned, which is incorporated herein by reference.

BRIEF DESCRIPTION OF THE DRAWINGS

FIGS. 1, A and B. Single strand nucleotide sequence for *E. acervulina* small subunit rRNA gene. (SEQ ID NO:24)

FIG. 2, A and B. Single strand nucleotide sequence for *E. brunetti* small subunit rRNA gene. (SEQ ID NO:25)

FIGS. 3, A and B. Single strand nucleotide sequence for *E. maxima* small subunit rRNA gene. (SEQ ID NO:26)

FIGS. 4, A and B. Single strand nucleotide sequence for *E. mitis* small subunit rRNA gene. (SEQ ID NO:27)

FIGS. 5, A and B. Single strand nucleotide sequence for *E. necatrix* small subunit rRNA gene. (SEQ ID NO:28)

FIGS. 6, A and B. Single strand nucleotide sequence for *E. praecox* small subunit rRNA gene. (SEQ ID NO:29)

FIGS. 7, A and B. Single strand nucleotide sequence for *E. tenella* small subunit rRNA gene. (SEQ ID NO:30)

FIG. 9. Species-specific hybridization to genomic DNA isolated from purified preparations of Eimeria, showing that the Eimeria probes hybridize to both non-precocious laboratory isolates and vaccine strains.

FIG. 16. Direct fecal oocysts DNA target in probe hybridization/parasite quantitation assay.

BACKGROUND OF THE INVENTION

Figure 8:
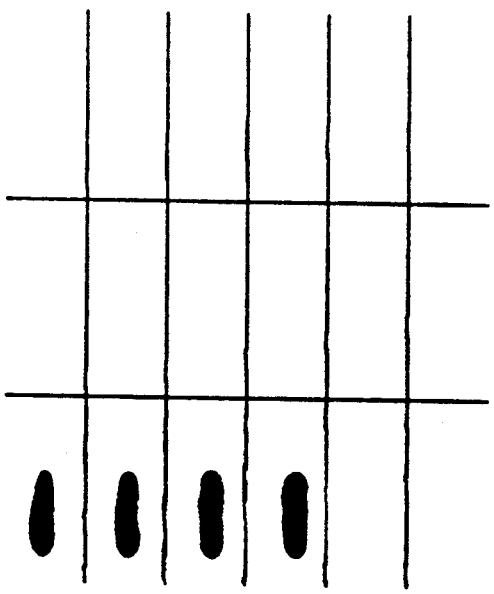
FIG. 8. Species-specific hybridization to genomic DNA isolated from purified preparations of Eimeria, showing the specificity of the *E. tenella* probe.

Live coccidiosis vaccines (LCV) consisting of particles composed of an immunogenic dose of oocysts from precocious isolates of chicken Eimeria species embedded in a firm gel matrix are well known in the art, as exemplified by U.S. Pat. Nos. 4,544,548, issued Oct. 1, 1985; 4,552,759 issued Nov. 12, 1985; 4,752,475 issued on Jun. 21, 1988; 4,863,731 issued Sep. 5, 1989 and Patent Cooperation Treaty, International Publication No. WO 85/00752. Evaluation of live coccidiosis vaccine characteristics such as viability of each of the species included in the vaccine is paramount to the production and use of the vaccine. In addition, any assay used to determine viability must also be semi-quantitative so that the immunogenic efficacy of each species in the particle can be predicted.

Viability of chicken Eimeria oocysts can only be credibly assessed by expansion or reproduction in the natural host, as no efficient in vitro models are available. The ability to detect parasites in the intestinal epithelia and mucosa of vaccinated birds, the target tissue for these protozoa, verifies that the organisms are in fact capable of penetrating the intestinal epithelium and intracellular development. Detection of oocysts shed in feces indicates that the inoculum contains fully competent parasites capable of traversing the entire life cycle.

Historically the Eimeria species (spp.) have been classified according to a range of parameters, including morphology, type of pathology induced, immunological specificity, characteristic life cycles and biochemical markers (Joyner and Long, Avian Path. 3, 145-157 [1974]); Shirley, In: McDougold, Joyner and Long, Eds., Research in Avian Coccidiosis, Athens, Ga.: University of Georgia, pp. 13-35 [1985]). However these methods of speciation are tedious and are not quantitative. Furthermore, no single method can unequivocally differentiate all species. Infectivity assays for multivalent live coccidiosis vaccines require unequivocal speciation, semi-quantitation and a stream-lined procedure, owing to the anticipated short half life of the vaccine preparation. Existing methodologies do not satisfy these requirements.

The ribosomal RNA (rRNA) gene loci harbor a wealth of information that has been successfully used to establish phylogenetic relationships among and within eukaryotic kingdoms (Hasegawa et al., J. Mol. Evol. 22: 32-80 [1985]). Ribosomal RNA genes from protozoa including *Toxoplasma gondii* (Johnson et al., Exp. Parasitol. 63: 272-278 [1987]), members of the genus Plasmodium (Dame and McCutchan, J. Biol. Chem. 258: 6984-6990 [1983], Langsley et al., Nucleic Acids Res. 11: 8703-8717 [1983]) and Eimeria spp. (Ellis and Blumstead, Parasitol. 101: 1-6 [1990]); Johnson et al., System. Parasitol. 18: 1-8 [1991]) have been cloned and characterized towards this end. An extension of this type of analysis in Plasmodium (McCutchan et al., Mol. Biochem. Parasitol. 28: 63-68 [1988]) resulted in the design of species-specific oligonucleotide probes derived from the nucleotide sequence of areas within the small subunit rRNA gene.

OBJECTS OF THE INVENTION

It is accordingly, an object of the present invention to prepare purified Eimeria species DNA encoding small subunit ribosomal RNA (ssrRNA) genes free of other Eimeria nucleic acids and other cellular constituents. A further object is to insert the ssrRNA DNA into suitable vectors, transform an appropriate host with the vector and determine the nucleotide sequence of the DNA. Another object is to provide unique species-specific phylogenetically divergent segments of the ssrRNA genes which are used as probes for individual species. Another object is to prepare oligonucleotides complimentary to the divergent regions. Another object is to use the unique probes and assay to quantitate and/or identify each Eimeria species in a mixture of Eimeria species. A further object is to use the unique probes in a method to quantitate the relative levels of each of multiple Eimeria species in infected host tissue.

SUMMARY OF THE INVENTION

Unique species-specific Eimeria maxima DNA probes comprising divergent DNA sequences are disclosed. The probes are complementary to a small subunit ribosomal RNA gene of *Eimeria maxima*.

DETAILED DESCRIPTION OF THE INVENTION

The present invention relates to assays and species-specific identification probes which allows unequivocal speciation of multiple Eimeria species, semi-quantitation of the concentration of each species and a shortened time period for determining these parameters.

The following techniques have been used to identify deoxyribonucleic acid (DNA) probes that are specific for each of multiple species of Eimeria that are used to prepare a multivalent coccidiosis vaccine. DNA probe as used herein refers to a DNA sequence or segment, frequently labeled with radioactive isotopes, that is used to identify a gene. A DNA segment as used herein refers to a sequence of nucleotides between about 2 bases and about 2 kb (kilobases) in length. The Eimeria species include, but are not limited to, *E. acervulina, E. brunetti, E. maxima, E. mitis, E. necatrix, E. praecox* and *E. tenella.* An extended list of Eimeria species can be found in Patent Cooperation Treaty, Publication No. WO 85/00752. The small subunit rRNA gene from any or all of the Eimeria species is cloned and sequenced by the process described herein. Comparative analysis of these nucleotide sequences illustrates multiple segments within the sequence which are highly conserved across broad phylogenetic lines, as well as regions which are divergent even within a genus (i.e. species-specific). A conserved sequence refers to a DNA segment in a gene that has not changed in the course of evolution, while a divergent sequence refers to DNA segment that has changed considerably. Divergent sequences vary considerably in the length of the DNA segment which has changed. In the procaryotic genus Francisella, species can be differentiated by a single base difference in their ssrRNA genes, Forsman et al., Appl. Environ. Microbiol. 949-955 (1990). Trypanosomes, on the other hand, contain unique DNA segments in their ssrRNA genes which are several hundred bases long, Dams et al., Nucleic Acids Res. 165: r87-r173, (1988). The unique divergent sequences serve as ideal probes for identification of specific species within the genus Eimeria. Deoxyribooligonucleotides (single strands of DNA) corresponding to divergent sequences are synthesized, used as hybridization probes and act as effective species-specific reagents.

An assay of this type must be sufficiently sensitive so as to be able to detect the expansion or reproduction of a very small oocyst inoculum. In other models DNA hybridization probes have been successfully used to quantitate parasite load in infected hosts. For example, exoerythrocytic forms (EEF) of *Plasmodium berghei* have been assayed in genomic DNA prepared from rat liver extracts using a repetitive plasmodial DNA probe (Ferreira et al., Mol. Biochem. Parasitol. 12: 103-109 [1986]). More recently, oligonucleotide probes derived from rRNA sequences have been employed to quantitate EEF of *Plasmodium yoelii* in RNA prepared from the livers of infected mice (Arreaza et al., Exp. Parasitol. 72: 103-105 [1991]). Similarly, any assay for a live coccidiosis vaccine must be capable of detecting Eimeria sequences contained within a total nucleic acid preparation (whether it be RNA or DNA) from chicken intestinal epithelia and mucosa. Because the Eimeria sequences represent such a small percentage of the genetic information in the extract, direct hybridization to DNA is not sufficiently sensitive to detect the vaccine oocyst dose for each species. Because of the biological amplification of rRNA sequences within cellular RNA pools, hybridization of the Eimeria species-specific oligonucleotide probes to RNA preparations from intestinal epithelia and mucosa is one way in which this assay and oligonucleotide probes of this invention can be used. Genomic DNA prepared from oocysts shed in the feces of vaccinated birds can also be characterized as a hybridization target for the oligonucleotide probes. This source of parasite nucleic acid is relatively free of host genetic material and so in effect represents an enriched hybridization target.

Enzymatic amplification of ssrRNA gene sequences in genomic DNA prepared from intestinal epithelia and mucosa is a novel alternative approach to enrichment which in the end allows for increased sensitivity in this unique assay. Using the polymerase chain reaction (PCR; Saiki et al., Science 239: 487-491 [1988]) and primers which efficiently hybridize to eukaryotic small subunit rRNA genes, it has been possible to selectively amplify each of the ssrRNA gene units or fragments thereof within the genomic DNA prepared from the intestinal epithelia and mucosa of infected chickens. Primer as used herein refers to a relatively short oligonucleotide that specifically attaches to a region of single-stranded template and is necessary to form the starting point for reverse transcriptase to copy adjacent sequences of RNA (mRNA, rRNA and tRNA), or for DNA polymerase to synthesize complementary-strand DNA. A primer can also be used with specific polymerases to produce complementary-strand synthesis with single-stranded genomic DNA, i.e. polymerase chain reaction. Complementary base pairing as used herein is defined as the linking of bases on double-stranded nucleic acids according to the base-pairing rules which are well known in the art. A complementary base sequence is a base sequence in a nucleic acid strand that is related to the base sequence in another strand by the same base-pairing rules. This includes Eimeria rRNA genes, chicken rRNA genes as well as rRNA genes derived from any other eukaryotic organism that might be represented in the chicken intestine. Amplification is selective in the sense that only small subunit rRNA genes are enriched as a result of the PCR reaction, but nonspecific because each small subunit rRNA gene is enriched to the same extent. The PCR amplification products are quantitated using a fluorescent dye binding assay (Labarca and Paigen, Anal. Biochem. 102: 344-352 [1980]) and equivalent amounts of amplified DNA fragments are denatured and immobilized on a support membrane.

The species-specific oligonucleotide probes are then used in hybridization reactions to determine the presence or absence of each of the species of Eimeria in the amplified PCR product and therefore in the intestine of the vaccinated chickens. Hybridization reactions are defined as a reaction which results in the formation of a double-stranded molecule by complementary base-pairing between two single-stranded DNA molecules, or a single-stranded DNA molecule and an RNA molecule. A control hybridization probe, derived from a portion of the sequence contained within the PCR product in a region which is conserved in all eukaryotic small subunit rRNAs, is used to normalize the amount of denatured and immobilized DNA on the filter. Standards using genomic DNA prepared from individual species of Eimeria as PCR templates are included on each hybridization filter. These are used to construct a standard curve and will also serve as hybridization specificity standards. Radioactive emissions from the respective filters are quantitated using the Molecular Dynamics PhosphorImager (Johnston et al., Electrophoresis 11: 355-360 [1990]).

The following method is used to clone Eimeria small subunit ribosomal RNA (rRNA) genes. It is intended that the following method is not the only process for cloning the Eimeria small subunit rRNA genes and that others known in the art can be used. Oocysts from laboratory strains of *E. acervulina, E. brunetti, E. maxima, E. mitis, E. necatrix, E. praecox* and *E. tenella* are propagated by oral infection of broiler chickens. *Eimeria tenella* oocysts are isolated from the cecal contents of chickens at about 5-7 days post-infection. The cecal contents are physically disrupted in a Waring Blender, in distilled water and digested with pepsin. Following digestion, debris is removed by centrifugation in distilled water. The remaining Eimeria species are individually isolated from fecal collections about 3-8 days following infection. The feces is diluted about ten fold in distilled water and then the contents are passed through a sieving device. A series of passes through screens of decreasing size functionally removes a considerable amount of fecal debris. Partially pure oocyst fractions for each Eimeria species are then collected by flotation in about 2.2M sucrose (Jackson, Parasitol. 54: 87-93 [1964]), and further treated by incubation in sodium hypochlorite at a concentration of 5.25%, in water at about 40° C. for about 10 minutes. The sodium hypochlorite is removed by several washes in sterile phosphate buffered saline (PBS) at about pH 7.6 to obtain purified, sterile oocysts. Depending upon the species, oocysts are allowed to sporulate in a shaking water bath for about 24 to about 60 hours at about 20° C. (Edgar, Trans. Am. Micr. Soc. 62: 237-242 [1954]) in PBS or sterile water. Following sporulation, oocysts are washed several times in PBS.

Sporulated oocysts are disrupted by shaking with 3 mm sterile glass beads. Beads are added to the oocyst suspension and the mixture is mixed vigorously on a Vortex mixer for about 2 minutes. Periodically the extent of breakage is assessed microscopically. When approximately 50% breakage has occurred, the glass beads are allowed to settle and the sample above the beads is removed and mixed with an equal volume of Percoll (Pharmacia). The disrupted oocysts are subjected to centrifugation at about 2,000 to about 5,000 × g for about 10 min at about 4° C. to pellet the enriched sporocyst fraction. Unbroken oocysts form a layer on top of the 50% Percoll and are removed, washed in PBS, mixed with glass beads and mixed again as described above. This procedure is performed repeatedly (3-4 times) until very few unbroken oocysts remain following Percoll fractionation. Sporocyst pellets are combined and washed several times in PBS.

Sporocysts are then diluted in 0.01M Tris (pH 8.0), 0.2M NaCl to a concentration of approximately $10^8$ per ml and the suspension is adjusted to about 1% sodium dodecyl sulfate (SDS) and about 10 mM EDTA which results in membrane lysis. The released genomic DNA is solubilized by digestion with Proteinase K (150 μg/ml) for approximately 30 minutes at about 65° C. Genomic DNA is extracted twice with buffer equilibrated phenol (about pH 7.6), twice with a mixture of phenol/chloroform/isoamyl alcohol at about 25:24:1, and twice with chloroform/isoamyl alcohol at about 24:1. The final aqueous phase is dialyzed overnight in 10 mM Tris (pH 8.0), 10 mM NaCl, 10 mM EDTA (pH 8.0). RNA which has co-purified with the DNA is selectively removed from the dialysate by digestion with heat inactivated RNase A used at a concentration of about 150 μg/ml. The samples are incubated for about 1 hour at about 37° C. The RNase and other residual protein is removed by a secondary digestion with Proteinase K (about 150 μg/ml, for about 30 minutes at about 37° C.). The genomic DNA is then successively extracted with organic solvents as described above. The final aqueous phase is precipitated with about 0.1 volumes of about 3M sodium acetate and about 2.5 volumes of about 100% ethanol. Glycogen is added to 20 μg/ml to act as carrier. The pellets are washed twice with about 70% ethanol. The genomic DNA pellet is air dried by inversion and is then suspended in about 10 mM Tris.HCl (pH 7.6), 1 mM EDTA buffer (TE) or distilled water at a concentration of about $5-8 \times 10^8$ sporocyst equivalents/ml and quantitated by absorbence at 260 nm. An aliquot of DNA is then analyzed by agarose gel electrophoresis to confirm (i) the spectrophotometric generated concentration, (ii) the lack of residual RNA, and (iii) it's high molecular weight integrity.

The ribosomal RNA (rRNA) gene loci harbor a wealth of information that has been successfully used to establish phylogenetic relationships among and within eukaryotic kingdoms (Hasegawa et al., J. Mol. Evol. 22: 32-80 [1985]). Sequences of the small subunit rRNA from a number of highly divergent organisms have recently been compiled (Dams et al., Nucleic Acids Res. 16S: r87-r173 [1988], Neefs et al., Nucleic Acids Res. 18S: 2237-2317 [1990]). Comparative analysis of these nucleotide sequences identifies areas with dramatic sequence similarities and other areas that are characterized by considerable sequence drift or divergence. Regions close to both the 5'- and 3'-ends of the consensus small subunit rRNA (ssrRNA) sequence with near identity in the eukaryotic kingdom were chosen. Consensus sequence is defined as a sequence of nucleotides derived from a large set of observed similar sequences in a specific region of a nucleic acid. Oligonucleotide primers corresponding to these sequences were chosen:

| | |
|---|---|
| 5'-ACCTGGTTGATCCTGCCAG-3' SEQ ID NO: 1 | ERIB 1 |
| 5'-CTTCCGCAGGTTCACCTACGG-3' SEQ ID NO: 2 | ERIB 10 |

The oligonucleotides were synthesized using an Applied Biosystems 380B instrument and purified as per the manufacturer's recommendations. The ERIB 1 (SEQ ID NO:1) primer represents a consensus sequence less than 10 nucleotides from the 5'-end of eukaryotic ssrRNA genes. The ERIB 10 (SEQ ID NO:2) primer is the inverse complement to a consensus sequence located approximately 20 nucleotides from the 3'-end of eukaryotic ssrRNA genes. Taken together, these two oligonucleotides span the vast majority of the ssrRNA gene sequence. It is intended that the ERIB 1 and ERIB 10 primers are not the only primers that can be used to amplify the ssrRNA genes or selected fragments thereof. With the knowledge of the present invention one could probably devise other primers which could accomplish the intended goal.

ERIB 1 (SEQ ID NO:1) and ERIB 10 (SEQ ID NO:2) are used as a primer pair in the polymerase chain reaction (PCR, Saiki et al., Science 239: 487-491 [1988]) with the intention of selectively amplifying the ssrRNA genes contained within the genomic DNA preparation of each Eimeria species as described above. Genomic DNA is quantitated using a fluorescent dye binding assay (Lebarca and Paigen, Anal. Biochem. 102: 344-352 [1980]) and diluted in distilled water to a final concentration of about 2.5 ng/µl for use as the PCR template. A 10 X reaction buffer consisting of about 100 mM Tris-HCl (about pH 8.3), about 500 mM KCl, about 15 mm $MgCl_2$, about 0.01% gelatin is prepared as well as about 100 mM stocks of Tris-HCl (about pH 7.6) buffered dATP, dCTP, dGTP and dTTP. Initially, the reaction mix cocktail is prepared by mixing the following components at these final concentrations in this specific order: water, dATP, dCTP, dGTP and dTTP (each at about 200 µM), about 1 X reaction buffer, about 1 µM of each of the two oligonucleotide primers (ERIB 1 and ERIB 10) (SEQ ID NO:1, SEQ ID NO:2), and about 1.25 U Taq DNA polymerase. The reaction mixture is assembled in dedicated PCR reaction tubes by combining about 90 µl of the reaction cocktail with about 10 µl (25 ng) of genomic DNA. The reaction is overlayed with approximately 50 µl of light mineral oil and then placed into a Perkin Elmer Cetus DNA thermal cycler programmed as follows:

about 35 cycles each composed of (i) about 94° C. for about 60 seconds to denature, (ii) about 50° C. for about 90 seconds to anneal, and (iii) about 72° C. for about 120 seconds for polymerization about one cycle at about 72° C. for about 10 minutes for extension A 5 µl aliquot of the amplification reaction product is subjected to agarose gel DNA electrophoresis in TAE buffer (40 mM Tris-acetate, 2 mM ethylenediaminetetraacetic acid [EDTA]) along with DNA size standards. A characteristic band approximately 1.8 kb in length, whose size is roughly predicted by analogy to other eukaryotic ssrRNA genes, suggests that ERIB 1 (SEQ ID NO: 1) and ERIB 10 (SEQ ID NO:2) faithfully hybridized to the Eimeria ssrRNA genes and that Taq DNA polymerase synthesized a reaction product by extension from the 3'-ends of these primers.

By definition, the ends of the 1.8 kb PCR products correspond to the input oligonucleotides and should be blunt. However, Taq DNA polymerase is prone to adding single non-template-directed nucleotides, in particular dATP, to the 3'-end of duplex PCR products (Clarke, Nucleic Acids Res. 16: 9677-9686 [1988]). In order to increase cloning efficiency, the ends of the PCR products are "polished" to blunt-ends by the action of either T4 DNA polymerase or the Klenow fragment of bacterial DNA polymerase. Reaction products are extracted once with phenol, once with a phenol/chloroform/isoamyl alcohol mix and once with chloroform/isoamyl alcohol as described earlier. DNA is precipitated with sodium acetate/ethanol and the pellet is washed twice with 70% ethanol. For the Klenow fragment reaction, the DNA (about 1-10 µg) is suspended in about 15 µl of water and mixed with about 2 Ill of 1OX nick translation buffer (about 0.5M Tris-Cl [pH 7.2], 0.1M $MgSO_4$, 1 mM dithiothreitol, 500 µg/ml bovine serum albumin [BSA Pentax Fraction V]), and about 2 µl of a 1.25 mM solution of all four dNTPs and about 1 µl (=5 Units) Klenow. The reaction is conducted at about 14° C. for about 1 hour and is terminated by heating at about 65° C. for about 10 minutes. The polished 1.8 kb DNA products are passed over a G 25 column, extracted once with phenol, and twice with chloroform/isoamyl alcohol as described earlier. The DNA is precipitated with sodium acetate/ethanol and the pellet is washed twice with about 70% ethanol. The DNA is resuspended in about 36 µl of water and mixed with about 4 µl of 0.2M Tris.HCl (pH 9.5), 10 mM spermidine, 1 mM EDTA. This reaction mixture is incubated at about 70° C. for about 5 minutes and subsequently rapidly chilled on ice. To the above 40 µl are added 5 µl of 10X blunt end kinase buffer (0.5M Tris-Cl [pH 9.5], 0.1M $MgCl_2$, 50 mM dithiothreitol, 50% glycerol), and about 5µl of a 10 mM solution of ATP and 2 µl (=20U) of T4 polynucleotide kinase. The reaction is conducted at about 37° C. for about 30 minutes and is terminated by the addition of about 2 µl of 0.5M EDTA. The reaction mixture is brought to about 100 µl with TE buffer and the reaction products are extracted once with phenol, once with phenol/chloroform/isoamyl alcohol mix and once with chloroform/isoamyl alcohol as described previously. DNA is precipitated with sodium acetate/ethanol and the pellet is washed twice with about 70% ethanol, as above. The DNA is resuspended in about 20 µl of water and quantitated by absorbence at 260 rum.

The polished 1.8 kb DNA products are then agarose gel purified to remove residual oligonucleotide primers and nonspecific PCR products. Gel slices containing the bands of interest are excised, melted and the DNA eluted using Geneclean II (BIO 101 Inc., Vogelstein and Gillespie, Proc. Natl. Acad. Sci. USA 16: 615-619 [1979]) as per the manufacturer's instructions. Eluted DNA products are then quantitated by absorbence at 260 run.

A phagemid cloning vector pUC120 (Vieria, Birepli-con Filamentous Phages and the Production of Single Stranded Plasmid DNA. Ph.D. thesis, University of Minnesota [1989]) is cut at it's unique Sma I site in the polylinker. Other suitable cloning vectors include but are not limited to the pGEM-Zf series (Promega Corporation) and the pBluescript II series (Stratagene Cloning Systems). Cutting is monitored by analytical agarose gel electrophoresis. The linearized DNA is then extracted with organic solvents, precipitated and washed with 70% ethanol as described earlier. The 5'-end of each strand of the plasmid is phosphatased with calf intestinal phosphatase (CIP) to decrease the frequency of an autoligation event. This is accomplished by mixing the linearized plasmid about 10 µg with 5 µl of 10 X CIP buffer (about 0.5M Tris-HCl, pH 9.0, about 10 mM $MgCl_2$, about 1 mM $ZnCl_2$, about 10 mM spermidine) and about 1 µl (1 Unit) of CIP in a final 50 µl reaction volume. The reaction is conducted for about 15 minutes at about 37° C. and then about 15 minutes at about 56° C. A second aliquot of CIP is then added and the reaction is repeated as above. The reaction is terminated by the addition of about 40 µl of $H_2O$, about 10 µl of about 10 X STE buffer (about 100 mM Tris-HCl, pH 8.0, about 1M NaCl, about 10 mM EDTA), about 2.5 µl of about 20% SDS and heated at about 68° C. for about 15 minutes. The linearized, phosphatased vector is then extracted, precipitated and washed as above.

Ligation of the gel purified ssrRNA gene PCR products into the blunt Sma I site within the pUC120 polylinker is then conducted. Approximately 100 ng of linearized vector is mixed with an equimolar amount of the respective PCR products in a 20µl reaction mixture which, in addition is composed of about 66 mM Tris-HCl pH 7.6, about 5 mM $MgCl_2$, about 5 mM dithiothreitol, about 1 mM ATP. The reaction is initiated by the addition of T4 DNA ligase (about 400 units) and proceeds for about 12-16 hours at about 14° C.

Bacterial cells are rendered competent and capable of uptake of foreign DNA by the following method. A predetermined volume (about 2 ml per transformation reaction) of sterile 2X YT bacterial media (about 16 g bactotryptone, about 10 g yeast extract, about 5 g NaCl per liter) is inoculated with a single colony of *Escherichia coli* MV1184 and grown with vigorous mixing at about 37° C. until it reached an optical density of about 0.6 at about 600 run. Other suitable bacterial hosts include but are not limited to MN522, JM101, TB1 and XL1-Blue. The bacterial cells are collected by centrifugation at about $1000 \times g$, at about 4° C., for about 5 minutes. The resulting cell pellet is gently suspended in one-half of the original culture volume with sterile $CaCl_2$, about 50 mM. The suspension is then placed on ice for about 20 minutes and the cells are again collected by centrifugation. The cells are then gently suspended D in one-tenth volume of sterile 50 mM $CaCl_2$. The bacterial suspension is then kept at 4° C. for 16-24 hours.

From the 20 $\mu l$ ligation reaction mixture about 2 $\mu l$ and about 18 $\mu l$ aliquots are dispensed to sterile polypropylene tubes. Approximately 100 $\mu l$ of competent bacteria are added to each of the tubes containing the ligation reactions (as well as the appropriate ligation and transformation controls) and these are placed on ice for 40 minutes. After this, the bacteria are "heat-shocked" by incubation at about 42° C. for 90 seconds and then allowed to recover for approximately 5 minutes at room temperature. Each transformation tube is then plated onto a 2X YT agar plate which contains ampicillin at a concentration of about 50 mg/l for the selection of bacteria harboring plasmids and for plasmid maintenance. Plates are incubated in an inverted position overnight at 371 C.

Bacterial clones harboring plasmids are selected by their ability to grow on plates in the presence of ampicillin. Single colonies are used to inoculate about 5 ml of 2X YT/AMP (i.e., 2X YT media containing ampicillin at 50 mg/l) and these cultures are grown overnight at about 37° C. with vigorous shaking. Approximately 1.5 ml of the culture is poured off into an Eppendorf tube and collected by centrifugation in an Eppendorf centrifuge for at least 1 min; the remainder of the culture is stored at about 4° C. to serve as a genetic stock. The media above the bacterial pellet is aspirated off and the pellet is suspended by mixing in about 100 $\mu l$ of a cold, freshly prepared solution of about 50 mM glucose, about 10 mM EDTA, about 25 mM Tris-HCl (pH 8.0), about 4 mg/ml lysozyme. This mixture is incubated at room temperature for about 5 minutes. Then about 200 $\mu l$ of a cold, freshly prepared solution, composed of about 0.2N NaOH and about 1% SDS is added to each tube, mixed gently by inversion, and put on ice for about 5 minutes. About 150 $\mu l$ of a cold, freshly prepared solution containing about 6 ml of about 5M potassium acetate, about 1.15 ml of glacial acetic acid and about 2.85 ml distilled water is added to each tube. The contents are gently vortexed and this mixture is stored on ice for about 5 minutes. The cellular debris is collected by centrifugation in an Eppendorf centrifuge for 10 minutes at about 4° C. and the supernatant fluid is extracted one time with phenol/chloroform/isoamyl alcohol (about 25:24:1). Plasmid DNA and cellular RNA are precipitated from the final aqueous phase with the addition of two volumes of room temperature 100% ethanol. A pellet is collected by centrifugation for about 5 minutes at room temperature; the pellet is washed one time with 70% ethanol and then dried briefly. The nucleic acid pellet is then suspended in about 50 $\mu l$ of TE containing about 20 $\mu g$ of DNase-free RNase per ml and incubated for about 15-30 minutes at about 37° C. to quantitatively eliminate cellular RNA. Aliquots of about 10 $\mu l$ are then cut to completion with Hind III and Eco R1 (each at approximately 20 units) in a buffer composed of about 50 mM NaCl, about 100 mM Trim-HCl (pH 7.5) and about 5 mM $MgCl_2$ at about 37° C. for about 60 min. The restriction enzyme reaction products are fractionated by agarose gel electrophoresis along with known DNA size markers to identify those plasmids which contained the appropriate inserts. Those recombinant plasmids which contain the predicted 1.8 kb insert are then cut with a second restriction enzyme (usually Pst I) to verify; (i) that only a single copy of the insert is contained within the plasmid, and (ii) to score for orientation of the insert DNA with respect to the bacterial promoter. This is accomplished by removing a second 10 $\mu l$ aliquot from the remaining 40 $\mu l$ of RNase-digested bacterial nucleic acid and cutting it in a buffer composed of about 100 mM NaCl, about 10 mM Trim-HCl (pH 7.5), about 10 mM $MgCl_2$ with approximately 20 units of Pst I for about 60 D minutes at about 37° C. Again, the restriction enzyme digests are resolved by agarose gel electrophoresis.

Clones containing inserts of the appropriate size were then sequenced using the dideoxy sequencing protocol (Sanger et al J. Mol. Biol. 143: 161-178 [1980]). Single stranded phagemid sequencing templates using K07 helper phage were generated exactly as described by Vieria (*Bireplicon Filamentous Phages and the Production of Single Stranded Plasmid DNA*. Ph.D. thesis, University of Minnesota [1989]). Other commercially available helper phage for the generation of single-stranded templates from phagemid clones include R408 (Promega Corporation for use with the phagemid pGEM-Zf series and bacterial hosts MN522 or JM101) or VCSM13 and R408 (Stratagene Cloning Systems for use with the pBluescript II phagemid series and bacterial hosts XL1-Blue or NM522). Alternatively, double stranded sequencing templates were also used for dideoxy sequencing. These were prepared according to the method of Chen and Seeburg (DNA 4:165-170 [1985]). Sequencing reactions were conducted using a specifically engineered form of T7 DNA Polymerase (Tabor and Richardson, Proc. Natl. Acad. Sci. USA 84: 4767-4771 [1987]). This enzyme is available commercially from Pharmacia LKB Biotechnology or as Sequenase DNA Polymerase (United States Biochemical Corporation). Reactions were conducted as per the respective manufacturer's specifications and the reaction products were resolved by denaturing polyacrylamide gel electrophoresis (Sanger et al J. Mol. Biol. 143: 161-178 [1980]).

Examples of isolated and purified genes encoding the small subunit ribosomal RNA of Eimeria species are shown in FIGS. 1-7. The ssrRNA gene nucleotide sequences are compared to determine the conserved and divergent regions of the sequences. Divergent regions are identified following comparison and exemplified by the probes illustrated in Table 1. It is intended that the present invention include all of the divergent DNA regions of the ssrRNA genes of Eimeria species.

The divergent regions are further defined as DNA sequences of about 1 to about 50 or about 1 to about 100 nucleotides in length that are not conserved within the organisms that make up the genus Eimeria. It is preferred that the divergent species-specific sequences are found within the ssrRNA of the following Eimeria species: Eimeria species such as: E. acervulina, E. tenella, E. maxima, E. necatrix, E. praecox, E. mitis, E. brunetti. The divergent sequences are identified by comparing the nucleotide sequences shown in FIGS. 1-7.

Figure 12:
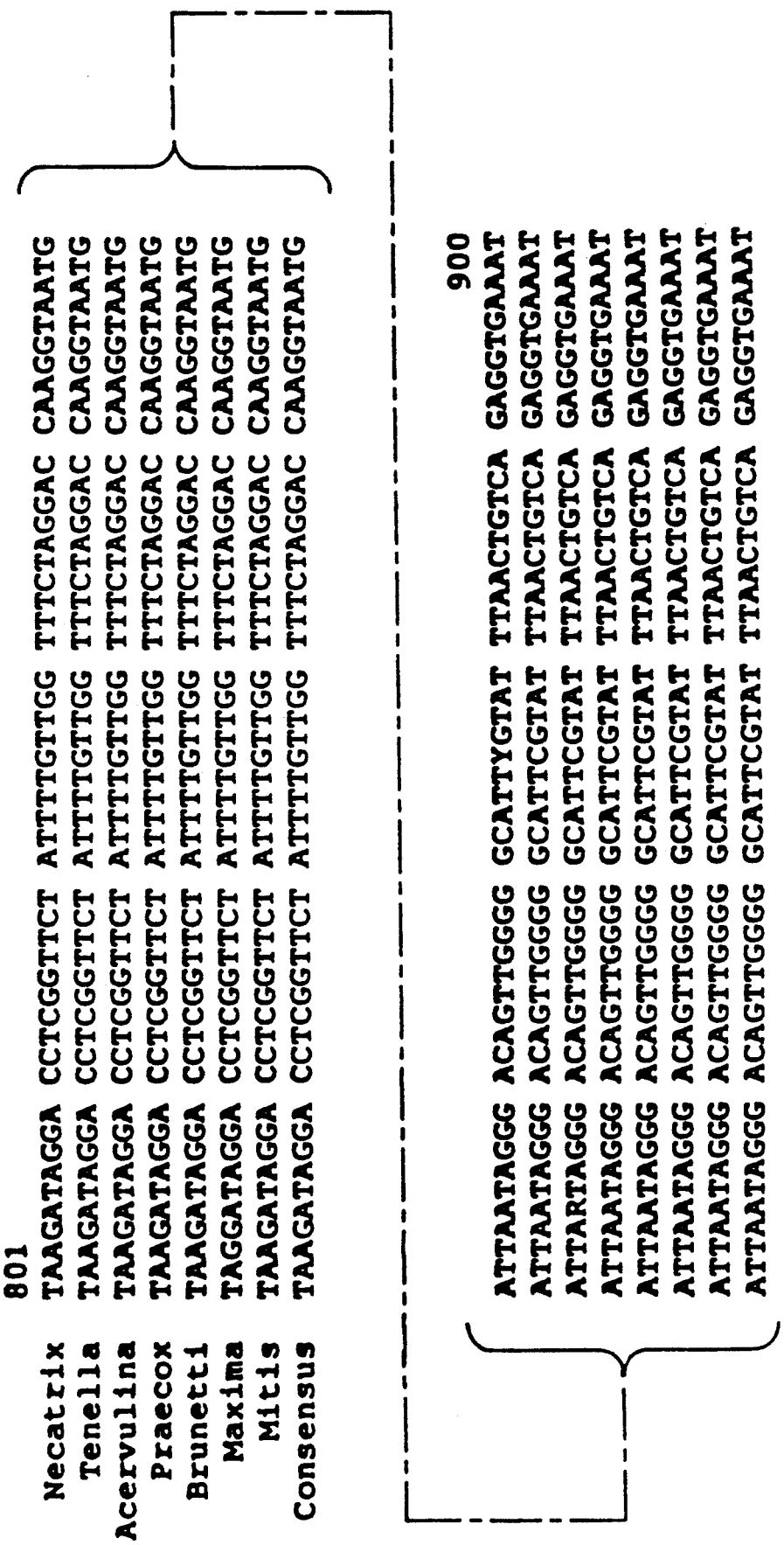
FIGS. 12A-R. Multiple nucleotide sequence alignment for chicken Eimeria using the sequences in FIGS. 1-7. (SEQ ID NO:24-30)

Table 1 represents the similarity matrix for the seven Eimeria species represented in FIGS. 1-7. This data was calculated using a computer program entitled PILEUP (GCG Software Package, Devereux, Haeberli and Smithies (1984 and A Comprehensive Set of Sequence Analysis Programs for the VAX. Nucleic Acids Research 12(1); 387-395) using the entire sequence as formatted in FIG. 12. Fundamentally the program does a base by base comparison of all possible pairs of sequences. The diagonal represents a self comparison which is 100% identity. The analysis reveals that the chicken Eimeria are a closely related group. The most similar pair is represented by E. tenella and E. necatrix whose ssrRNA sequences are 99.3% similar. From another view, this pair has 0.7% -dissimilar nucleotide sequences, which over the entire length of approximately 1750 bases implies about 12 nucleotide differences. The most dissimilar pair is represented by E. tenella and E. mitis which are 96.4% similar, which implies about 63 nucleotide differences. Thus on a global basis the ssrRNA genes in the chicken Eimeria are very similar. Fortunately the differences which do exist seem to be clustered forming divergent regions, as seen in FIG. 12. If all or a majority of the nucleotide differences were found in one region then oligonucleotides which were very dissimilar could be made which would be species-specific. Since the positions of the nucleotide differences are not highly concentrated, the unique oligonucleotides disclosed herein would superficially look very similar in some cases having about 2 nucleotide differences out of a total of about 20 nucleotides. It is this similarity in sequence which has necessitated the use of highly stringent hybridization conditions. By highly stringent hybridization conditions we mean, that conditions (salt concentrations and hybridization and wash temperatures) are such that only perfect hybrids are formed (i.e. all bases in the oligonucleotide hybridization probe perfectly base pair or bond with the PCR amplified fragment). Since we have consistently used the prehybridization, hybridization and wash protocols described previously we have used the temperature of the hybridization and subsequent washes as the main criteria for stringency. Hybridization and wash temperatures are typically about 3° to about 5° C. below the duplex melting temperature (Tm), where Tm is the temperature at which 50% of the total number of possible duplexes are annealed under standardized conditions. It is understood that the Tm is dependent upon the salt concentrations used and that changes in the hybridization and wash buffers could dramatically change the hybridization and wash temperatures needed to ensure species specificity.

TABLE 1

Similarity Matrix for Avian Eimeria (full length sequences)

| Species | Ea | Eb | Emx | Emt | En | Ep | Et |
|---|---|---|---|---|---|---|---|
| Acervulina | — | | | | | | |
| Brunetti | 97.8 | — | | | | | |
| Maxima | 96.9 | 97.1 | — | | | | |
| Mitis | 97.7 | 97.2 | 96.3 | — | | | |
| Necatrix | 97.4 | 96.5 | 95.5 | 96.5 | — | | |
| Praecox | 98.5 | 97.9 | 97.5 | 97.5 | 97.5 | — | |
| Tenella | 97.5 | 96.5 | 96.1 | 96.4 | 99.3 | 97.4 | — |

Table 2 illustrates examples of divergent segment probes useful for the specific identification of Eimeria. The probes listed in Table 3 derive from areas of nucleotide sequence within the small subunit ribosomal RNA genes which diverge among species and so, using appropriate hybridization and wash conditions (i.e., high stringency), are species-specific. Minor changes in the sequence of these probes (e.g.: deletion or addition of nucleotides from the ends), will not necessarily eliminate the species-specific feature especially if subtle changes in the hybridization temperature ($T_H$) are similarly incorporated as per the following equations: $T_h = T_m - 5°$ C. $= 2°$ C.(A − T bp) + 4° C.(G − C bp) − 5° C. (Suggs et al., In D. D. Brown (ed.), ICN-UCLA Symp. Dev. Biol. Using Purified Genes. Academic Press, Inc. N.Y. Vol. 23, pp. 683-693 [1981]) and $Tm = \Delta H/(\Delta S + R \times \ln(C/4)) - 273.15°$ C. (Freier et al., Proc. Natl. Acad. Sci. USA 83: 9373-9377[1986]). It is understood that the invention will also include oligonucleotides which are inverse complements of the sequences in Table 1. The inverse sequences represent perfectly satisfactory species-specific hybridization probes against DNA targets.

The following general PCR amplification oligonucleotide priomers were chosen for E. brunetti:

| 5'-AAACTTAAAGGAATTGACGG-3'<br>SEQ ID NO: 44 | ERIB 7 |
|---|---|
| 5'-CGGTGTGTACAAAGGGCAGG-3'<br>SEQ ID NO: 45 | ERIB 8 |

Each of these oligonucleotides is derived from conserved domains of ssrRNA genes and accordingly, are general PCR amplification primers. The primers span a length of approximately 508 nucleotides corresponding to nucleotide position 1240 to 1748 in the full length E. brunetti sequence (see FIG. 2B). These two oligonucleotides were used as primers in a PCR reaction which targeted E. brunetti genomic DNA as the amplification substrate using conditions described earlier for the full length products. The resulting PCR reaction product was cloned into the bacterial plasmid vector pUC120 as described above. Bacterial clones harboring recombinant plasmids with the appropriate size insert were identified and two of these were sequences using the Sanger chain termination method as described above. The nucleotide sequence of these clones was identical and is entered as Table 2 entitled E. brunetti fragment 4. The nucleotide sequence for the E. brunetti specific hybridization probe pEB4e-rc (SEQ ID NO:36) is complementary to nucleotide positions 224 to 244 in E. brunetti fragment 4, Table 2.

TABLE 2

Eimeria brunetti fragment 4

| | | | | |
|---|---|---|---|---|
| AAACTTAAAG | GAATTGACGG | AGGGGCACCA | CCAGGCGTGG | 40 |

TABLE 2-continued

*Eimeria brunetti* fragment 4

| | | | | |
|---|---|---|---|---|
| AGCCTGCGGC | TTAATTTGAC | TCAACACGGG | GAAACTCACC | 80 |
| AGGTCCAGAC | ATGGGAAGGA | TTGACAGATT | GATAGCTCTT | 120 |
| TCTTGATTCT | ATGGGTGGTG | GTGCATGGCC | GTTCTTAGTT | 160 |
| GGTGGAGTGA | TCTGTCTGGT | TAATTTCGAT | AACGAACGAG | 200 |
| ACCTTGGCCT | GCTAAATAGG | GTCGGTGACT | TTGGTTACCG | 240 |
| TATCGCTTCT | TAGAGGGACT | TTGCGTGTCT | AACGCAAGGA | 280 |
| AGTTTGAGGC | AATAACAGGT | CTGTGATGCC | CTTAGATGTT | 320 |
| CTGGGCTGCA | CGCGCGCTAC | ACTGATGCAT | GCAACGAGTT | 360 |
| TTTACCTTGA | CCGACGGGGC | TGGGTAATCT | TGTGAGGGTG | 400 |
| CATCGTGATG | GGGATAGATT | ATTGCAATTA | TTAGTCTTCA | 440 |
| ACGAGGAATG | CCTAGTAGGC | GCAAGTCAGC | ACTTGCGCCG | 480 |
| ATTACGTCCC | TGCCCTTTGT | ACACACCG | | 508 |
| (SEQ ID NO: 50) | | | | |

Live coccidiosis vaccines are produced using oocysts from attenuated strains of Eimeria. An example can include, but is not limited to, seven or more avian Eimeria species such as: *E. acervulina, E. tenella, E. maxima, E. necatrix, E. praecox, E. mitis, E. brunetti*. An immunogenic dose of oocysts from each species is combined, beaded in wax and covered with gypsum. An immunogenic dose refers to a dosage of each species which in combination prevents coccidiosis induced by one or more species. One day old female SPF Leghorn chicks are housed in isolator cages and given non-vaccine containing feed and water ad libitum until two weeks of age. Feed is removed on the day prior to administration of the vaccine. Vaccine beads are weighed and aliquots equivalent to 0.25 times, 0.5 times, 1 times, 2 times, 3 times, 5 times and 10 times the vaccine dose are mixed with feed (15 g/chick) and presented to the chicks in groups of from between about eight to about fifteen animals. All vaccine should be consumed within four hours. After the vaccine is fully consumed, vaccine-free feed is administered. A group of about 8 to 10 untreated birds are fed regular feed and water ad libitum for the duration of the experimental regimen. One to 3 additional groups of about 8 to about 15 birds is dosed by gavage with the the same number of unencapsulated oocysts (1X, 3X and 10X) and fed vaccine free feed ad libitum. These birds will represent a positive control for infection as well as serving to check the viability of organisms following encapsulation since the unencapsulated oocysts will be from the same production batch as those in the vaccine. Three to five days following administration of the vaccine or unencapsulated oocysts, intestinal epithelial and mucosal scrapings are prepared from the intestinal walls of the birds. Total nucleic acids extracted from these scrapings serve as the target or template in this protocol. The relative infectivity of each species of Eimeria subsequent to the encapsulation process is estimated based upon the ability to detect an amplification of the number of input oocysts. This is accomplished using species-specific $^{32}P$-labeled oligonucleotide hybridization probes. Some of the birds in each treatment group are sacrificed and used for fecal oocyst counts from days four to seven post-infection. Quantitation is based on a standard curve using genomic DNA prepared from cloned vaccine strain oocysts.

Preparation of total nucleic acids is carried out with the following method. It is important to take precautions not to introduce nucleases into the process, e.g. when possible use baked glassware or use plastic and autoclaved solutions where appropriate. Chickens are sacrificed 3-5 days after receiving a vaccine dose. The intestine and the ceca are removed, cut along their length and rinsed with tap water. The interior wall of the intestine and ceca are scraped/stripped with a microscope slide. Scrapings are transferred to a 50 ml centrifuge tube containing about 5 to 10 ml of 2X Proteinase K digestion buffer (about 400 mM Trim-HCl, pH 7.6, about 100 mM EDTA, about 1.0 % SDS). The suspension is mixed vigorously on a vortex mixer. About 200 μl of about 5 mg/ml Proteinase K is added to the suspension and it is allowed to digest at about 55° C. for about 3 hours. If viscosity is a problem at this point, add about another 5 ml of digestion buffer. Add about 100 μl of 5 mg/ml Proteinase K and continue digestion overnight. Following the overnight digestion, about 100 μl of 5 mg/ml Proteinase K is added and digestion is continued for up to 24 hours. Remove about 600 μl of the digest to a 1.5 ml microfuge tube and extract about twice with about a 1:1 mix of buffer equilibrated phenol and chloroform. Then extract with about a 24:1 mix of chloroform and isoamyl alcohol. The final aqueous phase may be stored at $-20°$ C. An aliquot of the final aqueous phase is ethanol precipitated. In most cases about 200 μl of the final aqueous phase is added to about 20 μl of 3M sodium acetate (pH 4.6) and then combined with about 500 μl of ethanol. The samples are mixed by inversion and placed in a dry ice ethanol bath for about 20 minutes. The genomic DNA is then collected by centrifugation in an Eppendorf microcentrifuge for about 15 minutes. The precipitate is washed once with about 70% ethanol and dried in a Speed-Vac. The precipitate is suspended in about 200 μl of deionized water. The amount of DNA in this total nucleic acid preparation is estimated using bisbenzimide which is a fluorochrome whose properties change when bound to DNA as discussed before. Salmon testes DNA standards from 0 to 20 μg/100 μl TE are made from a stock solution. Prepare the dilutions in 12×75 mm borosilicate tubes using sterile tips; change tips between dilutions. Similarly, make 1:10 dilutions to a final volume of about 100 μl for each experimental sample in duplicate. A bisbenzimide dye stock at a concentration of about 200 μg per ml in sterile water and stored at 4° C. in a dark bottle is stable for up to 6 months. Prior to use, dilute the dye stock 1:200 with a buffer whose composition is about 50 mM sodium phosphate, pH 7.6, 2M NaCl. Add about 2 ml of this to each borosilicate tube with an Eppendorf repeater pipette, mix and measure directly in a fluorocolorimeter at an excitation wavelength of 356 nm and an emission wavelength of 458 nm. Determine the amount of DNA in the experimental samples after calibrating the machine with standards.

PCR amplification of ssrRNA sequences from genomic DNA prepared from chicken intestinal mucosal scrapings is carried out in the following manner. Due to the exquisite sensitivity of this technique, extreme caution must be exercised to avoid contamination. Dedicated pipettes, pipette tips, vessels and stock solutions for DNA preparation, reaction assembly and sample analysis are recommended. Ideally, this should be done in areas separate from other DNA handling. About 200 ng of experimental genomic DNA based upon the bisbenzimide assay above is used as the starting target material. It is critical that this material first be ethanol precipitated to remove solvents remaining from the extractions which inhibit the Taq DNA polymerase. Genomic DNA prepared from known numbers of purified organisms from each of the species of Eimeria are used to "spike" about 200 ng of chicken hepatic genomic DNA. These will serve as amplification standards and hybridization specificity standards. Prepare a daily working solution of Tris-HCl buffered (pH 7.6) deoxynucleoside triphosphates dATP, dCTP, dGTP and dTTP each at about 1.25 mM from about 100 mM stocks stored at $-20°$ C. Prepare a 10x reaction buffer composed of about 100 mM Tris- HCl, pH 8.3, about 500 mM KCl, about 15 mM $MgCl_2$, about 0.01% gelatin and autoclave. This is aliquoted and stored at about $-20°$ C. The reaction mixture is assembled in dedicated PCR reaction tubes in a final volume of about 100 μl. First, a reaction mixture cocktail is prepared by mixing the following components at these final concentrations in this specific order: water, dATP, dCTP, dGTP and dTTP (dNTPs each at about 200 μM), 1X reaction buffer, and about 1 μM of each of the two amplification primers (ERIB 1 and ERIB 2) (SEQ ID NO:1 and SEQ ID NO:3) or any other suitable primers which flank a non-consensus region, mix, and add about 1.25 U Taq DNA polymerase per reaction tube and invert to mix. Other primers include, but are not limited to:

| | |
|---|---|
| ERIB 2 (SEQ ID NO: 3) | TCCCTCTCCGGAATCGGAC |
| 5 ERIB (SEQ ID NO: 4) | CCAGGTCCAGACATGG |
| 3 ERIB (SEQ ID NO: 5) | CTTGCGCCTACTAGGC |
| 5AERIB (SEQ ID NO: 31) | GTCGCAAGGCTGAAAC |
| 3AERIB (SEQ ID NO: 32) | CTTGCGCCTACTAGGC |
| 5BERIB (SEQ ID NO: 33) | GGGGGGAGTATGGTCTGCAAGGC |
| 3BERIB (SEQ ID NO: 34) | GCATGCATCAGTGTAGCTGCGCG |

Primer ERIB 1 (SEQ ID NO:1) is used with primer ERIB 2 (SEQ ID NO:2) and primer 5 ERIB (SEQ ID NO:4) is used with primer 3 ERIB (SEQ ID NO:5). Primer 5AERIB (SEQ ID NO:31) is preferably used with primer 3AERIB (SEQ ID NO:32) and primer 5BERIB (SEQ ID NO:33) is preferably used with primer 3BERIB (SEQ ID NO:34), however, any primer begining with 5' could also be used with any primer begining with 3'. An aliquot of about 80 μl of the cocktail is then distributed to each reaction tube. Based on the bisbenzimide DNA assay described above, about 200 ng of experimental genomic DNA is adjusted to a final volume of about 20 μl with distilled water and added to the reaction mixture. When amplifying using primers ERIB1 (SEQ ID NO:1) and ERIB2 (SEQ ID NO:3), the reactions are run in the BIOS thermal cycler. Generally the BIOS thermal cycler will be programmed as follows:
 a) about 3 cycles consisting of about 94° C. for about 1 minute to denature, about 50° C. for about 30 seconds to anneal and about 72° C. for about 45 seconds for polymerization;
 b) about 27 cycles consisting of about 94° C. for about 20 seconds to denature, about 50° C. for about 30 seconds to anneal and about 72° C. for about 45 seconds for polymerization;
 c) about one cycle at about 72° C. for about 10 minutes.

When amplifying using primer pairs 5AERIB/3AERIB (SEQ ID NO:31)/(SEQ ID NO:32) and 5BERIB/3BERIB (SEQ ID NO:33)/(SEQ ID NO:34), the reactions are run in the Perkin Elmer Cetus DNA thermal cycler. The reactions are set up as described above for the primer pair ERIB1/ERIB2 (SEQ ID NO:1)/(SEQ ID NO:3), except that after addition of the experimental genomic DNA, the reaction is overlayed with approximately 50 μl of light mineral oil and then placed into the Perkin Elmer Cetus DNA thermal cycler programmed as follows:
 a) about 3 cycles consisting of about 94° C. for about 1 minute to denature, about 48° C. for about 1 minute to anneal and about 72° C. for about 1 minute for polymerization;
 b) about 32 cycles consisting of about 94° C. for about 1 minute to denature, about 50° C. for about 1 minute 30 seconds to anneal and bout 72° C. for about 2 minutes for polymerization;
 c) about one cycle at about 72° C. for about 10 minutes. About 5 μl of the reaction product is then assayed for DNA content using a small scale bisbenzimide assay analogous to that described above. Exceptions are that dilutions are done in microcentrifuge tubes in duplicate, the final assay volume is about 500 μl, the sample is read in a microcell and the standard curve is linear from about 5 to 200 ng/ml.

Generally, about 100 ng of the PCR product quantitated as described above and adjusted to a final volume of about 100 μl with water, is applied to Nytran sheets (prewetted in water) in a slot-blot or dot-blot manifold as described in the manufacturer's specifications (Schleicher and Schuell, Inc.). To each sample is added 1 volume of 1M NaOH. The samples are then incubated at about room temperature for about 5 minutes to denature the DNA and neutralized by adding about 1 volume of 1M Tris-HCl (pH 7.3). A vacuum is then applied to the apparatus to filter the samples. Each sample is then rinsed with about 500 μl of 4M ammonium acetate (pH 6.8). Genomic DNA prepared from purified organisms of each of the avian Eimeria species is PCR amplified as described previously and is used to "spike" chicken hepatic genomic DNA also PCR amplified as described previously. The spiked DNA is also applied to the filters to serve as a species-specific quantitation standard. Appropriate buffer controls and blank controls are routinely included. Air dry the filters and bake under vacuum at about 80° C. for about 2 hours.

Oligonucleotide hybridization probes are labeled for quantitative determination of parasite viability. The preferred method is to end label the oligonucleotides with gamma $^{32}P$-ATP. Other methods known in the art can also be used. Quantitate and standardize oligonucleotides (1 mg/ml=25 $A_{260}$). Add about 5-10 pmoles of oligonucleotide to at least a two fold molar excess of gamma $^{32}P$-ATP (specific activity >5000 Ci/mmol), about 5 μl of 10X kinase buffer(about 0.5 Tris-HCl, about pH 7.6, about 0.1M $MgCl_2$, about 50 mM DTT, about 1 mM spermidine, about 1 mM EDTA) and a quantity of water sufficient to achieve a 50 μl reaction volume following the addition of 20 U of polynucleotide kinase. Incubate the mixture for about 30 minutes at about 37° C. Stop the reaction by the addition of about 4 μl of 0.5M EDTA, about 46 μl of TE. Extract once with a 1:1 mixture of buffer equilibrated phenol and chloroform. Pass the aqueous phase through a Stratagene push column (Stratagene) as per the manufacturer's specifications to remove the unincorporated isotope from the labeled oligonucleotide.

Prehybridization, hybridization and washes are carried out in the following manner. Prehybridization is done in a buffer whose composition is about 6X SSPE, 1% SDS, 10X Denhardt's, about 20 to 100 μg per ml tRNA, and either with or without 50 μg per ml denatured salmon sperm DNA. SSPE consists of about 180 mM NaCl, 10 mM NaH$_2$PO$_4$, 1 mM EDTA. The buffer is made and kept at 42° C. until ready for use to keep the SDS in solution. The dry sheet(s) of Nytran are prewetted in 6X SSPE, placed in a polyethylene freezer bag which is heat sealed on three sides. The heterologous DNA is denatured in a boiling water bath for 10 minutes, quick chilled on ice and mixed with the prehybridization solution (20–40 ml depending on the number of sheets of Nytran in the bag). The prehybridization solution is added to the bag, air bubbles removed, and the bag is sealed on the fourth edge. The bag is then secured to a glass plate with elastic bands and submerged in a water bath at 42° C. for at least 3 hours or for as long as overnight. Following prehybridization the bag is cut open and the buffer is removed completely. The hybridization buffer is about 6X SSPE plus about 1% SDS. Hybridization is done at or about the $T_h$ of the desired hybrid. For probes less than 25 nucleotides in length, hybridization conditions are determined using either of the following formulae:

$$T_h = T_m - 5° \text{ C.} = 2° \text{ C.}(A - T \, bp) + 4° \text{ C.}(G - C \, bp) - 5° \text{ C.}$$

(Suggs et al., In D. D. Brown (ed.), ICN-UCLA Symp. Dev. Biol. Using Purified Genes. Academic Press, Inc. N.Y. Vol. 23, pp. 683-693 [1981])

$$Tm = \Delta H(\Delta S + R \times ln(C/4)) - 273.15° \text{ C.}$$

(Freier et al., Proc. Natl. Acad. Sci. USA 83: 9373-9377[1986]).

The end labeled oligonucleotide probe is warmed at 68° C. for 5 min prior to mixing with 10–20 ml (depending on the number of filters per bag; approx. 1–5×10$^6$ dpm/ml) of hybridization buffer which is prewarmed at the $T_h$. This is poured into the bag, air bubbles are removed and the bag is resealed. The bag is secured to a glass plate and submerged in a water bath at the $T_h$ for at least 12 hours to overnight. Following hybridization, cut open the bag and discard the buffer. Cut the remaining three sides of the bag and with forceps remove the filter(s) to a pyrex dish containing the first wash solution. The washes are as follows:
  a) about 3 times for 5–10 minutes each in 6X SSPE, 1% SDS at 37° C. with shaking;
  b) about one time for 3 min in 1X SSPE, 1% SDS at the Th of the hybrid;
  c) about 3–4 times for approx. 5 min each in 6X SSPE at room temperature with shaking to remove the SDS.

Wash volumes should be at least 100 ml to cover the filters; use more with multiple filters. All wash solutions should be prewarmed at the respective temperatures prior to use. Air dry the filters, place in a cassette which contains two intensifying screens and expose to X-ray film at −70° C. Develop the film after 1–3 days.

Quantitation of hybridization signal is carried out using the Molecular Dynamics PhosphorImager (Molecular Dynamics). Dried blots are placed beneath plastic wrap in the PhosphorImager cassette as per the manufacturer's instructions and exposed to the phosphor screen for approximately 2 hours for the common hybridization probe and 3–12 hours for the specific Eimeria probes. The screen is then scanned with a laser which releases the energy captured by the phosphor in the screen. The released energy is quantitated by the machine.

Eimeria RNA can also be isolated and used to determine the presence and concentration of multiple species of Eimeria in a sample. Isolation of Eimeria RNA from chicken intestines must be carried out with care to avoid degradation of the RNA. One successful protocol is essentially the same as published in Chirgwin et al., Biochemistry 18(1979) 5294-5299. Mucosal scrapings from chickens vaccinated 3–5 days previously are taken and transferred to a 50 ml centrifuge tube as is described earlier. These scrapings are immediately placed into about 24 ml of about 4M guanidine thiocyanate, pH 7.0, about 0.5% sodium N-lauroylsarcosine, about 25 mM sodium citrate, about 0.1M 2-mercaptoethanol, and about 0.1% Sigma 30% Antifoam A. The samples are quickly homogenized with a Polytron (Brinkmann) at full speed three times for 20 seconds; between samples the Polytron is rinsed 2 times with sterile distilled water. The samples are then centrifuged at approximately 8,000 RPM for 10 minutes at about 10° C. in a swinging bucket rotor e.g. JS-13 (Beckman). The supernatants are decanted and the pellets are precipitated with about 0.6 ml of about 1M acetic acid and about 18 ml of 100% ethanol at −20° C., overnight. The samples are centrifuged again at 8,000 RPM, for 10 minutes at 10° C. The pellets are resuspended in about 12 ml of approximately 7.5M guanidine hydrochloride, pH 7.0, 25 mM sodium citrate, and 5 mM dithiothreitol, shaken vigorously, and heated to 68° C. until dissolved. The samples are precipitated with approximately 0.3 ml of 1M acetic acid and about 6 ml of 100% ethanol at −20° C., overnight. Again the samples are centrifuged, resuspended, and precipitated as before, except with one-half the previous volumes, i.e. 6 ml, 0.15 ml, and 3 ml respectively. The samples are pelleted once again, triturated with about 10 ml of room-temperature 95% ethanol, transferred to baked Corex centrifuge tubes, and repelleted at about 10,000 RPM for about 30 minutes at about 10° C. The RNA pellets are dried under vacuum in a Speed-Vac (Savant Instruments), dissolved at about 68° C. in about 2 ml diethyl pyrocarbonate-treated sterile distilled water, repelleted, re-extracted with about 1 ml diethyl pyrocarbonate-treated sterile distilled water, and repelleted again. The extractions are reprecipitated with about 300 μl of 2M potassium acetate, about pH 5.0, and about 8 ml of 100% ethanol at −20° C. overnight. The final RNA preparations are pelleted and resuspended in about 1 ml of diethyl pyrocarbonate-treated sterile water. Absorbance readings at 260 nm and 280 nm (Beckman spectrophotometer) are taken to determine RNA concentrations; about 3 μg of RNA are then subjected to electrophoresis on about a 1.2% agarose gel to check the RNA quality, size, and relative concentration. RNA samples can be stored at −70° C. The RNA is treated with DNase which is free of RNase (i.e. RQ1 DNase, Promega) as per manufacturers directions, except digestion is carried out for about 30-40 minutes at about 37° C. The sample is extracted with about equal volumes of phenol/chloroform and precipitated with about 1/10 volume of about 3M sodium acetate and about 2 ½ volumes of ethanol at about −70° C. overnight. The RNA pellet is recovered by centrifugation, washed with about 75% ethanol, dried under vacuum and resuspended in diethyl pyrocarbonate-treated sterile water. Twenty to thirty micrograms of RNA are slotted in duplicate onto Nytran filters after denaturing the RNA in 1X denaturing solution (4X denaturing solution contains about 1 ml of formaldehyde, 56 μl of 1M sodium phosphate, pH 6.5, and 344 μl of sterile distilled water) at 68° C. for about 20 minutes. The denatured samples are immediately placed on ice to cool and then immobilized onto Nytran filters with a slot/dot-blot manifold as per manufacturers directions (BioRad Laboratories, Inc.). The nylon filters are baked at about 80° C. for about 30 to 60 minutes. These filters are then prehybridized, hybridized and washed as per manufacturers specifications (Schliecher and Schuell, Inc.) for oligonucleotide probes for Northern (RNA) transfers. The oligonucleotide probes are $^{32}P$ end labelled as previously described.

Genomic DNA from fecal oocysts can also be isolated and used to determine the presence and concentration of multiple species of Eimeria in a sample. The feces is diluted about ten fold in distilled water and then the contents are passed through a sieving device. A series of passes through screens of decreasing size functionally removes a considerable amount of fecal debris. Partially pure oocyst fractions of the Eimeria species are then collected by flotation in about 2.2M sucrose (Jackson, Parasitol. 54: 87-93 [1964]), and further treated by incubation in sodium hypochlorite at a concentration of 5.25%, in water at about 40° C. for about 10 minutes. The sodium hypochlorite is removed by several washes in sterile phosphate buffered saline (PBS) at about pH 7.6 to obtain purified, sterile oocysts. Depending upon the species, oocysts are allowed to sporulate in a shaking water bath for about 24 to about 60 hours at about 20° C. (Edgar,Trans. Am. Micr. Soc. 62: 237-242 [1954]) in PBS or sterile water. Following sporulation, oocysts are washed several times in sterile PBS.

Sporulated oocysts are disrupted by shaking with 3 mm sterile glass beads. Beads are added to the oocyst suspension and the mixture is mixed vigorously on a Vortex mixer for about 2 minutes. Periodically the extent of breakage is assessed microscopically. When approximately 50% breakage has occurred, the glass beads are allowed to settle and the sample above the beads is removed and mixed with an equal volume of Percoll (Pharmacia). The disrupted oocysts are subjected to centrifugation at about 2,000×g for about 10 min at about 4° C. to pellet the enriched sporocyst fraction. Unbroken oocysts form a layer on top of the 50% Percoll and are removed, washed in PBS, mixed with glass beads and mixed again as described above. This procedure is performed repeatedly (3-4 times) until very few unbroken oocysts remain following Percoll fractionation. Sporocyst pellets are combined and washed several times in PBS.

Sporocysts are then diluted in 0.01 M Tris (pH 8.0), 0.2M NaCl to a concentration of approximately $10^8$ per ml and the suspension is adjusted to about 1% sodium dodecyl sulfate (SDS) and about 10 mM EDTA which results in membrane lysis. The released genomic DNA is solubilized by digestion with Proteinase K (150 μg/ml) for approximately 30 minutes at about 55° to 65° C. Genomic DNA is extracted twice with buffer equilibrated phenol (about pH 7.6), twice with a mixture of phenol/chloroform/isoamyl alcohol at about 25:24:1, and twice with chloroform/isoamyl alcohol at about 24:1. The final aqueous phase is dialyzed overnight in 10 mM Tris (pH 8.0), 10 mM NaCl, 10 mM EDTA (pH 8.0). RNA which has co-purified with the DNA is selectively removed from the dialysate by digestion with heat inactivated RNase A used at a concentration of about 150 μg/ml. The samples are incubated for about 1 hour at about 37° C. The RNase and other residual proteins are removed by a secondary digestion with Proteinase K (about 150 μg/ml, for about 30 minutes at about 37° C.). The genomic DNA is then successively extracted with organic solvents as described above. The final aqueous phase is precipitated with about 0.1 volumes of about 3M sodium acetate and about 2.5 volumes of about 100% ethanol. Glycogen is added to 20 μg/ml to act as carrier. The pellets are washed twice with about 70% ethanol. The genomic DNA pellet is air dried by inversion and is then suspended in about 10 mM Tris.HCl (pH 7.6), 1 mM EDTA buffer (TE) or distilled water at a concentration of about $5-8 \times 10^8$ sporocyst equivalents/ml and quantitated by absorbance at 260 nm and/or using the afformentioned bisbenzimide assay. An aliquot of DNA is then analyzed by agarose gel electrophoresis to confirm; (i) the spectrophotometric generated concentration, (ii) the lack of residual RNA, and (iii) it's high molecular weight integrity.

Equivalent amounts of genomic DNA based on the bisbenzimide assay are denatured and immobilized on eight identical sheets of Nytran paper for hybridization. Generally, about 100 ng of the genomic DNA quantitated as described above is adjusted to about 100 μl with water, to which is added about 0.1 volume of about 3M NAOH. This is incubated at about 70° C. for about 30-60 minutes to denature the DNA, cooled at room temperature, neutralized by adding about 1 volume of about 2M ammonium acetate (pH 7.0) and applied to Nytran sheets in a slot-blot or dot-blot manifold as per the manufacture's specifications (Schliecher and Schuell, Inc.). A vacuum is applied to filter the samples. Genomic DNA prepared from known numbers of purified organisms from each of the species of Eimeria is also applied to the filters to serve as a species-specific quantitation standard. Appropriate buffer controls and blank controls are routinely included. The filters are air dried and baked under vacuum at about 80° C. for about 2 hours. The prehybridization, oligonucleotide hybridization, washes and the quantitation of hybridization is carried out as described above.

The following examples illustrate the invention without, however, limiting the same thereto.

EXAMPLE 1

Method For Cloning Eimeria Species Small Subunit Ribosomal RNA Genes

Oocysts from laboratory strains of *E. acervulina, E. brunetti, E. maxima, E. mitis, E. necatrix, E. praecox* and *E. tenella* were propagated by oral infection of broiler chickens. *Eimeria tenella* oocysts were isolated from the cecal contents of chickens at 5-7 days post-infection. The remaining Eimeria species were individually isolated from fecal collections 3-8 days following infection. The cecal contents were physically disrupted in a Waring Blender, in distilled water and digested with pepsin. Following digestion, debris was removed by centrifugation in distilled water. The feces was diluted ten fold in distilled water and then the contents were passed through a sieving device. A series of passes through screens of decreasing size functionally removed a considerable amount of fecal debris. Partially pure oocyst fractions for each of the seven Eimeria species were then collected by flotation in 2.2 M sucrose (Jackson, Parasitol. 54: 87-93 [1964]), and further treated by incubation in sodium hypochlorite at a concentration of 5.25% in water at 40° C. for 10 minutes. The sodium hypochlorite was removed by several washes in sterile phosphate buffered saline (PBS) at pH 7.6 to obtain purified, sterile oocysts. Depending upon the species, oocysts were allowed to sporulate in a shaking D water bath for 24 to 60 hours at 20° C. (Edgar,-Trans. Am. Micr. Soc. 62: 237-242 [1954]) in PBS or sterile water. Following sporulation, the oocysts were washed several times in sterile PBS.

Sporulated oocysts were disrupted using 3 mm sterile glass beads. Beads were added to the oocyst suspension and the mixture was mixed vigorously on a Vortex mixer for approximately 2 minutes. Periodically the extent of breakage was assessed microscopically. When approximately 50% of the sporulated oocysts were disrupted, the glass beads were allowed to settle and the sample above the beads was removed and mixed with an equal volume of Percoll (Pharmacia). The disrupted oocysts were subjected to centrifugation at 2,000×g for 10 min at 4° C. to pellet the enriched sporocyst fraction. Unbroken oocysts forming a layer on top of the 50% Percoll were removed, washed in PBS, mixed with glass beads and mixed again as described above. This procedure was performed repeatedly (3-4 times) until very few unbroken oocysts remained following Percoll fractionation. Sporocyst pellets were combined and washed several times in PBS.

Sporocysts were then diluted in 0.01M Tris (pH 8.0), 0.2M NaCl to a concentration of approximately $10^8$ per ml and the suspension was adjusted to 1% sodium dodecyl sulfate (SDS) and 10 mM EDTA which resulted in membrane lysis. The released genomic DNA was solubilized by digestion with Proteinase K (150 μg/ml) for approximately 30 minutes at 65° C. Genomic DNA was extracted twice with buffer equilibrated phenol (pH 7.6), twice with a mixture of phenol/chloroform/isoamyl alcohol at 25:24:1, and twice with chloroform/isoamyl alcohol at 24:1. The final aqueous phase was dialyzed overnight in 10 mM Tris (pH 8.0), 10 mM NaCl, 10 mM EDTA (pH 8.0). RNA which had co-purified with the DNA was selectively removed from the dialysate by digestion with heat inactivated RNase A used at a concentration of 150 μg/ml. The samples were incubated for 1 hour at 37° C. The RNase and other residual proteins were removed by a secondary digestion with Proteinase K (150 μg/ml, for 30 minutes at 55° C.). The genomic DNA was then successively extracted with organic solvents as described above. The final aqueous phase was precipitated with 0.1 volume of 3M sodium acetate and 2.5 volumes of 100% ethanol. Glycogen was added to 20 μg/ml to act as carrier. The pellets were washed twice with 70% ethanol. The genomic DNA pellet was air dried by inversion and was then suspended in 10 mM Tris.HCl (pH 7.6), 1 mM EDTA buffer (TE) or distilled water at a concentration of $5-8 \times 10^8$ sporocyst equivalents/ml and quantitated by absorbance at 260 nm. An aliquot of DNA was then analyzed by agarose gel electrophoresis to confirm (i) the spectrophotometric generated concentration, (ii) the lack of residual RNA, and (iii) its high molecular weight integrity.

The ribosomal RNA (rRNA) gene loci harbor a wealth of information that has been successfully used to establish phylogenetic relationships among and within eukaryotic kingdoms (Hasegawa et al., J. Mol. Evol. 22: 32-80 [1985]). Sequences of the ssrRNA from a number of highly divergent organisms have recently been compiled (Dams et al., Nucleic Acids Res. 16S: r87-r173 [1988], Neefs et al., Nucleic Acids Res. 18S: 2237-2317 [1990]). Comparative analysis of these nucleotide sequences revealed areas with dramatic sequence similarities and other areas that are characterized by considerable sequence drift. Regions close to both the 5'- and 3'-ends of the consensus small subunit rRNA (ssrRNA) sequence with near identity in the eukaryotic kingdom were chosen. Oligonucleotides corresponding to these sequences were chosen:

| | |
|---|---|
| 5'-ACCTGGTTGATCCTGCCAG-3' SEQ ID NO: 1 | ERIB 1 |
| 5'-CTTCCGCAGGTTCACCTACGG-3' SEQ ID NO: 2 | ERIB 10 |

The oligonucleotides were synthesized using an Applied Biosystems 380B instrument and purified as per the manufacturer's recommendations. ERIB 1 (SEQ ID NO:1) represents a consensus sequence less than 10 nucleotides from the 5'-end of eukaryotic ssrRNA genes. ERIB 10 (SEQ ED NO:2) is the inverse complement to a consensus sequence located approximately 20 nucleotides from the 3'-end of eukaryotic ssrRNA genes. Taken together, these two oligonucleotides span the vast majority of the ssrRNA gene sequence.

ERIB 1 (SEQ ED NO:1) and ERIB 10 (SEQ ID NO:2) were used as a primer pair in the polymerase chain reaction (PCR, Saiki et al., Science 239: 487-491 [1988]) with the intention of selectively amplifying the ssrRNA genes contained within the genomic DNA preparation of each of the seven Eimeria species as described above. Genomic DNA was quantitated using a fluorescent dye binding assay (Lebarca and Paigen, Anal. Biochem. 102: 344-352 [1980]) and diluted to a final concentration of 2.5 ng/μl for use as the PCR template. A 10X reaction buffer consisting of 100 mM Tris-HCl (pH 8.3), 500 mM KCl, 15 mM $MgCl_2$, 0.01% gelatin was prepared as well as 100 mM stocks of Tris-HCl (pH 7.6) buffered dATP, dCTP, dGTP and dTPP. The reaction mixture was prepared by mixing the following components at these final concentrations in this specific order: water, dATP, dCTP, dGTP and dTTP (each at 200 μM), 1X reaction buffer, 1 μM of each of the two oligonucleotide primers (ERIB 1 and ERIB 10)

(SEQ ID NO:1 AND SEQ ID NO:2), and 1.25 U Taq DNA polymerase. The reaction mixture was assembled in dedicated PCR reaction tubes by combining 90 μl of the reaction cocktail with 10 μl (25 ng) of genomic DNA. The reaction was overlayed with approximately 50 μl of light mineral oil and then placed into a Perkin Elmer Cetus DNA thermal cycler programmed as follows:

35 cycles each composed of (i) 94° C. for about 60 seconds to denature, (ii) 50° C. for about 90 seconds to anneal, and (iii) 72° C. for 120 seconds for polymerization;

1 cycle at 72° C. for 10 minutes for extension.

A 5 μl aliquot of the reaction product was subjected to agarose gel DNA electrophoresis in TAE buffer along with DNA size standards. A characteristic band approximately 1.8 kb in length, whose size is roughly predicted by analogy to other eukaryotic ssrRNA genes, suggested that ERIB 1 (SEQ ID NO:1) and ERIB 10 (SEQ ID NO:2) actually hybridized to the Eimeria ssrRNA genes and that Taq DNA polymerase synthesized a reaction product by extension from the 3'-ends of these primers.

By definition, the ends of the 1.8 kb PCR products correspond to the input oligonucleotides and should be blunt. However, Taq DNA polymerase is prone to adding single non-template-directed nucleotides, in particular dATP, to the 3'-end of duplex PCR products (J. M. Clarke, Nucleic Acids Res. 16: 9677-9686 [1988]). In order to increase cloning efficiency, the ends of the PCR products were "polished" to blunt-ends by the action of the Klenow fragment of bacterial DNA polymerase. Reaction products were extracted once with phenol, once with a phenol/chloroform/isoamyl alcohol mix and once with chloroform/isoamyl alcohol as described earlier. DNA was precipitated with sodium acetate/ethanol and the pellet was washed twice with 70% ethanol. For the Klenow fragment reaction, the DNA (1-10 μg) was suspended in 15 μl of water and mixed with 2 μl of 10X nick translation buffer (0.5M Tris-Cl [pH 7.2], 0.1M MgSO$_4$, 1 mM dithiothreitol, 500 μg/ml bovine serum albumin [BSA Pentax Fraction V]), and 2 μl of a 1.25 mM solution of all four dNTPs and 1 μl (=5 Units) Klenow. The reaction was conducted at 14° C. for 1 hour and was terminated by heating at 65° C. for 10 minutes. The polished 1.8 kb DNA products were passed over a G 25 column, extracted once with phenol, and twice with chloroform/isoamyl alcohol as described earlier. The DNA was precipitates with sodium acetate/ethanol and the pellet was washed twice with 70% ethanol. The DNA was resuspended in 36 μl of water and mixed with 4 μl of 0.2M Tris.HCl (pH 9.5), 10 mM spermidine, 1 mM EDTA. This reaction mixture was incubated at 70° C. for 5 minutes and subsequently rapidly chilled on ice. To the above 40 μl are added 5 μl of 10X blunt end kinase buffer (0.5M Tris-Cl [pH 9.5], 0.1M MgCl$_2$, 50 mM dithiothreitol, 50% glycerol), and 5 μl of a 10 mM solution of ATP and 2 μl (=20U) of T4 polynucleotide kinase. The reaction was conducted at 37° C. for 30 minutes and was terminated by the addition of 2 μl of 0.5 M EDTA. The reaction mixture was brought to about 100 μl with TE buffer and the reaction products were extracted once with phenol, once with phenol/chloroform/isoamyl alcohol mix and once with chloroform/isoamyl alcohol as described previously. DNA was precipitated with sodium acetate/ethanol and the pellet was washed twice with 70% ethanol, as above. The DNA is resuspended in 20 μl of water and quantitated by absorbance at 260 nm.

The polished 1.8 kb DNA products were then subjected to agarose gel electrophoresis to separate the residual oligonucleotide primers and nonspecific PCR products from the polished 1.8 kb products. Gel slices containing the bands of interest were excised, melted and the DNA eluted using Geneclean II (BIO 101 Inc., Vogelstein and Gillespie, Proc. Natl. Acad. Sci. USA 76: 615-619 1979) as per the manufacturer's instructions. Eluted DNA products were then quantitated by absorbance at 260 nm.

A phagemid cloning vector pUC120 (Vieria, *Bireplicon Filamentous Phages and the Production of Single Stranded Plasmid DNA*. Ph.D. thesis, University of Minnesota [1989]) is cut at it's unique Sma I site in the polylinker. Other suitable cloning vectors include but are not limited to the pGEM-Zf series (Promega Corporation) and the pBluescript II series (Stratagene Cloning Systems). Cutting was monitored by analytical agarose gel electrophoresis. The linearized DNA was then extracted with organic solvents, precipitated and washed with 70% ethanol as described earlier. The 5'-end of each strand of the plasmid was phosphatased with calf intestinal phosphatase (CIP) to decrease the frequency of an autoligation event. This was accomplished by mixing the linearized plasmid (about 10 μg) with 5 μl of 10X CIP buffer (0.5 M Tris-HCl pH 9.0, 10 MM MgCl$_2$, 1 MM ZnCl$_2$, 10 mM spermidine) and 1 μl (1 Unit) of CIP in a final 50 μl reaction volume. The reaction was conducted for 15 minutes at 37° C. and then 15 minutes at 56° C. A second aliquot of CIP was then added and the reaction was repeated as above. The reaction was terminated by the addition of 40 μl of H$_2$O, 10 μl of 10X STE buffer (100 mM Tris-HCl, pH 8.0, 1M NaCl, 10 mM EDTA), 2.5 μl of 20% SDS and heated at 68° C. for 15 minutes. The linearized, phosphatased vector was then extracted, precipitated and washed as above.

Ligation of the gel purified ssrRNA gene PCR products into the blunt Sma I site within the pUC120 polylinker was then conducted. Approximately 100 ng of linearized vector was mixed with an equimolar amount of the respective PCR products in a 20 μl reaction mixture which, in addition is composed of 66 mM Tris-HCl, pH 7.6, 5 mM MgCl$_2$, 5 MM dithiothreitol, 1 mM ATP. The reaction was initiated by the addition of T4 DNA ligase and incubated for 12-16 hours at 14° C.

Competent bacterial cells capable of uptake of foreign DNA were prepared by the following method. A predetermined volume (about 2 ml per transformation reaction) of sterile 2X YT bacterial media (16 g bactotryptone, 10 g yeast extract, 5 g NaCl per liter) was inoculated with a single colony of Escherichia coli MV1184 and grown with vigorous mixing at 37° C. until it reached an optical density of 0.6 at 600 nm. Other suitable bacterial hosts include but are not limited to MN522, JM101, TB1 and XL1-Blue. Bacteria were collected by centrifugation at 1000×g, at 4° C., for 5 minutes. The resulting cell pellet was gently suspended in one-half of the original culture volume with sterile 50 mM CaCl$_2$ and the suspension was then placed on ice for 20 min. The cells were again collected by centrifugation and then gently suspended in one-tenth volume of sterile 50 mM CaCl$_2$. The bacterial suspension was then kept at 4° C. for 16-24 hours.

From the 20 μl ligation reaction mixture 2 μl and 18 μl aliquots were dispensed into sterile polypropylene tubes. Approximately 100 μl of competent bacteria were added to each of the tubes containing the ligation reactions (as well as the appropriate ligation and transformation controls) and these were placed on ice for 40 minutes. After this, the bacteria were "heat-shocked" by incubation at 42° C. for 90 seconds and then allowed to recover for approximately 5 minutes at room temperature. Each transformation tube was then plated onto a 2X YT agar plate which contains ampicillin at a concentration of 50 mg/l for the selection of bacteria harboring plasmids and for plasmid maintenance. Plates were incubated in an inverted position overnight at 37° C.

Bacterial clones harboring plasmids were identified by their ability to grow on plates in the presence of ampicillin. Single colonies were used to inoculate 5 ml of 2X YT/AMP (i.e., 2X YT media containing ampicillin at 50 mg/l) and these cultures were grown overnight at 37° C. with vigorous shaking. Approximately 1.5 ml of the culture was poured off into an Eppendorf tube and collected by centrifugation in an Eppendorf centrifuge for at least 1 minute; the remainder of the culture was stored at 4° C. and served as a genetic stock. The media above the bacterial pellet was aspirated off and the pellet was suspended by vortexing in 100 µl of a cold, freshly prepared solution of 50 mM glucose, 10 mM EDTA, 25 mM Tris-HCl (pH 8.0), 4 mg/ml lysozyme. This mixture was incubated at room temperature for 5 minutes. Then 200 µl of a cold, freshly prepared solution composed of 0.2N NaOH, 1% SDS was added to each tube, mixed gently by inversion, and put on ice for 5 minutes. To this mixture was added 150 µl of a cold, freshly prepared solution containing 6 ml of 5M potassium acetate, 1.15 ml of glacial acetic acid, 2.85 ml distilled water. The contents were gently vortexed and this mixture was stored on ice for 5 minutes. The cellular debris was collected by centrifugation in an Eppendorf centrifuge for 10 minutes at 4° 1 C. and the supernatant fluid was extracted one time with phenol/-chloroform/isoamyl alcohol (25:24:1). Plasmid DNA and cellular RNA were precipitated from the final aqueous phase with the addition of two volumes of 100% ethanol at room temperature. A pellet was collected by centrifugation for 5 minutes at room temperature, the pellet was washed one time with 70% ethanol and then dried briefly. The nucleic acid pellet was then suspended in 50 µl of TE containing 20 µl of DNase-free RNase per ml and incubated for 15-30 minutes at 37° C. to quantitatively eliminate cellular RNA. Aliquots of 10 µl were then cut to completion with Hind III and Eco R1 (each at approximately 20 units) in a buffer composed of 50 mM NaCl, 100 mM Trim-HCl (pH 7.5),5 mM MgCl$_2$ at 37° C. for 60 min. The restriction enzyme reaction products were separated by agarose gel electrophoresis to identify those plasmids which contained the appropriate inserts. Those recombinant plasmids which contained the predicted 1.8 kb insert were then cut with a second restriction enzyme (usually Pst I) to verify; (i) that only a single copy of the insert was contained within the plasmid, and (ii) to score for orientation of the insert DNA with respect to the bacterial promoter. This was accomplished by removing a second 10 µl aliquot from the remaining 40 µl of RNase-digested bacterial nucleic acid and cleaving it in a buffer composed of 100 mM NaCl, 10 mM Trim-HCl (pH 7.5), 10 mm MgCl$_2$ with approximately 20 units of Pst I for 60 min at 37° C. Again, the restriction enzyme digests were resolved by agarose gel electrophoresis.

The isolated and purified genes encoding the *E. acervulina, E. brunette, E. maxima, E. mitis, E. necatrix, E. praecox* and *E. tenella* small subunit ribosomal RNA are shown in FIGS. 1-7 respectively. The seven gene sequences were compared and regions of nucleotide divergence were identified. Oligonucleotides complimentary to these divergent regions were synthesized as described above and were used as hybridization probes as described below. Table 4 illustrates the primary divergent sequences for the various species of Eimeria. The sequences listed in Table 3 (except for those in the 'common' group) are examples of the most convenient species-specific hybridization probes, i.e. probes which were constructed to regions of the ssrRNA genes containing the maximal diversity of nucleotide sequence, resulting in maximal specificity.

TABLE 3

| Eimeria species | Probe Name | Sequence | |
|---|---|---|---|
| acervulina | WEaRC | CAGCCCACGCAATTAAGCGCAGGAG | (SEQ ID NO: 6) |
| | PEa4-RC | GAAGTGATACGATAACCGAAGTT | (SEQ ID NO: 7) |
| | PEa4e-RC | TACGATAACCGAAGTTACCG | (SEQ ID NO: 35) |
| brunetti | AEb1RC | CCCCTTCATAGAAAGGAAGCC | (SEQ ID NO: 8) |
| | AEb1aRC | CCCCTTCAAAGAAGGAAGCC | (SEQ ID NO: 9) |
| | PEb4-RC | TGCGTGACCGAGGTCA | (SEQ ID NO: 10) |
| | PEb4e-RC | GATACGGTAACCAAAGTCACC | (SEQ ID NO: 36) |
| maxima | WEmx1RC | CAAGACTCCACAAGAATTGTG | (SEQ ID NO: 11) |
| | PEmx4-RC | GATACGGTAACCGAGGTCAC | (SEQ ID NO: 12) |
| | PEmx4a-RC | GATACGGTAACCGAGGTCA | (SEQ ID NO: 37) |
| mitis | PEmt1RC | CCAGAGGAGGGCCTATGCG | (SEQ ID NO: 13) |
| | PEmt1aRC | CCAGAGGAGGAGGCCTATGCG | (SEQ ID NO: 14) |
| | PEmt4-RC | TGACCTGGTGACCCAGG | (SEQ ID NO: 15) |
| necatrix | WEn-1RC | CGTTAAGTGGGTTGGTTTTG | (SEQ ID NO: 16) |
| | WEn-1M | CAAAACCAACCCACTTAACG | (SEQ ID NO: 38) |
| | PEn4-RC | AAGTGATACAGTAATCGTGAAGTT | (SEQ ID NO: 17) |
| praecox | WEp1RC | CACCATGACTCCACAAAAGTG | (SEQ ID NO: 18) |
| | PEp4-RC | AGAAGTGATACAGTAACCGAAGTT | (SEQ ID NO: 19) |
| | Pep4d-RC | TGATACAGTAACCGAAGTTACTG | (SEQ ID NO: 39) |
| tenella | WEt1RC | CCAAGACTCCACTACAAAGTG | (SEQ ID NO: 20) |
| | PEt4-RC | GTGATACAGTAACCGCAAAGTT | (SEQ ID NO: 21) |
| | PEt4a-RC | TACAGTAACCGCAAAGTTACTG | (SEQ ID NO: 40) |
| common | CommonRC | AGCCATTCGCAGTTTCACCG | (SEQ ID NO: 22) |
| | Common4RC | AAGGTCTCGTTCGTTATCGA | (SEQ ID NO: 23) |
| | Com4A-RC | GGTCTCGTTCGTTAATCGAA | (SEQ ID NO: 41) |
| | COM4B-RC | CATCACAGACCTGTTATTGCC | (SEQ ID NO: 42) |
| | COM4C-RC | CATAGAACGGCCATGCA | (SEQ ID NO: 43) |

Other regions of the ssrRNA genes which can serve the same purpose are listed in Table 4. An indicator of ssrRNA sequence diversity was obtained by computer analysis of the sequences illustrated in FIGS. 1-7. The program PRETTY within the GCG (Univ. of Wisconsin) program package was used as an example of a multiple sequence alignment program. The objective of the algorithm of this program is to maximize the areas of homology between the sequences compared by making base by base comparisons and inserting gaps which correspond to additions or deletions as necessary to optimize the number of matches. FIG. 12 is an example of the output generated by 'PRETTY' using the sequences illustrated in FIGS. 1-7. Note that there is an additional line of sequence termed 'consensus.' This is a position by position report on the homology of the sequences compared. If all seven nucleotides match, a capital letter is used to identify that event. If a single difference is observed it is denoted by a(—) in the consensus sequence. It should also be noted that in this 'aligned' format, all seven species end up with a sequence length of 1766 bases, do to the insertion of various sized gaps. Thus the nucleotide numbering system in FIG. 12 is relative to the alignment program and program parameters used. Nucleotide segments of interest in the 'aligned' format must be cross referenced to the absolute sequence numbering system for each individual species.

TABLE 4

Regions Of The ssrRNA Gene From Chicken Eimeria Species Useful As Species-Specific Hybridization Probe Targets. Nucleotide Positions Relative To The 'Alignment' In FIG. 12.

| Region | Nucleotide Span |
| --- | --- |
| 1 | 106-114 |
| 2 | 154-180 |
| 3 | 189-227 |
| 4 | 257-272 |
| 5 | 636-733 |
| 6 | 932-939 |
| 7 | 1037-1052 |
| 8 | 1062-1068 |
| 9 | 1160-1173 |
| 10 | 1341-1392 |
| 11 | 1487-1529 |
| 12 | 1679-1716 |

Areas of the ssrRNA gene from the seven chicken Eimeria species, which have diverged during the course of evolution can be identified by comparing the 'consensus' sequence and in particular locating areas where dashes cluster (see FIG. 12). Using this type of analysis approximately 12 regions within the ssrRNA gene from the chicken Eimeria have been identified which contain sufficient species-to-species nucleotide sequence diversity to be useful hybridization probe targets, i.e. regions which will serve as templates for oligonucleotide hybridization probes. Table 5 lists these regions using the 'aligned' nucleotide numbering system. Table 5 lists the same regions using the absolute sequence numbering system for each species as illustrated in FIGS. 1-7. The following table contains the nucleotide position for each region of Table 4, for each of the Eimeria species.

TABLE 5

Species: Region, (Nucleotide Span)

E. acervulina: 1, (106-113); 2, (153-179); 3, (188-215); 4, (254-267); 5, (631-728); 6, (927-934); 7, (1031-1047); 8, (1057-1063); 9, (1155-1168) 10, (1336-1378); 11, (1473-1515); 12, (1665-1700).
E. brunetti: 1, (106-113); 2, (153-179); 3, (188-222); 4, (252-264); 5, (629-726); 6, (925-932); 7, (1030-1045); 8, (1054-1061); 9, (1153-1167); 10, (1334-1375); 11, (1470-1512); 12, TABLE 5-continued Species: Region, (Nucleotide Span)

(1661-1669).
E. maxima; 1, (106-113); 2, (153-179); 3, (188-226); 4, (256-269); 5, (633-730); 6, (929-936); 7, (1034-1049); 8, (1059-1065); 9, (1157-1170); 10, (1338-1380); 11, (1475-1517); 12, (1667-1702).
E. mitis: 1, (106-113); 2, (153-179); 3, (188-223); 4, (253-266); 5, (630-725); 6, (923-928); 7, (1026-1041); 8, (1051-1057); 9, (1149-1161); 10, (1329-1380); 11, (1474-1517); 12, (1667-1701).
E. necatrix; 1, (106-114); 2, (154-180); 3, (188-226); 4, (255-271); 5, (635-732); 6, (931-938); 7, (1036-1051); 8, (1060-1067); 9, (1159-1172); 10, (1340-1384); 11, (1479-1521); 12, (1671-1708).
E. preacox: 1, (106-113); 2, (153-179); 3, (188-223); 4, (253-266); 5, (630-727); 6, (927-933); 7, (1031-1046); 8, (1056-1062); 9, (1154-1168); 10, (1335-1375); 11, (1471-1514); 12, (1664-1699).
E. tenella: 1, (106-114); 2, (154-180); 3, (189-226); 4, (255-271); 5, (635-732); 6, (931-938); 7, (1036-1047); 8, (1061-1067); 9, (1159-1172); 10, 1340-1384); 11, (1479-1521); 12, (1671-1708).

EXAMPLE 2

Infectivity Assay

Live coccidiosis vaccine lots were produced using oocysts from attenuated strains of Eimeria. A vaccine was prepared with the following Eimeria species: E. acervulina, E. tenella, E. maxima, E. necatrix, E. praecox, E. mitis, E. brunetti. An immunogenic dose of oocysts from each species was combined, beaded in wax and covered with gypsum. One day old female SPF Leghorn chicks were housed in isolator cages and given non-vaccine containing feed and water ad libitum until two weeks of age. Feed was removed on the day prior to administration of the vaccine. Vaccine beads were weighed and aliquots equivalent to 0.25X, 0.5X, 1X, 2X, 3X, 5X and 10X vaccine dose were mixed with feed (15 g/chick) and presented to the chicks in groups of 8 to 10 animals. All vaccine was consumed within four hours. After the vaccine was fully consumed, vaccine-free feed was administered for the duration of the test. A group of 8 to 10 untreated birds were fed regular feed and water ad libitum for the duration of the experimental regimen. One additional group of 8 to 10 birds was dosed by gavage with the the same number of unencapsulated oocysts (1X) and fed ad libitum. These birds represented a positive control for infection and served to check the viability of organisms following encapsulation since the unencapsulated oocysts were from the same production batch as those in the vaccine. Three to five days following administration of the vaccine or unencapsulated oocysts, mucosal and epithelial scrapings were prepared from the intestinal walls of the birds. Total nucleic acids extracted from these scrapings served as the hybridization target or PCR amplification template in this protocol. The relative infectivity of each species of Eimeria subsequent to the encapsulation process was estimated based upon the ability to detect an amplification of the number of input oocysts. This was accomplished using the species-specific $^{32}$P-labeled oligonucleotide hybridization probes described in Example 1. Some of the birds in each treatment group were saved to monitor fecal oocyst counts from days four to seven post-infection. Quantitation was based on a standard curve using genomic DNA prepared from cloned vaccine strain oocysts.

Preparation Of Total Nucleic Acids

Chickens were sacrificed 3-5 days after receiving a vaccine dose. The intestine and the ceca were removed, cut along their length and rinsed with tap water. The interior wall of the intestine and ceca were scraped using a microscope slide. The scrapings were transferred to a 50 ml centrifuge tube and processed immediately. Five to 10 ml of 2X Proteinase K digestion buffer (400 mM Tris-HCl, pH 7.6, 100 mM EDTA, 1.0 % SDS) were added to the scrapings and the suspension was mixed vigorously on a vortex mixer. To the suspension was added 200 μl of 5 mg/ml proteinase K and the suspension was allowed to digest at 55° C. for 3 hours. If viscosity was a problem at this point another 5 ml of digestion buffer and another 100 μl of 5 mg/ml proteinase K were added and digestion was continued overnight. Following the overnight digestion, 100 μl of 5 mg/ml proteinase K was added and digestion was continued for up to 3 to 24 hours. Six hundred microliters of the digest was removed and placed into a 1.5 ml microfuge tube and extracted twice with a 1:1 mixture of digestion buffer equilibrated phenol and chloroform. The samples were then extracted with a 24:1 mix of chloroform and isoamyl alcohol. The final aqueous phase was stored at −20° C. An aliquot of the final aqueous phase was ethanol precipitated. In most cases 200 μl of the final aqueous phase was added to 20 μl of 3M sodium acetate (pH 4.6) and then combined with 500 μl of ethanol. The samples were mixed by inversion and placed in a dry ice ethanol bath for 20 minutes. The genomic DNA was then collected by centrifugation in an Eppendorf microcentrifuge for 15 minutes. The precipitate was washed once with 70% ethanol and dried in a Speed-Vac (Savant). The precipitate was suspended in 200 μl of deionized water. The amount of DNA in the total nucleic acid preparation was estimated using bisbenzimide which is a fluorochrome whose properties change when bound to DNA as mentioned previously. Salmon testes DNA standards ranging from 0 to 20 μl/100 μl in TE were made from a stock solution. Dilutions were prepared in 12×75 mm borosilicate tubes using sterile tips which were changed between dilutions. Similarly, 1:10 dilutions were prepared to a final volume of 100 μl for each experimental sample in duplicate. A bisbenzimide dye stock at a concentration of 200 μl per ml sterile water was prepared and stored at 4° C. in a dark bottle. Prior to use, the dye stock was diluted 1:200 with a buffer whose composition was 50mM sodium phosphate, pH 7.6, 2M NaCl. Two milliliters of this were added to each borosilicate tube with an Eppendorf repeater pipette, mixed and measured directly in a fluoro-colorimeter at an excitation wavelength of 356 nm and an emission wavelength of 458 nm. The amount of DNA in the experimental samples was determined after calibrating the machine with the appropriate standards as described by the manufacturer.

PCR Amplification Of Protozoan ssrRNA Sequences From Genomic DNA Prepared From Chicken Intestinal Epithelial and Mucosal Scrapings Due to the exquisite sensitivity of this technique, extreme caution was exercised to avoid contamination. Dedicated pipettes, pipette tips, vessels and stock solutions for DNA preparation, reaction assembly and sample analysis were used. Two hundred ng of experimental genomic DNA based upon the bisbenzimide assay above were used as the starting target material. This material was first ethanol precipitated to remove solvents remaining from the extractions which inhibit the Taq DNA polymerase. Genomic DNAs prepared from known numbers of purified organisms from each of the species of Eimeria were used to "spike" 200 ng of chicken hepatic genomic DNA. These served as amplification standards and hybridization specificity standards. A daily working solution of Tris-HCl buffered (pH 7.6) deoxynucleoside triphosphates dATP, dCTP, dGTP and dTTP each at 1.25 mM was prepared from 100 mM stocks stored frozen at −20° C. A 10X reaction buffer composed of 100 mM Tris- HCl, pH8.3, 500 mM KCl, 15 mM $MgCl_2$, 0.01% gelatin was prepared and autoclaved. This was then aliquoted and stored at −20° C. The reaction mix was assembled in dedicated PCR reaction tubes in a final volume of 100 μl. A reaction mix cocktail was prepared by mixing the following components at these final concentrations in this specific order: water, dATP, dCTP, dGTP and dTTP (dNTPs each at 200 μM), 1X reaction buffer, and 1 μl of each of the two amplification primers (ERIB 1 and ERIB 2) (SEQ ID NO:1 and SEQ ID NO:3), then mixed, and 1.25 U Taq DNA polymerase per reaction tube was added and mixed by inversion. An aliquot of 80 μl of the cocktail was then distributed to each reaction tube. Based on the bisbenzimide DNA assay described above, 200 ng of experimental genomic DNA was adjusted to a final volume of 20 μl with distilled water and added to the reaction mixture. The BIOS thermal cycler was programmed as follows:

a) 3 cycles consisting of 94° C. for 1 minute to denature, 50° C. for 30 seconds to anneal and 72° C. for 45 seconds for polymerization;

b) 27 cycles consisting of 94° C. for 20 seconds to denature, 50° C. for 30 seconds to anneal and 72° C. for 45 seconds for polymerization;

c) one cycle at 72° C. for 10 minutes.

When using primer pairs 5AERIB/3AERIB (SEQ ID NO:31/SEQ ID NO:32) or 5BERIB/3BERIB (SEQ ID NO:33/SEQ ID NO:34), a reaction mixture was prepared by mixing the following components at these final concentrations in this specific order: water, dATP, dCTP, dGTP and dTTP (dNTPs each at 200 μM), 1X reaction buffer, and 1 μM of each of the two amplification primers (5AERIB [SEQ ID NO:31] and 3AERIB [SEQ ID NO:32] or 5BERIB [SEQ ID NO:33] and 3BERIB [SEQ ID NO:34], then mixed and 1.25 U Taq DNA polymerase per reaction tube was added and mixed by inversion. An aliquot of 80 μl of the mixture was then distributed to each reaction tube. Based on the bisbenzimide DNA assay described above, 200 ng of experimental genomic DNA was adjusted to a final volume of 20 μl with distilled water and added to the reaction mixture. The reaction was overlayed with approximately 50 μl of light mineral oil and then placed into a Perkin Elmer Cetus DNA thermal cycler programmed as follows:

a) 3 cycles consisting of 94° C. for 1 minute to denature, 480 C. for 1 minute to anneal and 72° C. for 1 minute for polymerization;

b) 32 cycles consisting of 94° C. for 1 minute to denature, 50° C. for 1 minute 30 seconds to anneal and 72° C. for 2 minutes for polymerization;

c) one cycle at 72° C. for 10 minutes.

Five μl of the reaction product were then assayed for DNA content using a small scale bisbenzimide assay analogous to that described above. The small scale assay used dilutions in microcentrifuge tubes in duplicate, with a final assay volume of 500 μl. The samples were read in a microcell and the standard curve was linear from 5 to 200 ng/ml.

Immobilization Of Nucleic Acids On A Nylon Support In A Slot-blot Or Dot-blot Manifold Generally, 100 ng of PCR product as quantitated above was adjusted to 100 μl with water and applied to Nytran sheets (prewetted in water) in a slot-blot or dot-blot manifold as per the manufacturer's specifications (Schleicher and Schuell, Inc.). To each sample was added 1 volume of 1M NaOH. The samples were then incubated at room temperature for 5 minutes to denature the DNA and subsequently neutralized by adding 1 volume of 1M Trim-HCl (pH 7.3). A vacuum was then applied to the apparatus to filter the samples. Each sample was then rinsed with 500 μl of 4M ammonium acetate (pH 6.8). Genomic DNA prepared from purified organisms representing each of the species of chicked Eimeria and subjected to PCR as described previously was used to "spike" chicken hepatic genomic DNA also subjected to PCR as described previously. The spiked DNA was applied to the filters and served as a species-specific quantitation standard. Appropriate buffer controls and blank slot controls were routinely included. The filters were air dried and baked under vacuum at 80° C. for 2 hours (optional).

Oligonucleotide hybridization probes (from Example 1) were end labeled with gamma $^{32}$P-ATP. The oligonucleotides were quantitated and standardized using the the following formula (1 mg/ml=25 $A_{260}$). Five to ten picomoles of oligonucleotide were added to a 50 μl reaction volume containing water, 5 μl of 10X kinase buffer (0.5 Tris-HCl, pH 7.6, 0.1M $MgCl_2$, 50 mM DTT, 1 mM spermidine, 1 mM EDTA), 20U of polynucleotide kinase, and at least two fold molar excess of gamma $^{32}$P-ATP (specific activity >5000 Ci/mmol). The mixture was incubated for 30 minutes at 37° C. and then stopped by the addition of 4 μl of 0.5M EDTA, 46 μl of TE. The reaction mixture was extracted once with a 1:1 mixture of buffer equilibrated phenol and chloroform and the aqueous phase was passed through a Stratagene push column (Stratagene) as per the manufacturer's specifications to remove the unincorporated isotope from the labeled oligonucleotide.

Prehybridization, Hydridization And Washes

Prehybridization was carried out in a buffer whose composition was 6X SSPE, 1% SDS, 10X Denhardt's, 100 μl per nil TRNA. The buffer was made and kept at 42° C. until ready for use to keep the SDS in solution. The dry sheet(s) of Nytran were prewetted in 6X SSPE, placed in a polyethylene freezer bag which was heat sealed on three sides. The prehybridization solution (20–40 ml depending on the number of sheets of Nytran in the bag) was added and the bag was sealed on the fourth edge after removing the bulk of the air bubbles, secured to a glass plate with elastic bands and submerged in a water bath at 42° C. for at least 3 hours or for as long as overnight. Following prehybridization the bag was cut open and the buffer was removed completely. The hybridization buffer was 6X SSPE plus 1% SDS. Hybridization was done at the $T_h$ of the desired hybrid. For probes less than 25 nucleotides in length, hybridization conditions were determined using the following formula:

$$T_h = T_m = 5° C. = 2° C.(A - T \, bp) + 4° C.(G - C \, bp) - 5° C.$$

The end labeled oligonucleotide probe was warmed at 68° C. for 5 min prior to mixing with 10-20 ml (depending on the number of filters per bag; approx. 1-5×10$^6$ dpm/ml) of hybridization buffer which was prewarmed at the $T_h$. This was poured into the bag, air bubbles were removed and the bag was resealed. The bag was secured to a glass plate and submerged in a water bath at the $T_h$ for at least 12 hours to overnight for hybridization. Following hybridization, the bag was cut open and the buffer was discarded. The remaining three sides of the bag were cut and the filters were removed with forceps to a pyrex dish containing the first wash solution. The washes were as follows:
a) 3 times for 5-10 minutes each in 6X SSPE, 1% SDS at 37° C. with shaking;
b) 1 time for 3 min in 1X SSPE, 1% SDS at the $T_h$ of the hybrid;
c) 3-4 times for approx. 5 min each in 6X SSPE at room temperature with shaking to remove the SDS.

Wash volumes were at least 100 ml; more with multiple filters. All wash solutions were prewarmed at the respective temperatures prior to use. The filters were air dried, placed in a cassette, which contained two intensifying screens, and exposed to X-ray film at −70° C. The film was developed after 1-3 days. Quantitation of hybridization signal was carried out using the Molecular Dynamics PhosphorImager (Molecular Dynamics). Dried blots were placed beneath plastic wrap in the PhosphorImager cassette as per the manufacturer's instructions and exposed to the phosphor for approximately 2 hours for the common hybridization probe and 3-12 hours for the specific Eimeria probes. The screen was then scanned with a laser which releases the energy captured by the phosphor in the screen. The released energy was quantitated by the machine.

EXAMPLE 3

Use Of Specific Eimeria Species Small Subunit Ribosomal RNA Probes And Assay

Purified oocysts from multiple strains of each of the seven species of chicken Eimeria were prepared as described in Example 1. Sporocysts were purified after disruption of the oocyst shell. Genomic DNA was prepared from each population of sporocysts and quantitated using the bisbenzimide assay. Four micrograms of each preparation of genomic DNA were denatured and immobilized on a Nytran membrane in eight equivalent 0.5 ug aliquots. Gloves were worn and forceps used whenever handling Nytran. Generally about 0.5 μg of genomic DNA was adjusted to about 100 μl (4 μg/800 μl ) and added to 0.1 volume of 3M NaOH. This was incubated at about 70° C. for about 30 to 60 minutes to denature the DNA, cooled to room temperature, neutralized by adding about one volume of 2M ammonium acetate (pH 7.0)) and applied to Nytran sheets in a slot-blot or dot-blot manifold as described by the manufacturer (Schleicher and Schuell, Inc). Vacuum was applied to the apparatus to filter the samples. Appropriate buffer controls and blank slot controls were routinely included. The filters were air dried and baked under vacuum at about 80° C. for about 2 hours. Chicken genomic DNA (Clonetech Laboratories, Inc.) was similarly denatured and immobilized. The eight filters were prehybridized in individual bags and then hybridized with the respective species-specific probes (X7) and a probe common to all eukaryotic ssrRNA gene sequences. The common probe used was 'common RC' with the following sequence: AGCCATTCGCAGTTT-CACCG (SEQ ID NO:22). The common probe was derived from highly conserved sequence segments. This is only an example of one of many such probes which could be made for conserved sequences within the ssrRNA gene. It is understood that only those sequences which are spanned by the particular PCR primer pair are useful as probes for that target. These probes could be used to normalize the signal across broad phylogenetic groups (i.e. Eimeria and Gallus). FIG. 8 shows the results generated using the E.tenella specific probe (WEt1RC) (SEQ ID NO:20). Only those slots in the grid containing E. tenella genomic DNA gave positive hybridization signals or response with WEt1RC. The DNA in these slots was derived from a field isolate, a laboratory strain, a precocious isolate (the vaccine strain) and a clonal derivative of the vaccine strain. Each of the four gave roughly equivalent hybridization signals. This indicates that the hybridization probe is species-specific, but not specific for the vaccine strain.

Similar types of experiments designed to verify the species-specific hybridization characteristics for the remaining six Eimeria probes were conducted and the results from three of these are depicted in FIG. 9. Probes derived from the ssrRNA genes of E.praecox (WEp1RC) (SEQ ID NO: 18), E.maxima (WEmx1RC) (SEQ ID NO:11) and E.necatrix (WEn-1M) (SEQ ED NO;38) (from Example 2) are indeed species-specific. As is the case with each of the Eimeria probes, hybridization to both nonprecocious laboratory isolates and vaccine strains is roughly equivalent.

Hybridization of the eighth replicate filter with the probe derived from ssrRNA gene nucleotide sequence common to eukaryotes (common RC, SEQ ID NO:22) indicated that an equivalent amount of "hybridizable" genomic DNA was immobilized in each of the labeled grids.

Figure 10:
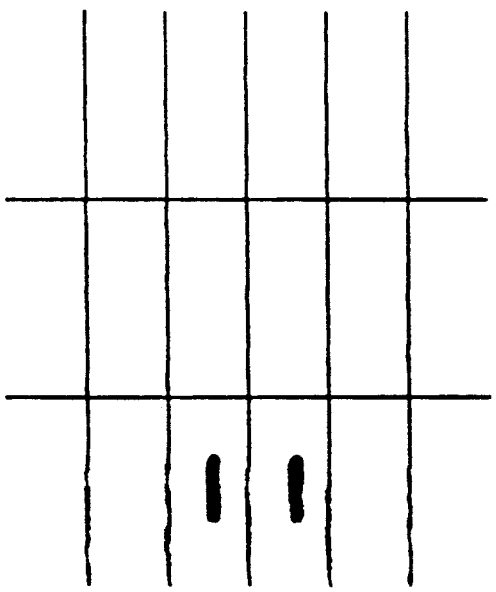
FIG. 10. Species-specific detection of Eimeria in the intestinal mucosa of infected chickens.

Groups of two chickens were each dosed by gavage with 2,500 purified oocysts of a single species of chicken Eimeria. An additional pair of birds did not receive any oocysts. Five days later the birds were sacrificed, the intestinal epithelia and mucosa was scraped and genomic DNA was prepared from this tissue. The resulting DNA was quantitated and 200 ng were aliquoted for use as a reaction substrate in the polymerase chain reaction (PCR) along with the PCR amplification primers ERIB 1 (SEQ ID NO:1) and ERIB 2 (SEQ ID NO:3). Ten percent of the reaction product was then denatured and immobilized on eight identical slot blot grids. FIG. 10 shows the results from hybridization of one of these panels with the E.brunetti specific probe (AEb1RC) (SEQ ID NO:8). Only those birds dosed with E.brunetti oocysts gave a positive hybridization signal with this probe. These and similar results with the other hybridization probes not only reconfirmed the species-specific nature of the respective hybridization probes but, also and more importantly, indicated a high sensitivity for the detection of an infection stemming from 2500 oocysts.

Figure 11:
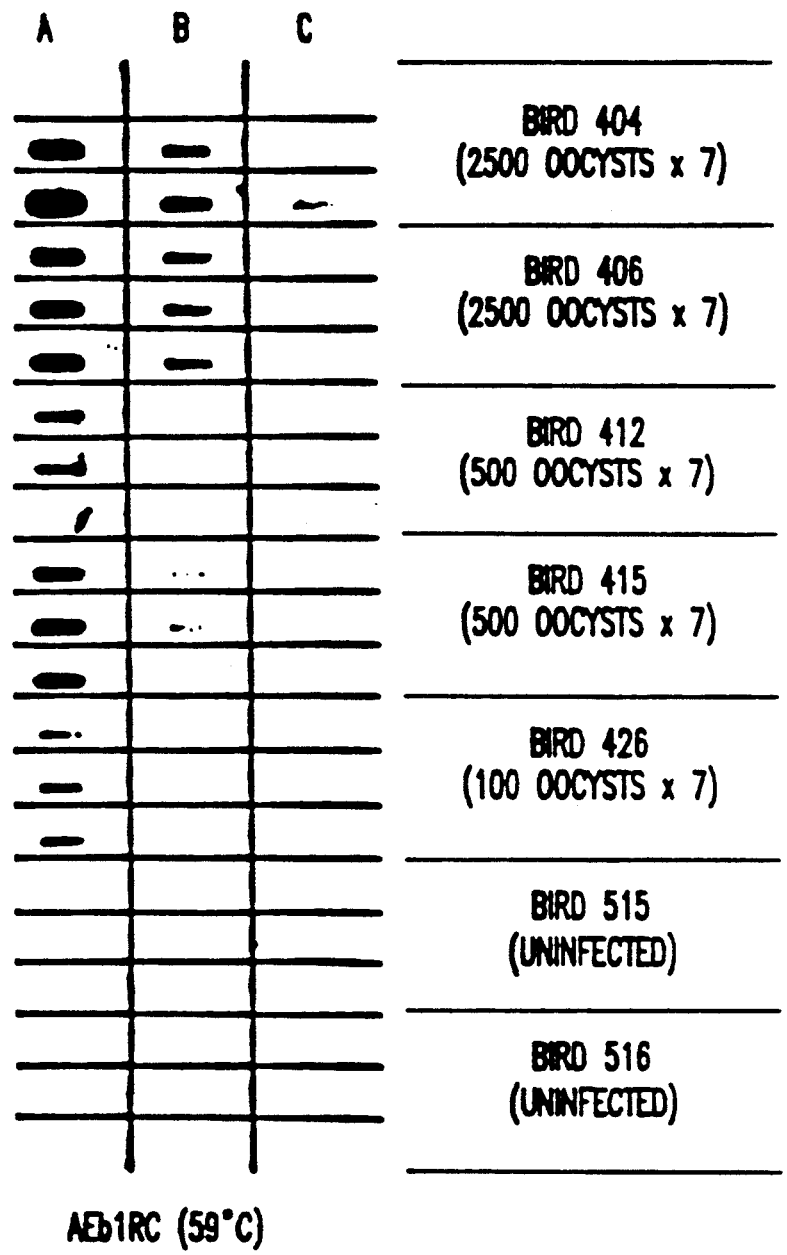
FIG. 11. Species-specific detection of Eimeria in the intestinal mucosa of heptavalent infected chickens.

The vaccine dose however was considerably fewer than 2500 oocysts and was composed of all seven species of chicken Eimeria. In the next experiment an equal number of oocysts from all seven species were mixed together and birds were dosed by gavage with a titration of this heptavalent mixture. The range of the dose titration was from 100 oocysts of each of the seven species to 2500 oocysts of each of the seven species. Five days following infection intestinal epithelia and mucosa was scraped and genomic DNA was extracted and quantitated (as described in Example 2). Two hundred nanograms of each sample were used as reaction substrates in the PCR using the ERIB 1 (SEQ ID NO:1) and ERIB 2 (SEQ ID NO:3) amplification primers. The reactions were done in triplicate and the products from these individual reactions were immobilized in successive rows in the slot blot manifold as is indicated in the right hand margin of FIG. 11. In addition, 10 μl (10%), 1 μl (1%) and 0.1 μl (0.1%) of each reaction product was loaded in columns A, B and C respectively. Seven identical filters were prepared and each was hybridized with one of the species-specific probes. Results using the E.brunetti specific probe (AEb1RC) (SEQ ID NO:8) are shown in FIG. 11. Importantly, an unequivocal hybridization signal was detected in bird 426 which received a dose of 100 oocysts of each species. This result indicates that the PCR/hybridization assay is sensitive enough to detect an infection in the intestine of a chicken that had received a 1X vaccine dose (100 oocysts for E.brunetti). Similar results were obtained with probes specific for the remaining six species.

FIG. 11 also serves to illustrate that triplicate polymerase chain reactions do not result in equivalent amounts of reaction products, despite starting with an equivalent amount of the same reaction substrate. This observation has led us to incorporate two standardization steps into the assay protocol. First, the products resulting from the PCR are quantitated in a small scale bisbenzimide assay which consumes only 5% of the reaction. Using this result, 800 ng of product were denatured and immobilized onto Nytran paper in eight equivalent aliquots of 100 ng each. The eighth replicate filter was routinely hybridized with the common probe (common RC) (SEQ ID NO:22) to confirm that an equivalent amount of denatured and immobilized hybridization target was present in each experimental slot on the filter.

EXAMPLE 4

Assay Method For Detecting Eimeria Ribosomal RNA With Species-Specific Oligonucleotides Isolation of Eimeria RNA from chicken intestines was carried out with care to avoid degradation of the RNA. The protocol is essentially the same as published in Chirgwin et al., Biochemistry 18: 5294–5299 (1979). Chickens were orally infected with oocysts fom laboratory strains of E. acervulina. E. brunetti. E. maxima. E.mitis. E. necatrix. E. praecox and E. tenella. Five days later the chickens were sacrificed. Their intestines and ceca were taken out, cut along their length, and rinsed throughly with running tap water. The interior walls of the intestines and ceca were scraped with a sterile microscope slide. The mucosal scrapings from each chicken were taken and transferred to a 50 ml centrifuge tube. These scrapings were immediately placed into 24 ml of about 4M guanidine thiocyanate, pH 7.0, 0.5% sodium N-lauroylsarcosine, 25 mM sodium citrate, 0.1M 2-mercaptoethanol, and 0.1% Sigma 30% Antifoam A. The samples were quickly homogenized with a Polytron (Brinkmann) at full speed three times for 20 seconds; between samples the Polytron was rinsed 2 times with sterile distilled water. The samples were then centrifuged at approximately 8000 RPM for 10 minutes at about 10C. in a swinging bucket rotor (JS-13, Beckman). The supernatant fluids were decanted and precipitated with 0.6 ml of 1M acetic acid and 18 ml of 100% ethanol at −20° C., overnight. The next day the samples were centrifuged again at 8000 RPM for 10 minutes at 10C. The pellets were resuspended in 12 ml of 7.5M guanidine hydrochloride, pH 7.0, 25 mM sodium citrate, and 5 mM dithiothreitol, shaken vigorously, and heated to 68° C. until dissolved. The samples were precipitated with 0.3 ml of 1 M acetic acid and 6 ml of 100% ethanol at −20° C., overnight. Again the samples were centrifuged, resuspended, and precipitated overnight at −20° C. as before, except with one-half the previous volumes, i.e. 6 ml, 0.15 ml, and 3 ml respectively. The samples were pelleted once again, triturated with about 10 ml of room-temperature 95% ethanol, transferred to baked Corex centrifuge tubes, and repelleted at 10,000 RPM for 30 minutes at about 10° C. The RNA pellets were dried under vacuum in a Speed-Vac (Savant Instruments), dissolved at 68° C. in 2 ml diethyl pyrocarbonate-treated sterile distilled water, repelleted, re-extracted with about 1 ml diethyl pyrocarbonate-treated sterile distilled water, and repelleted again. The extractions were re-precipitated with 300 μl of 2M potassium acetate, pH 5.0, and 8 ml of 100% ethanol at −20° C. overnight. The final RNA was pelleted and resuspended in 1 ml of diethyl pyrocarbonate-treated sterile water. Absorbance readings at 260 nm and 280 nm (Beckman spectrophotometer) were taken to determine RNA concentations; about 3 μg of RNA was then subjected to electrophoresis on a 1.2% agarose gel to check the RNA quality, size, and relative concentration. RNA samples were stored at −70° C. One milligram of RNA was subjected to DNase-1 digestion using RQ1 DNase (Promega) for 40 minutes at 37° C. as per the manufacturer's specifications and then precipitated with 1/10th volume of 3M NaOAc and 2.5 volumes of 100% ethanol. Duplicate samples containing twenty micrograms of RNA were denatured in 100 μl of 1 X denaturation solution (four times denaturation solution contained 1 ml of formaldehyde, 56 μl of 1M sodium phosphate, pH 6.5, and 344 μl of sterile distilled water.) at 68° C. for 20 minutes. The denatured samples were then placed on ice to cool. The denatured RNA samples were dotted in duplicate using a Bio-Rad dot-blot apparatus, Nytran filters (S & S), and 10X SSPE. The filters were dried for one hour in an 80° C. oven. The filters were probed with $^{32}$P-labelled oligos as in example 2. The filters were prehybridized and hybridized as per the manufacturer's specifications (Schleicher & Schull) for RNA hybridizations using oligonucleotide probes and using a $T_h$ as specified for each oligo as previously described. The results are shown in FIGS. 13 and 14.

Figure 13:
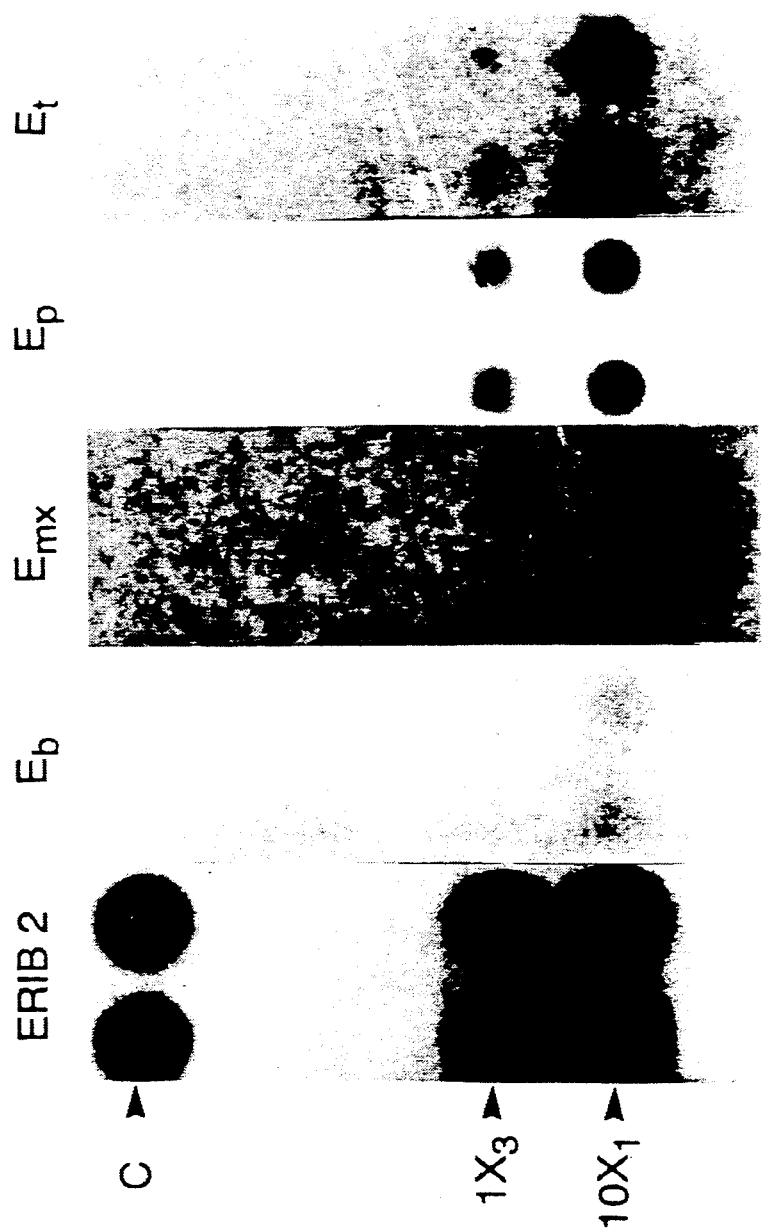
FIG. 13. DNA dot blot analysis using total RNA and species-specific oligonucleotide probes.

FIG. 13 is a composite of five Nytran filters (Schleicher & Schull) on which approximately 30 μg of DNase 1 digested total cellular RNA was spotted. The RNA was derived from duplicate chickens given a heptavalent mixture of oocysts. The filters were processed as described above. The row labeled 'C' was an uninfected chicken control. The rows labeled '1X' and '10X' represented the vaccine dosage used while the adjacent rows represent duplicate samples. The panel labeled 'ERIB2' was a control panel to establish equal loading. It was probed with the Erib2 oligonucleotide (SEQ ID NO 3) the sequence of which is derived from a highly conserved region of the ssrRNA genes and which hybridized to both the infected and uninfected controls. The panel labeled 'Eb' was probed with the oligonucleotide AEblRC (SEQ ID NO: 8) and at the 10X dose a faint E. brunetti signal was seen. The panel labeled 'Emx' was probed with WEmxlRC (SEQ ED NO: 11). A faint E. maxima signal was seen at 10X and clearly seen at the 10X dose. The panel labeled "Ep" was probed with WEplRC (SEQ ID NO: 18) and E. praecox was demonstrated in both the 1OX and 1OX doses. The panel labeled 'Et' was probed with WEtlRC (SEQ ID NO: 20) and a faint E. tenella signal was seen at the 1X dose, while the 1OX dose is clearly seen.

Figure 14:
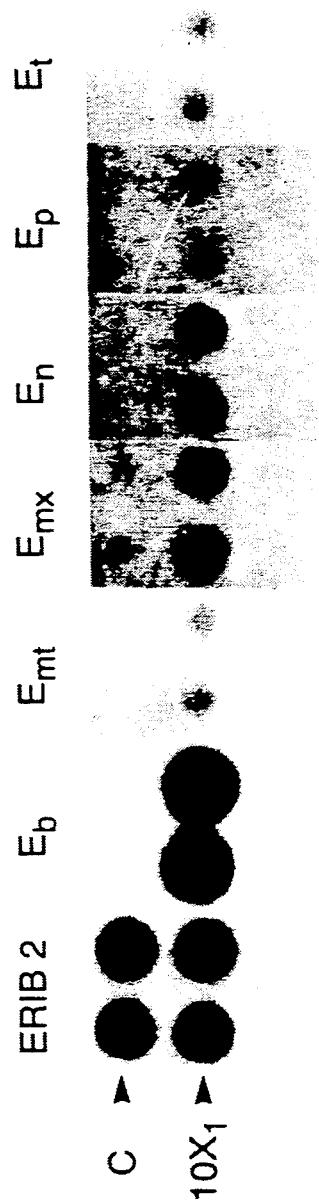
FIG. 14. DNA dot blot analysis using total RNA and species-specific oligonucleotide probes.

FIG. 14 is similar to FIG. 13 except that only the 1OX dose was used and different oligonucleotides were used as hybridization probes. The panel labeled 'ERIB2' was probed with the oligonucleotide Erib2 (SEQ ID NO 3) and it hybridized to both infected and uninfected controls with equal intensity. The panel labeled 'Eb' was probed with the oligonucleotide PEb4e-RC (SEQ ID NO: 36) and an E. brunetti signal was clearly observed. The panel labeled 'Emt' was probed with PEmt4-RC (SEQ ID NO: 15) and E. mitis was detectable at this level. The panel labeled 'Emx' was probed with PEmx-4a-RC (SEQ ID NO: 37) and an E. maxima signal was seen. The panel labeled 'En' was probed with the oligonucleotide PEn4-RC (SEQ ID NO: 17) and an E. necatrix signal was observed. The panel labeled 'Ep' was probed with PEp4d-RC (SEQ ID NO: 39) and a faint E. praecox signal was detected. The panel labeled 'Et' was probed with PEt4a-RC (SEQ ID NO: 40) and an E. tenella signal was observed.

EXAMPLE 5

A METHOD FOR DESIGNING SPECIES SPECIFIC OLIGONUCLEOTIDE HYBRIDIZATION PROBES

Once the ssrRNA sequences from all seven avian Eimeria were determined and aligned nonconserved regions were identified. The sequences within the nonconserved regions were analyzed to determine if there were sufficient differences to allow the construction of species specific oligonucleotide hybridization probes. There were three constraints which we placed on the design of our hybridization probes. One was that the probes be species specific. Due to the nature of the assay cross hybridization could not be tolerated. The second was to have a set of oligonucleotide hybridization probes which had melting temperatures ($T_m$) which were as close as possible to a single temperature so as to allow the use of a single hybridization temperature. This constraint was more a matter of convenience than necessity. The last constraint was to make the oligonucleotides the reverse compliment of the sense strand, so the the probes could be used for probing either DNA or RNA. Starting with the sequence for the nonconserved region an oligonucleotide was found which had a $T_m$ of approximately 60° C. The probe was synthesized and tested for specificity.

The target DNA for these specificity studies was obtained in the following manner. Genomic DNA from each of the seven Eimeria species was used as DNA template in the PCR using two amplification primers 5ERIB (SEQ. ID NO: 4) and 3ERIB (SEQ ID NO: 5). The use of this particular primer pair is important since they would not produce an amplification product when the DNA temple was derived from either chicken or E. coli, i.e. the primer pair is specific for Eimeria ssrRNA genes. This primer pair flanks the nonconserved region to which the oligonucleotide hybridization probes were designed. The reactions were run in the Perkin-Elmer Cetus DNA thermal cycler. The reactions contained about 25ng of Eimeria genomic DNA and were set up as previously described for this machine. The Perkin-Elmer Cetus DNA thermal cycler was programmed as follows:
 a) about 35 cycles consisting of 94° C. for about 1 minute to denature, about 50° C. for about 1.5 minutes to anneal and about 72° C. for about 2 minutes for polymerization.
 b) about one cycle at about 72° C. for about 10 minutes.

About 5 ml of the reaction mixture is then assayed for DNA content using the small scale bisbenzimide assay. About 5 ml of the reaction mixture is electrophoresed on an about 2% agarose gel to ensure that the reaction produced a single amplification product. About 10 ng of the PCR product was adjusted to a final volume of about 100 µl with water, and applied to Nytran sheets (prewetted in water) in a slot-blot manifold as described in the manufacturer's specifications (Schleicher and Schuell, Inc.). To each sample was added about 1 volume of 1M NaOH. The samples were then incubated at about room temperature for about 5 minutes to denature the DNA and were neutralized by adding about 1 volume of 1M Trim-HCl (pH 7.3). A vacuum was then applied to the apparatus to filter the samples. Each sample was then rinsed with about 500 ml of 4M ammonium acetate (pH 6.8). Appropriate buffer controls and blank controls were included. The Nytran sheets were air dried then baked under vacuum at about 80° C. for about 2 or more hours. The test probe was labelled for hybridization. The preferred method was to end label the test oligonucleotides with gamma $^{32}$P-ATP by methods which have been previously described. Prehybridizations, hybridizations and washes were also carried out as previously described. Since specificity was the major issue being addressed, a probe was considered species-specific when only the slot containing the targeted species DNA yielded signal. If any other slot gave a signal the probe was not species-specific and not useful in this context.

Figure 15:
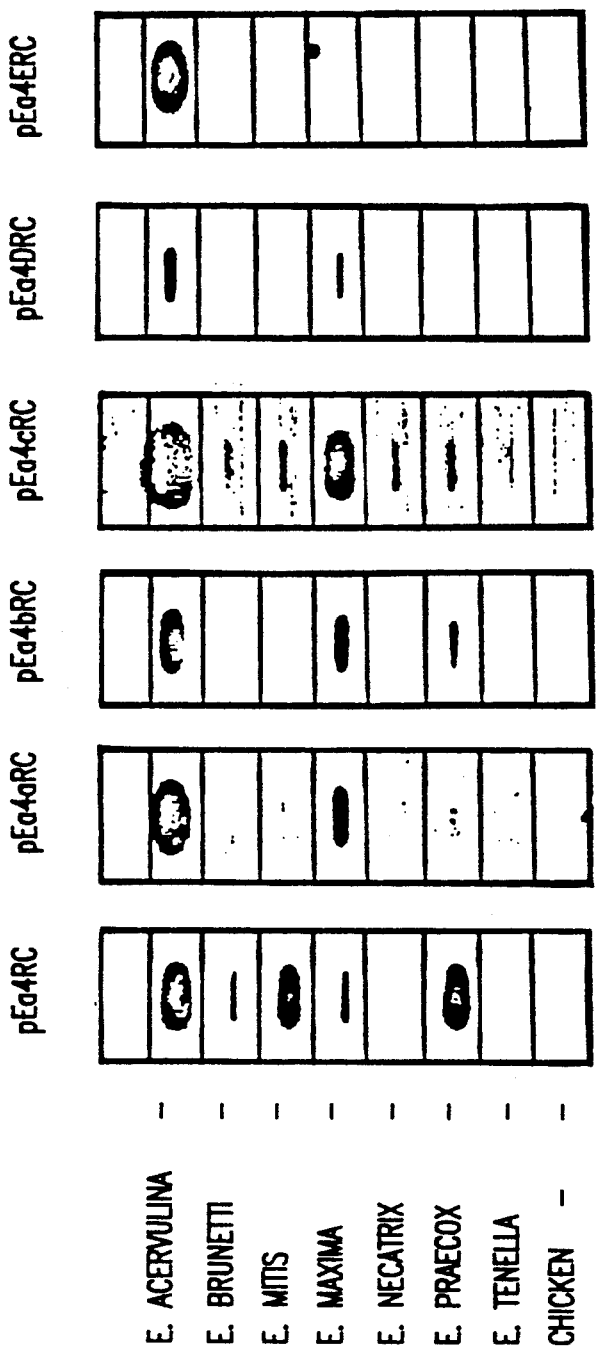
FIG. 15. Design of species-specific oligonucleotide probes.

FIG. 15 illustrates the development of a species-specific hybridization probe for *E. acervulina* in region 10. The first oligonucleotide synthesized was pEa4-RC (SEQ. ID NO: 7) which hybridized with the *E. acervulina* target as well as *E. bruneti, E. mitis, E. maxima,* and *E. praecox*. Further analysis revealed that a single base had been omitted (a T at position #12) so this probe was resynthesized to yield pEa4a-RC (SEQ. ID. NO: 46), which hybridized to the target *E. acervulina* as well as *E. maxima*. A dramatic improvement in the species-specificity was obtained by the addition of one base, however, some cross-hybridization did occur. The next oligonucleotide tested was pEa4b-RC (SEQ. ID. NO: 47) which not only hybridized to the target *E. acervulina* but also *E. maxima,* and *E. praecox* as well. Oligonucleotide pEa4c-RC (SEQ. ID. NO: 48) was synthesized and tested and found to be as good as pEa4a-RC. (SEQ. ID. NO: 46) When pEa4d-RC (SEQ. ID. NO: 49) was synthesized and tested it also was found to be as good as pEa4a-RC (SEQ. ID. NO: 46). Species-specificity was finally demonstrated when oligonucleotide pEa4e-RC (SEQ. ID. NO: 35) was synthesized and tested. A similar approach was used to develop species specific hybridization probes for the other six chicken Eimeria species.

EXAMPLE 6

Direct Hybridization to Genomic DNA Prepared from Fecal Oocysts as a Method for Parasite Detection and Quantitation Fecal oocysts from birds infected with a monovalent or a mixed inoculum of Eimeria oocysts were collected. Oocysts were purified from fecal material. Sporocysts were isolated and purified from sporulated oocysts. Methods for collection, purification and sporulation of oocysts, and subsequent purification of sporocysts have been described in Example 1. The number of sporocysts in each monovalent collection sample were counted either by Coulter counter or haemocytometer. Genomic DNA was prepared from a known number of each monovalent population of sporocysts as well as from the mixed population of sporocysts from the heptavalent infected groups of birds. The isolation of genomic DNA from sporocysts is described in Example 1. Methods for denaturation and immobilization of genomic DNA on nylon membranes for hybridization are described in Example 3.

Panels I and II in FIG. 16 illustrate typical results which demonstrate the feasibility of this particular method. The two panels are identically loaded and the order of loading is indicated by the text between the panels. Genomic DNA prepared from fecal oocysts of monovalent infected birds is immobilized in rows one through thirteen. A titration of sporocyst equivalents of this genomic DNA from each species is loaded in columns A, B and C. However, the absolute number of sporocyst equivalents differs among the species. For example, there are $1.24 \times 10^6$ *E. maxima* sporocyst equivalents in slots 7A, but only $1.0 \times 10^6$ *E. tenella* sporocyst equivalents in slots 11A. Slots 15A, B and C contain a titration of chicken genomic DNA and are included to serve as a negative hybridization control. Slots 17A, 17B, 17C and 18A contain 10% of the genomic DNA prepared from an unknown number of sporocysts purified from four separate heptavalent experimental infections.

Filters I and II were prehybridized in individual bags and then hybridized with the *E. maxima* (WEmx1RC, SEQ ID NO: 11) and the *E. tenella* (WEt1RC, SEQ ID NO:20) species specific probes, respectively. In panel I hybridization specificity is demonstrated by the observation that only row 7, which contains the *E. maxima* DNA target, shows a significant signal. Moreover, the signal intensity decreases from slot 7A to 7B to 7C which correlates with the titration of immobilized target DNA in these slots. Only one of the four experimental slots (number 19A) containing genomic DNA from heptavalent infected birds hybridized with the *E. maxima* probe. The intensity of the signal corresponds to the intensity seen with the signal in slot 7C, or roughly $0.3 \times 10^6$ sporocyst equivalents. Since 10% of the entire experimental sample was loaded in slot 19A, we estimate that the total number of *E. maxima* sporocysts in the mixed sporocyst population was on the order of $3 \times 10^6$. The lack of hybridization to DNA immobilized in slots 17A, 17B and 17C suggests that these experimental samples contain less than $1 \times 10^6$ *E. maxima* sporocyst equivalents.

Hybridization specificity with the *E. tenella* probe is demonstrated in panel II by the fact that only one of the seven monovalent infected experimental samples (row 11) generates a positive signal. The hybridization signal titrates in a manner which correlates with the relative amount of *E. tenella* sporocyst genomic DNA equivalents immobilized in slots 11A, 11B and 11C. The approximate number of sporocyst equivalents is indicated by the numbers over these slots. Two of the four experimental slots (numbers 17C and 19A) that contain genomic DNA from heptavalent infected birds hybridized with the *E. tenella* probe. By comparison to the hybridization signals in row 11, we estimate that slots, 17C and 19A contain $<0.25 \times 10^6$ and $0.5 \times 10^6$ sporocyst equivalents, respectively. Since these slots contain 10% of the total genomic DNA prepared from the experimental samples, the total number of *E. tenella* sporocysts in the mixed sporocyst population was on the order of $<2.5 \times 10^6$ and $5 \times 10^6$, respectively. By analogy, heptavalent infected experimental samples corresponding to slots 17A and 17B appear to contain less than $1 \times 10^6$ *E. tenella* sporocyst equivalents.

---

What is claimed is:

1. A DNA probe, the DNA probe consisting of 5' CAAGACTCCACAAGAATTGTG 3' (SEQ ID NO:11).

2. A composition, consisting essentially of a DNA probe consisting of 5' CAAGACTCCACAAGAATTGTG 3' (SEQ ID NO: 11).

* * * * *